US009027564B2

(12) United States Patent
Danek et al.

(10) Patent No.: US 9,027,564 B2
(45) Date of Patent: *May 12, 2015

(54) METHOD FOR TREATING A LUNG

(71) Applicant: Asthmatx, Inc., Sunnyvale, CA (US)

(72) Inventors: Christopher J. Danek, Santa Clara, CA (US); Bryan E. Loomas, Los Gatos, CA (US); Thomas M. Keast, Mountain View, CA (US); Michael D. Laufer, Menlo Park, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,959

(22) Filed: May 10, 2013

(65) Prior Publication Data

US 2013/0253492 A1    Sep. 26, 2013

Related U.S. Application Data

(63) Continuation of application No. 12/964,678, filed on Dec. 9, 2010, now Pat. No. 8,640,711, which is a continuation of application No. 12/727,156, filed on Mar. 18, 2010, now Pat. No. 8,161,978, which is a (Continued)

(51) Int. Cl.
*A61B 19/00* (2006.01)
*A61F 7/12* (2006.01)

(Continued)

(52) U.S. Cl.
CPC . *A61N 5/00* (2013.01); *A61B 18/08* (2013.01); *A61B 18/1492* (2013.01); *A61B 2017/003* (2013.01); *A61B 2018/00083* (2013.01); *A61B 2018/00214* (2013.01); *A61B 2018/0022* (2013.01); *A61B 2018/00267* (2013.01); *A61B 2018/00541* (2013.01);

(Continued)

(58) Field of Classification Search
USPC ............ 607/42, 96, 98–105, 124; 606/27, 28, 606/32, 41, 50; 128/898
See application file for complete search history.

(56) References Cited

U.S. PATENT DOCUMENTS

| 612,724 A | 10/1898 | Hamilton |
|---|---|---|
| 1,155,169 A | 9/1915 | Starkweather |

(Continued)

FOREIGN PATENT DOCUMENTS

| DE | 19529634 A1 | 2/1997 |
|---|---|---|
| EP | 189329 A3 | 6/1987 |

(Continued)

OTHER PUBLICATIONS

An S.S., et al., "Airway Smooth Muscle Dynamics: A Common Pathway of Airway Obstruction in Asthma," European Respiratory Journal, 2007, 29 (5), 834-860.

(Continued)

*Primary Examiner* — Ahmed Farah
(74) *Attorney, Agent, or Firm* — Bookoff McAndrews, PLLC

(57) ABSTRACT

An embodiment of the invention includes a method for decreasing resistance to airflow within a bronchial tree of a subject. The method may include the step of moving an intraluminal device along a lumen of an airway of a bronchial tree, where the intraluminal device includes an expandable member and an energy emitter. The method also may include damaging nerves along the airway using the intraluminal device without destroying an inner surface of an airway wall disposed radially between the intraluminal device and the nerves.

9 Claims, 33 Drawing Sheets

Related U.S. Application Data continuation of application No. 11/117,905, filed on Apr. 29, 2005, now Pat. No. 7,740,017, which is a continuation of application No. 09/999,851, filed on Oct. 25, 2001, now Pat. No. 7,027,869, which is a continuation-in-part of application No. 09/296,040, filed on Apr. 21, 1999, now Pat. No. 6,411,852, said application No. 11/117,905 is a continuation-in-part of application No. 09/436,455, filed on Nov. 8, 1999, now Pat. No. 7,425,212, and a continuation-in-part of application No. 10/232,909, filed on Aug. 30, 2002, now Pat. No. 7,556,624, which is a continuation of application No. 09/349,715, filed on Jul. 8, 1999, now Pat. No. 6,488,673, said application No. 09/999,851 is a continuation-in-part of application No. 09/535,856, filed on Mar. 27, 2000, now Pat. No. 6,634,363.

(51) Int. Cl.

| | | |
|---|---|---|
| *A61N 5/00* | (2006.01) | |
| *A61B 18/08* | (2006.01) | |
| *A61B 18/14* | (2006.01) | |
| *A61M 25/00* | (2006.01) | |
| *A61M 29/00* | (2006.01) | |
| *A61M 29/02* | (2006.01) | |
| *A61N 1/06* | (2006.01) | |
| *A61N 1/40* | (2006.01) | |
| *A61B 18/02* | (2006.01) | |
| *A61B 18/18* | (2006.01) | |
| *A61B 17/00* | (2006.01) | |
| *A61B 18/00* | (2006.01) | |

(52) U.S. Cl.
CPC ............... *A61B 2018/00654* (2013.01); *A61B 2018/00666* (2013.01); *A61B 2018/00678* (2013.01); *A61B 2018/00761* (2013.01); *A61B 2018/00791* (2013.01); *A61B 2018/00797* (2013.01); *A61B 2018/00803* (2013.01); *A61B 2019/5217* (2013.01); *A61M 25/0043* (2013.01); *A61M 29/00* (2013.01); *A61M 29/02* (2013.01); *A61M 2025/0096* (2013.01); *A61M 2210/1039* (2013.01); *A61N 1/06* (2013.01); *A61N 1/403* (2013.01); *A61B 18/02* (2013.01); *A61B 18/18* (2013.01); *A61B 2018/00434* (2013.01)

(56) References Cited

U.S. PATENT DOCUMENTS

| | | | |
|---|---|---|---|
| 1,207,479 | A | 12/1916 | Bisgaard |
| 1,216,183 | A | 2/1917 | Swingle |
| 2,072,346 | A | 3/1937 | Smith |
| 3,320,957 | A | 5/1967 | Sokolik |
| 3,568,659 | A | 3/1971 | Karnegis |
| 3,667,476 | A | 6/1972 | Muller |
| 3,692,029 | A | 9/1972 | Adair |
| 3,995,617 | A | 12/1976 | Watkins et al. |
| 4,095,602 | A | 6/1978 | Leveen |
| 4,116,589 | A | 9/1978 | Rishton |
| 4,129,129 | A | 12/1978 | Amrine |
| 4,154,246 | A | 5/1979 | LeVeen |
| 4,461,283 | A | 7/1984 | Doi |
| 4,502,490 | A | 3/1985 | Evans et al. |
| 4,503,855 | A | 3/1985 | Maslanka |
| 4,512,762 | A | 4/1985 | Spears |
| 4,522,212 | A | 6/1985 | Gelinas et al. |
| 4,557,272 | A | 12/1985 | Carr |
| 4,565,200 | A | 1/1986 | Cosman |
| 4,567,882 | A | 2/1986 | Heller |
| 4,584,998 | A | 4/1986 | McGrail |
| 4,612,934 | A | 9/1986 | Borkan |
| 4,621,642 | A | 11/1986 | Chen |
| 4,621,882 | A | 11/1986 | Krumme |
| 4,625,712 | A | 12/1986 | Wampler |
| 4,643,186 | A | 2/1987 | Rosen et al. |
| 4,646,737 | A | 3/1987 | Hussein et al. |
| 4,674,497 | A | 6/1987 | Ogasawara |
| 4,683,890 | A | 8/1987 | Hewson |
| 4,704,121 | A | 11/1987 | Moise |
| 4,706,688 | A | 11/1987 | Don Michael et al. |
| 4,709,698 | A | 12/1987 | Johnston et al. |
| 4,739,759 | A | 4/1988 | Rexroth et al. |
| 4,754,065 | A | 6/1988 | Levenson et al. |
| 4,754,752 | A | 7/1988 | Ginsburg et al. |
| 4,765,959 | A | 8/1988 | Fukasawa |
| 4,773,899 | A | 9/1988 | Spears |
| 4,779,614 | A | 10/1988 | Moise |
| 4,784,135 | A | 11/1988 | Blum et al. |
| 4,790,305 | A | 12/1988 | Zoltan et al. |
| 4,799,479 | A | 1/1989 | Spears |
| 4,802,492 | A | 2/1989 | Grunstein |
| 4,817,586 | A | 4/1989 | Wampler |
| 4,825,871 | A | 5/1989 | Cansell |
| 4,827,935 | A | 5/1989 | Geddes et al. |
| 4,846,152 | A | 7/1989 | Wampler et al. |
| 4,862,886 | A | 9/1989 | Clarke et al. |
| 4,895,557 | A | 1/1990 | Moise et al. |
| 4,906,229 | A | 3/1990 | Wampler |
| 4,907,589 | A | 3/1990 | Cosman |
| 4,908,012 | A | 3/1990 | Moise et al. |
| 4,920,978 | A | 5/1990 | Colvin |
| 4,944,722 | A | 7/1990 | Carriker et al. |
| 4,955,377 | A | 9/1990 | Lennox et al. |
| 4,967,765 | A | 11/1990 | Turner et al. |
| 4,969,865 | A | 11/1990 | Hwang et al. |
| 4,976,709 | A | 12/1990 | Sand |
| 4,985,014 | A | 1/1991 | Orejola |
| 4,991,603 | A | 2/1991 | Cohen et al. |
| 5,009,636 | A | 4/1991 | Wortley et al. |
| 5,009,936 | A | 4/1991 | Yamanaka et al. |
| 5,010,892 | A | 4/1991 | Colvin et al. |
| 5,019,075 | A | 5/1991 | Spears et al. |
| 5,027,829 | A | 7/1991 | Larsen |
| 5,030,645 | A | 7/1991 | Kollonitsch |
| 5,036,848 | A | 8/1991 | Hewson |
| 5,053,033 | A | 10/1991 | Clarke |
| 5,056,519 | A | 10/1991 | Vince |
| 5,074,860 | A | 12/1991 | Gregory et al. |
| 5,078,716 | A | 1/1992 | Doll |
| 5,084,044 | A | 1/1992 | Quint |
| 5,096,916 | A | 3/1992 | Skupin |
| 5,100,388 | A | 3/1992 | Behl et al. |
| 5,100,423 | A | 3/1992 | Fearnot |
| 5,103,804 | A | 4/1992 | Abele et al. |
| 5,105,826 | A | 4/1992 | Smits et al. |
| 5,106,360 | A | 4/1992 | Ishiwara et al. |
| 5,107,830 | A | 4/1992 | Younes |
| 5,114,423 | A | 5/1992 | Kasprzyk et al. |
| 5,116,864 | A | 5/1992 | March et al. |
| 5,117,828 | A | 6/1992 | Metzger et al. |
| 5,135,517 | A | 8/1992 | McCoy |
| 5,152,286 | A | 10/1992 | Sitko et al. |
| 5,165,420 | A | 11/1992 | Strickland |
| 5,167,223 | A | 12/1992 | Koros et al. |
| 5,170,803 | A | 12/1992 | Hewson et al. |
| 5,174,288 | A | 12/1992 | Bardy et al. |
| 5,188,602 | A | 2/1993 | Nichols |
| 5,191,883 | A | 3/1993 | Lennox et al. |
| 5,213,576 | A | 5/1993 | Abiuso et al. |
| 5,215,103 | A | 6/1993 | Desai |
| 5,231,996 | A | 8/1993 | Bardy et al. |
| 5,232,444 | A | 8/1993 | Just et al. |
| 5,234,456 | A | 8/1993 | Silvestrini |
| 5,254,088 | A | 10/1993 | Lundquist et al. |
| 5,255,678 | A | 10/1993 | Deslauriers et al. |
| 5,255,679 | A | 10/1993 | Imran |
| 5,265,604 | A | 11/1993 | Vince |
| 5,269,758 | A | 12/1993 | Taheri |
| 5,281,218 | A | 1/1994 | Imran |

(56) References Cited

U.S. PATENT DOCUMENTS

| | | |
|---|---|---|
| 5,292,331 A | 3/1994 | Boneau |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,703 A | 6/1995 | Feiring |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,660,175 A | 8/1997 | Dayal |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |

(56) References Cited

U.S. PATENT DOCUMENTS

| | | | |
|---|---|---|---|
| 5,881,727 | A | 3/1999 | Edwards |
| 5,882,346 | A | 3/1999 | Pomeranz et al. |
| 5,891,135 | A | 4/1999 | Jackson et al. |
| 5,891,136 | A | 4/1999 | McGee et al. |
| 5,891,138 | A | 4/1999 | Tu et al. |
| 5,893,847 | A | 4/1999 | Kordis |
| 5,897,554 | A | 4/1999 | Chia et al. |
| 5,899,882 | A | 5/1999 | Waksman et al. |
| 5,904,651 | A | 5/1999 | Swanson et al. |
| 5,904,711 | A | 5/1999 | Flom et al. |
| 5,906,636 | A | 5/1999 | Casscells, III et al. |
| 5,908,445 | A | 6/1999 | Whayne et al. |
| 5,908,446 | A | 6/1999 | Imran |
| 5,908,839 | A | 6/1999 | Levitt et al. |
| 5,911,218 | A | 6/1999 | DiMarco |
| 5,916,235 | A | 6/1999 | Guglielmi |
| 5,919,147 | A | 7/1999 | Jain |
| 5,919,172 | A | 7/1999 | Golba, Jr. |
| 5,924,424 | A | 7/1999 | Stevens et al. |
| 5,928,228 | A | 7/1999 | Kordis et al. |
| 5,931,835 | A | 8/1999 | Mackey |
| 5,935,079 | A | 8/1999 | Swanson et al. |
| 5,941,869 | A | 8/1999 | Patterson et al. |
| 5,951,494 | A | 9/1999 | Wang et al. |
| 5,951,546 | A | 9/1999 | Lorentzen |
| 5,954,661 | A | 9/1999 | Greenspon et al. |
| 5,954,662 | A | 9/1999 | Swanson et al. |
| 5,954,717 | A | 9/1999 | Behl et al. |
| 5,957,961 | A | 9/1999 | Maguire et al. |
| 5,964,753 | A | 10/1999 | Edwards |
| 5,964,796 | A | 10/1999 | Imran |
| 5,971,983 | A | 10/1999 | Lesh |
| 5,972,026 | A | 10/1999 | Laufer et al. |
| 5,976,175 | A | 11/1999 | Hirano et al. |
| 5,979,456 | A | 11/1999 | Magovern |
| 5,980,563 | A | 11/1999 | Tu et al. |
| 5,984,917 | A | 11/1999 | Fleischman et al. |
| 5,991,650 | A | 11/1999 | Swanson et al. |
| 5,992,419 | A | 11/1999 | Sterzer et al. |
| 5,993,462 | A | 11/1999 | Pomeranz et al. |
| 5,997,534 | A | 12/1999 | Tu et al. |
| 5,999,855 | A | 12/1999 | DiMarco |
| 6,001,054 | A | 12/1999 | Regula et al. |
| 6,003,517 | A | 12/1999 | Sheffield et al. |
| 6,004,269 | A | 12/1999 | Crowley et al. |
| 6,006,755 | A | 12/1999 | Edwards |
| 6,008,211 | A | 12/1999 | Robinson et al. |
| 6,009,877 | A | 1/2000 | Edwards |
| 6,010,500 | A | 1/2000 | Sherman et al. |
| 6,014,579 | A | 1/2000 | Pomeranz et al. |
| 6,016,437 | A | 1/2000 | Tu et al. |
| 6,023,638 | A | 2/2000 | Swanson |
| 6,024,740 | A | 2/2000 | Lesh et al. |
| 6,029,091 | A | 2/2000 | De La Rama et al. |
| 6,033,397 | A | 3/2000 | Laufer et al. |
| 6,036,687 | A | 3/2000 | Laufer et al. |
| 6,036,689 | A | 3/2000 | Tu et al. |
| 6,039,731 | A | 3/2000 | Taylor et al. |
| 6,045,549 | A | 4/2000 | Smethers et al. |
| 6,045,550 | A | 4/2000 | Simpson et al. |
| 6,050,992 | A | 4/2000 | Nichols |
| 6,053,172 | A | 4/2000 | Hovda et al. |
| 6,053,909 | A | 4/2000 | Shadduck |
| 6,056,744 | A | 5/2000 | Edwards |
| 6,056,769 | A | 5/2000 | Epstein et al. |
| 6,063,078 | A | 5/2000 | Wittkampf |
| 6,071,280 | A | 6/2000 | Edwards et al. |
| 6,071,281 | A | 6/2000 | Burnside et al. |
| 6,071,282 | A | 6/2000 | Fleischman |
| 6,083,255 | A | 7/2000 | Laufer et al. |
| 6,090,104 | A | 7/2000 | Webster, Jr. |
| 6,092,528 | A | 7/2000 | Edwards |
| 6,102,886 | A | 8/2000 | Lundquist et al. |
| 6,106,524 | A | 8/2000 | Eggers et al. |
| 6,123,702 | A | 9/2000 | Swanson et al. |
| 6,123,703 | A | 9/2000 | Tu et al. |
| 6,139,527 | A | 10/2000 | Laufer et al. |
| 6,139,571 | A | 10/2000 | Fuller et al. |
| 6,142,993 | A | 11/2000 | Whayne et al. |
| 6,143,013 | A | 11/2000 | Samson et al. |
| 6,149,647 | A | 11/2000 | Tu et al. |
| 6,152,143 | A | 11/2000 | Edwards |
| 6,152,899 | A | 11/2000 | Farley et al. |
| 6,159,194 | A | 12/2000 | Eggers et al. |
| 6,179,833 | B1 | 1/2001 | Taylor |
| 6,183,468 | B1 | 2/2001 | Swanson et al. |
| 6,198,970 | B1 | 3/2001 | Freed et al. |
| 6,200,311 | B1 | 3/2001 | Danek et al. |
| 6,200,332 | B1 | 3/2001 | Del Giglio |
| 6,200,333 | B1 | 3/2001 | Laufer |
| 6,210,367 | B1 | 4/2001 | Carr |
| 6,212,433 | B1 | 4/2001 | Behl |
| 6,214,002 | B1 | 4/2001 | Fleischman et al. |
| 6,216,043 | B1 | 4/2001 | Swanson et al. |
| 6,216,044 | B1 | 4/2001 | Kordis |
| 6,217,576 | B1 | 4/2001 | Tu et al. |
| 6,235,024 | B1 | 5/2001 | Tu |
| 6,241,727 | B1 | 6/2001 | Tu et al. |
| 6,245,065 | B1 | 6/2001 | Panescu et al. |
| 6,254,598 | B1 | 7/2001 | Edwards et al. |
| 6,258,087 | B1 | 7/2001 | Edwards et al. |
| 6,264,653 | B1 | 7/2001 | Falwell |
| 6,269,813 | B1 | 8/2001 | Fitzgerald et al. |
| 6,270,476 | B1 | 8/2001 | Santoianni et al. |
| 6,273,907 | B1 | 8/2001 | Laufer |
| 6,283,988 | B1 | 9/2001 | Laufer et al. |
| 6,283,989 | B1 | 9/2001 | Laufer et al. |
| 6,287,304 | B1 | 9/2001 | Eggers et al. |
| 6,296,639 | B1 | 10/2001 | Truckai et al. |
| 6,299,633 | B1 | 10/2001 | Laufer |
| 6,322,559 | B1 | 11/2001 | Daulton et al. |
| 6,322,584 | B2 | 11/2001 | Ingle et al. |
| 6,338,727 | B1 | 1/2002 | Noda et al. |
| 6,338,836 | B1 | 1/2002 | Kuth et al. |
| 6,346,104 | B2 | 2/2002 | Daly et al. |
| 6,355,031 | B1 | 3/2002 | Edwards et al. |
| 6,379,352 | B1 | 4/2002 | Reynolds et al. |
| 6,409,723 | B1 | 6/2002 | Edwards |
| 6,411,852 | B1 | 6/2002 | Danek et al. |
| 6,416,511 | B1 | 7/2002 | Lesh et al. |
| 6,416,740 | B1 | 7/2002 | Unger |
| 6,425,895 | B1 | 7/2002 | Swanson et al. |
| 6,440,129 | B1 | 8/2002 | Simpson |
| 6,442,435 | B2 | 8/2002 | King et al. |
| 6,458,121 | B1 | 10/2002 | Rosenstock et al. |
| 6,460,545 | B2 | 10/2002 | Kordis |
| 6,488,673 | B1 | 12/2002 | Laufer et al. |
| 6,488,679 | B1 | 12/2002 | Swanson et al. |
| 6,493,589 | B1 | 12/2002 | Medhkour et al. |
| 6,494,880 | B1 | 12/2002 | Swanson et al. |
| 6,496,738 | B2 | 12/2002 | Carr |
| 6,514,246 | B1 | 2/2003 | Swanson et al. |
| 6,526,320 | B2 | 2/2003 | Mitchell |
| 6,529,756 | B1 | 3/2003 | Phan et al. |
| 6,544,226 | B1 | 4/2003 | Gaiser et al. |
| 6,544,262 | B2 | 4/2003 | Fleischman |
| 6,547,788 | B1 | 4/2003 | Maguire et al. |
| 6,558,378 | B2 | 5/2003 | Sherman et al. |
| 6,572,612 | B2 | 6/2003 | Stewart et al. |
| 6,575,623 | B2 | 6/2003 | Werneth |
| 6,575,969 | B1 | 6/2003 | Rittman, III et al. |
| 6,582,427 | B1 | 6/2003 | Goble et al. |
| 6,582,430 | B2 | 6/2003 | Hall |
| 6,589,235 | B2 | 7/2003 | Wong et al. |
| 6,610,054 | B1 | 8/2003 | Edwards et al. |
| 6,620,159 | B2 | 9/2003 | Hegde |
| 6,626,903 | B2 | 9/2003 | McGuckin, Jr. et al. |
| 6,634,363 | B1 | 10/2003 | Danek et al. |
| 6,635,056 | B2 | 10/2003 | Kadhiresan et al. |
| 6,638,273 | B1 | 10/2003 | Farley et al. |
| 6,640,120 | B1 | 10/2003 | Swanson et al. |
| 6,645,200 | B1 | 11/2003 | Koblish et al. |
| 6,652,548 | B2 | 11/2003 | Evans et al. |
| 6,669,693 | B2 | 12/2003 | Friedman |

(56) References Cited

U.S. PATENT DOCUMENTS

| | | |
|---|---|---|
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,425,212 B1 | 9/2008 | Danek et al. |
| 7,542,802 B2 | 6/2009 | Biggs et al. |
| 7,556,624 B2 | 7/2009 | Laufer et al. |
| 7,740,017 B2 * | 6/2010 | Danek et al. .................. 128/898 |
| 7,770,584 B2 | 8/2010 | Danek et al. |
| 8,088,127 B2 * | 1/2012 | Mayse et al. .................. 606/41 |
| 8,161,978 B2 * | 4/2012 | Danek et al. .................. 128/898 |
| 8,172,827 B2 | 5/2012 | Deem et al. |
| 8,226,638 B2 | 7/2012 | Mayse et al. |
| 8,640,711 B2 * | 2/2014 | Danek et al. .................. 128/898 |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0187430 A1 | 10/2003 | Vorisek |
| 2003/0236455 A1 | 12/2003 | Swanson et al. |
| 2004/0049175 A1 | 3/2004 | Speck et al. |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106339 A1 | 5/2007 | Errico et al. |
| 2007/0106348 A1 | 5/2007 | Laufer |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2007/0162085 A1 | 7/2007 | DiLorenzo |
| 2008/0004596 A1 | 1/2008 | Yun et al. |
| 2008/0097424 A1 | 4/2008 | Wizeman et al. |
| 2008/0132886 A1 | 6/2008 | Cohen et al. |
| 2008/0255642 A1 | 10/2008 | Zarins et al. |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0143705 A1 | 6/2009 | Danek et al. |
| 2009/0143776 A1 | 6/2009 | Danek et al. |
| 2009/0163906 A1 * | 6/2009 | Faure .................. 606/34 |
| 2009/0192505 A1 | 7/2009 | Askew et al. |
| 2009/0192508 A1 | 7/2009 | Laufer et al. |
| 2009/0306644 A1 | 12/2009 | Mayse et al. |
| 2010/0160906 A1 | 6/2010 | Jarrard |
| 2010/0204689 A1 | 8/2010 | Danek et al. |
| 2011/0118725 A1 | 5/2011 | Mayse et al. |
| 2011/0152855 A1 | 6/2011 | Mayse et al. |
| 2011/0257647 A1 | 10/2011 | Mayse et al. |

FOREIGN PATENT DOCUMENTS

| | | |
|---|---|---|
| EP | 286145 A2 | 10/1988 |
| EP | 280225 A3 | 3/1989 |
| EP | 286145 A3 | 10/1990 |
| EP | 282225 B1 | 6/1992 |
| EP | 908713 A1 | 4/1999 |
| EP | 908150 B1 | 5/2003 |
| EP | 768091 B1 | 7/2003 |
| EP | 1297795 B1 | 8/2005 |
| FR | 2659240 B1 | 7/1997 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | 8911311 A1 | 11/1989 |
| WO | 9502370 A3 | 3/1995 |
| WO | 9510322 A1 | 4/1995 |
| WO | 9604860 A1 | 2/1996 |
| WO | 9610961 A1 | 4/1996 |
| WO | 9732532 A1 | 9/1997 |
| WO | 9733715 A1 | 9/1997 |
| WO | 9737715 A1 | 10/1997 |
| WO | 9740751 A1 | 11/1997 |
| WO | 9844854 A1 | 10/1998 |
| WO | 9852480 A1 | 11/1998 |
| WO | 9856324 A1 | 12/1998 |
| WO | 9903413 A1 | 1/1999 |
| WO | 9858681 A3 | 3/1999 |
| WO | 9913779 A2 | 3/1999 |
| WO | 9932040 A1 | 7/1999 |
| WO | 9934741 A1 | 7/1999 |
| WO | 9944506 A1 | 9/1999 |
| WO | 9945855 A1 | 9/1999 |

(56) References Cited

FOREIGN PATENT DOCUMENTS

| | | |
|---|---|---|
| WO | 9964109 A1 | 12/1999 |
| WO | 0051510 A1 | 9/2000 |
| WO | 0062699 A3 | 10/2000 |
| WO | 0103642 A1 | 1/2001 |
| WO | 0232333 A1 | 4/2002 |
| WO | 0232334 A1 | 4/2002 |
| WO | 2007053230 A2 | 5/2007 |
| WO | 2009082433 A2 | 7/2009 |
| WO | 2009137819 A1 | 11/2009 |
| WO | 2011056684 A2 | 5/2011 |
| WO | 2011060200 A1 | 5/2011 |
| WO | 2011060201 A1 | 5/2011 |
| WO | 2011127216 A2 | 10/2011 |

OTHER PUBLICATIONS

Awadh N., et al., "Airway wall thickness in patients with near fatal asthma and control groups: assessment with high resolution computed tomographic scanning," Thorax, 1998, 53, 248-253.
Bel E.H., ""Hot stuff": Bronchial Thermoplasty for Asthma," American Journal of Respiratory and Critical Care Medicine, 2006, 173 (9), 941-943.
Brown R.H., et al., "Effect of Bronchial Thermoplasty on Airway Distensibility," European Respiratory Journal, 2005, 26 (2), 277-282.
Brown R.H., et al., "In Vivo evaluation of the Effectiveness of Bronchial Thermoplasty with Computed Tomography," Journal of Applied Physiology, 2005, 98 (5), 1603-1606.
Chhajed P.N., et al., "Will there be a Role for Bronchoscopic Radiofrequency Ablation", Journal of Bronchology, 2005, 12 (3), 184-186.
Co-pending U.S. Appl. No. 09/095,323, filed Jun. 10, 1998.
Co-pending U.S. Appl. No. 09/244,173, filed Feb. 4, 1999.
Cox G., et al., "Asthma Control during the Year after Bronchial Thermoplasty," New England journal of medicine, 2007, 356 (13), 1327-1337.
Cox G., et al., "Asthma Intervention Research (AIR) Trial Evaluating Bronchial Thermoplasty: Early Results," American Thoracic Society Annual Meeting, 2002, 1 page.
Cox G., et al., "Bronchial Thermoplasty for Asthma," American Journal of Respiratory and Critical Care Medicine, 2006, 173 (9), 965-969.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," American Journal of Respiratory and Critical Care Medicine, 2004, 169, A313.
Cox G., et al., "Clinical Experience with Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma," American Thoracic Society Annual Meeting, 2002, 1068.
Cox G., et al., "Impact of Bronchial Thermoplasty on Asthma Status: Interim Results from the AIR Trial," 2006, 1 page.
Cox G., et al., "Radiofrequency Ablation of Airway Smooth Muscle for Sustained Treatment of Asthma: Preliminary Investigations," European Respiratory Journal, 2004, 24 (4), 659-663.
Danek C.J., et al., "Bronchial Thermoplasty Reduces Canine Airway Responsiveness to Local Methacholine Challenge," American Thoracic Society Annual Meeting, 2002, 1 page.
Danek C.J., et al., "Reduction in Airway Hyperresponsiveness to Methacholine by the Application of RF Energy in Dogs," Journal of Applied Physiology, 2004, 97 (5), 1946-1953.
Dierkesmann R., "Indication and Results of Endobronchial Laser Therapy," Lung, 1990, 168, 1095-1102.
Global Strategy for Asthma Management and Prevention, National Institute of Health, National Heart, Lung and Blood Institute, 2002, 192 pages.
Hogg J. C., "The Pathology of Asthma," APMIS, 1997, 105 (10), 735-745.
International Search Report for Application No. PCT/US00/05412, mailed on Jun. 20, 2000, 2 pages.
International Search Report for Application No. PCT/US00/18197, mailed on Oct. 3, 2000, 1 page.
International Search Report for Application No. PCT/US00/28745, mailed on Mar. 28, 2001, 6 pages.
International Search Report for Application No. PCT/US01/32321, mailed on Jan. 18, 2002, 2 pages.
International Search Report for Application No. PCT/US98/03759, mailed on Jul. 30, 1998, 1 page.
International Search Report for Application No. PCT/US98/26227, mailed on Mar. 25, 1999, 1 page.
International Search Report for Application No. PCT/US99/00232, mailed on Mar. 4, 1999, 1 page.
International Search Report for Application No. PCT/US99/12986, mailed on Sep. 29, 1999, 1 page.
Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
James A.L., et al., "The Mechanics of Airway Narrowing in Asthma," American Review of Respiratory Diseases, 1989, 139 (1), 242-246.
Janssen L.J., "Asthma Therapy: How Far have We Come, Why did We Fail and Where should We Go Next", European Respiratory Journal, 2009, 33 (1), 11-20.
Jeffery P.K, "Remodeling in Asthma and Chronic Obstructive Lung Disease," American Journal of Respiratory and Critical Care Medicine, 2001, 164 (10), S28-S38.
Johnson S. R., et al., "Synthetic Functions of Airway Smooth Muscle in Asthma," Trends Pharmacol. Sci., 1997, 18 (8), 288-292.
Kitamura S., "Color Atlas of Clinical Application of Fiberoptic Bronchoscopy," 1990, Year Book Medical Publishers, 2 pages.
Kraft M., "The Distal Airways: Are they Important in Asthma", European Respiratory Journal, 1999, 14 (6), 1403-1417.
Laviolette M., et al., "Asthma Intervention Research (Air) Trial: Early Safety Assessment of Bronchial Thermoplasty," American Journal of Respiratory and Critical Care Medicine, 2004, 169, A314.
Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.
Lim E.C., et al., "Botulinum Toxin: A Novel Therapeutic Option for Bronchial Asthma", Medical Hypotheses, 2006, 66 (5), 915-919.
Lombard C.M., et al., "Histologic Effects of Bronchial Thermoplasty of Canine and Human Airways,"American Thoracic Society Annual Meeting, 2002, 1 page.
Macklem P. T., "Mechanical Factors Determining Maximum Bronchoconstriction," European Respiratory Journal, 1989, 6, 516s-519s.
Martin N., et al, "Bronchial Thermoplasty for the Treatment of Asthma," Current Allergy and Asthma Reports, 2009, 9 (1), 88-95.
Mayse M.L., et al., "Clinical Pearls for Bronchial Thermoplasty," Journal of Bronchology, 2007, 14 (2), 115-123.
Miller J.D., et al., "A Prospective Feasibility Study of Bronchial Thermoplasty in the Human Airway," Chest, 2005, 127 (6), 1999-2006.
Miller J.D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle the Appendix of the Lung," American Journal of Respiratory and Critical Care Medicine, 2004, 169 (7), 787-790.
Mitzner W., "Bronchial Thermoplasty in Asthma," Allergology International, 2006, 55 (3), 225-234.
Netter F.H., "Respiratory System: A Compilation of Paintings Depicting Anatomy and Embryology, Physiology, Pathology, Pathophysiology, and Clinical Features and Treatment of Diseases,In the CIBA Collection of Medical Illustrations M.B. Divertie, ed., Summit: New Jerse," 1979, 7, 119-135.
Notice of final Rejection, Japanese Patent Application No. 2000-553172, dated Sep. 2, 2008, 5 pages.

(56) References Cited

OTHER PUBLICATIONS

Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.

Rubin A., et al., "Bronchial Thermoplasty Improves Asthma Status of Moderate to Severe Perisstent Asthmatics Over and Above Current Standard-of-Care," American College of Chest Physicians, 2006, 2 pages.

Seow C.Y., et al., "Historical Perspective on Airway Smooth Muscle: The Saga of a Frustrated Cell," Journal of Applied Physiology, 2001, 91 (2), 938-952.

Shesterina M.V., et al., "Effect of Laser Therapy on Immunity in Patients with Bronchial Asthma and Pulmonary Tuberculosis," Problemy Tuberkuleza, 1994, 5, 23-26.

Shore S.A., "Airway Smooth Muscle in Asthma—Not Just More of the Same," New England Journal of Medicine, 2004, 351 (6), 531-532.

Solway J., et al., "Airway Smooth Muscle as a Target for Asthma Therapy," New England Journal of medicine, 2007, 356 (13), 1367-1369.

Sterk P.J., et al., "Heterogeneity of Airway Hyperresponsiveness: Time for Unconventional, But Traditional, Studies," Journal of Applied Physiology, 2004, 96 (6), 2017-2018.

Toma T.P., et al., "Brave New World for Interventional Bronchoscopy," Thorax, 2005, 60 (3), 180-181.

Trow T.K., "Clinical Year in Review I: Diagnostic Imaging, Asthma, Lung Transplantation, and Interventional Pulmonology," Proceedings of the American Thoracic Society, 2006, 3 (7), 553- 556.

UNSW Embryo-Respiratory System [online], Embryology, 2007, [retrieved on Dec. 10, 2007]. Retrieved from the internet: (URL:http://embryology.med.unsw.edu.au/Refer/respire/sclect.htm).

Vasilotta P.L., et al., "I-R Laser: A New Therapy in Rhino-Sino-Nasal Bronchial Syndrome with Asthmatic Component," American Society for Laser Medicine and Surgery Abstracts, 74. 1993.

Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.

Wiggs B.R., et al., "On the Mechanism of Mucosal Folding in Normal and Asthmatic Airways," Journal of Applied Physiology, 1997, 83 (6), 1814-1821.

Wilson S.R., et al., "Global Assessment after Bronchial Thermoplasty: The Patients Perspective," Journal of Outcomes Research, 2006, 10, 37-46.

Wizeman W., et al., "A Computer Model of Thermal Treatment of Airways by Radiofrequency (RF) Energy Delivery," American Thoracic Society Annual Meeting, 2007, 1 page.

\* cited by examiner

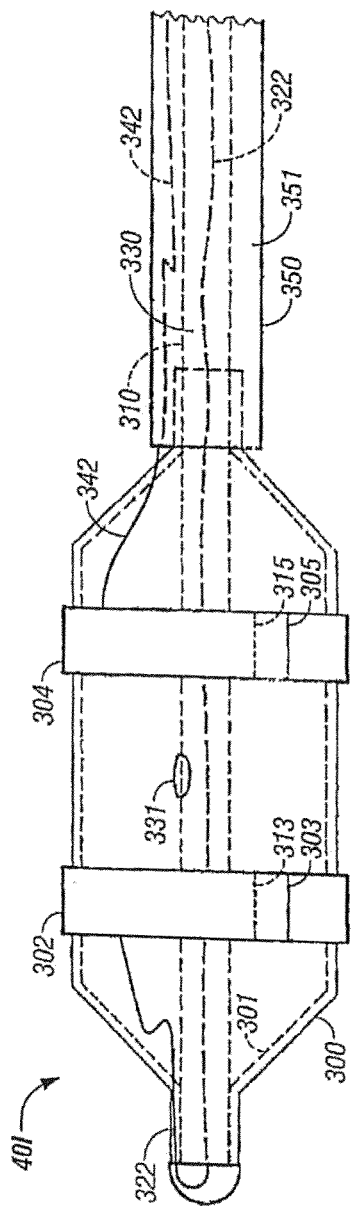
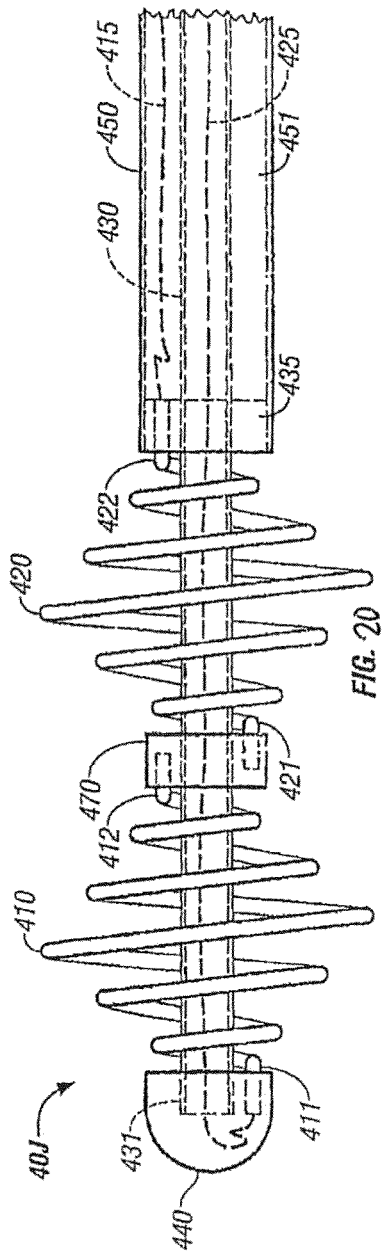

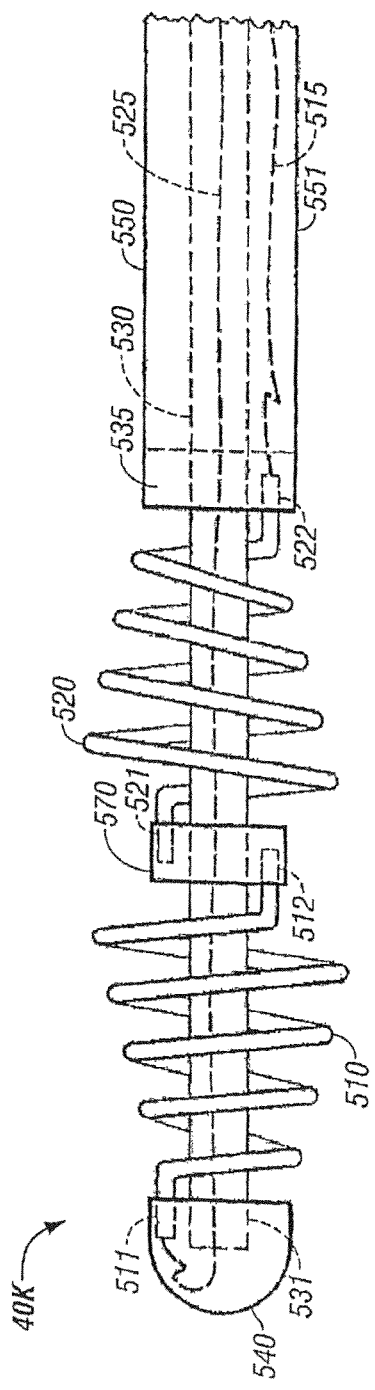
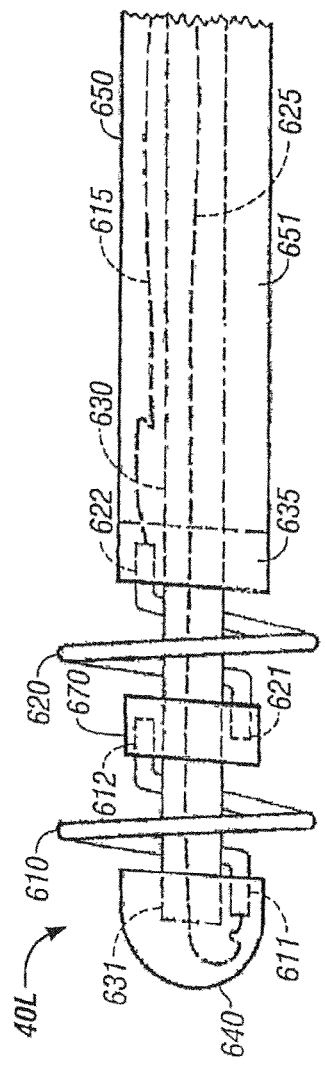
FIG. 21
FIG. 22

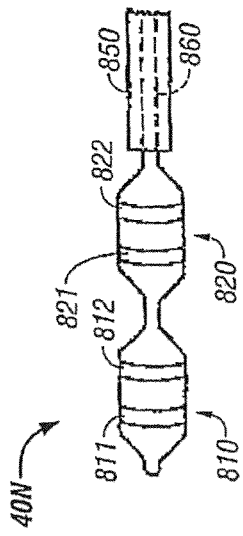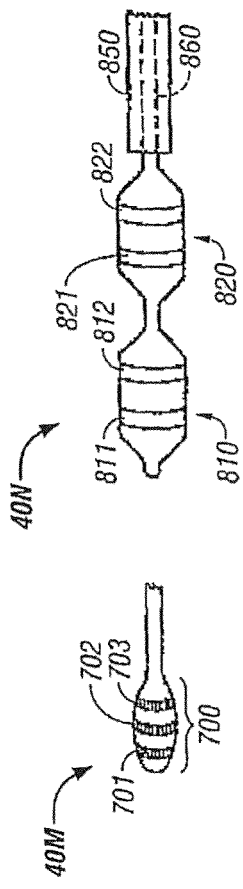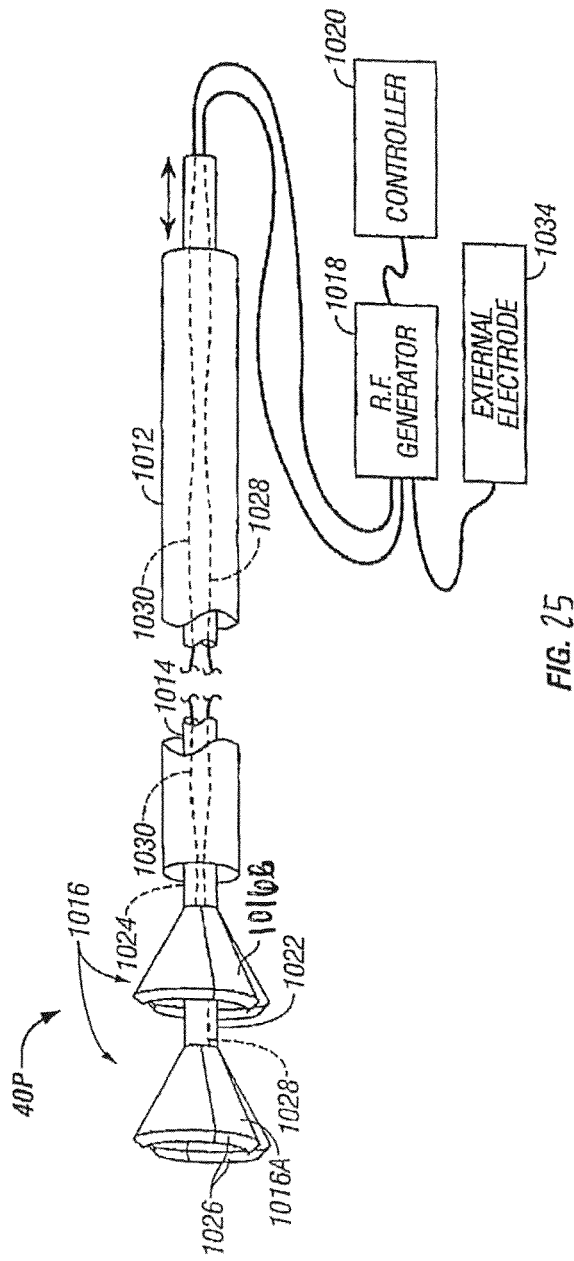

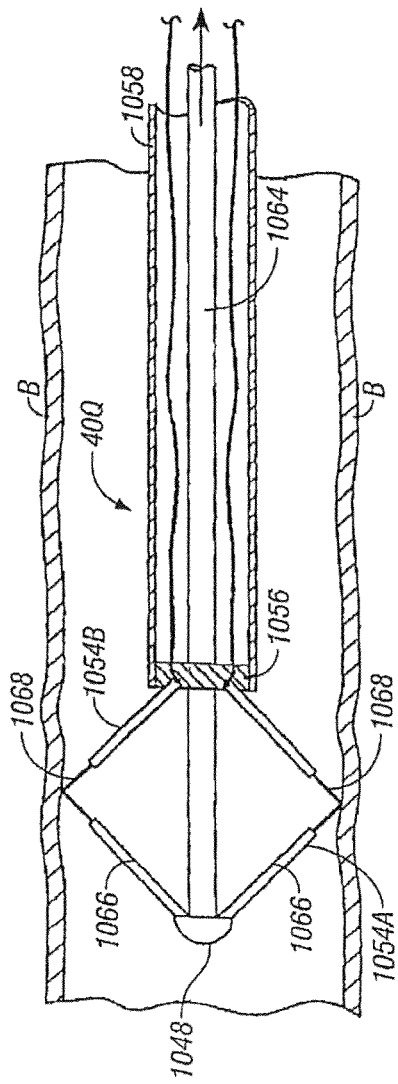
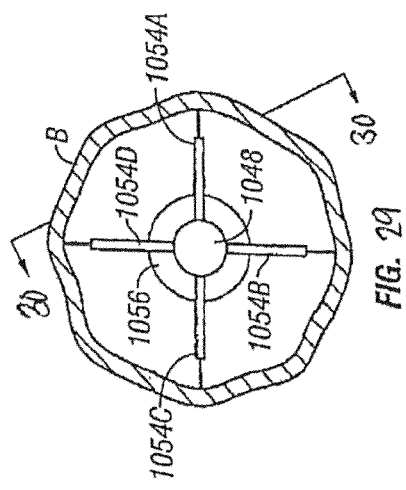

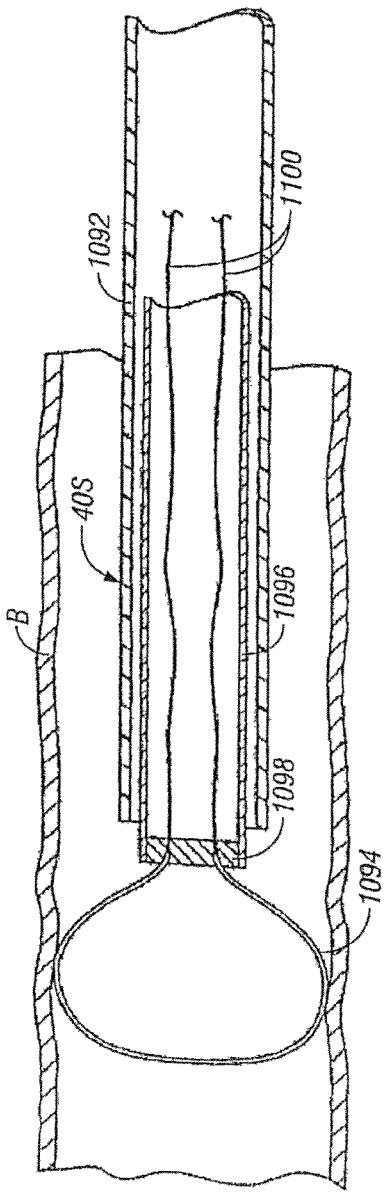
FIG. 32
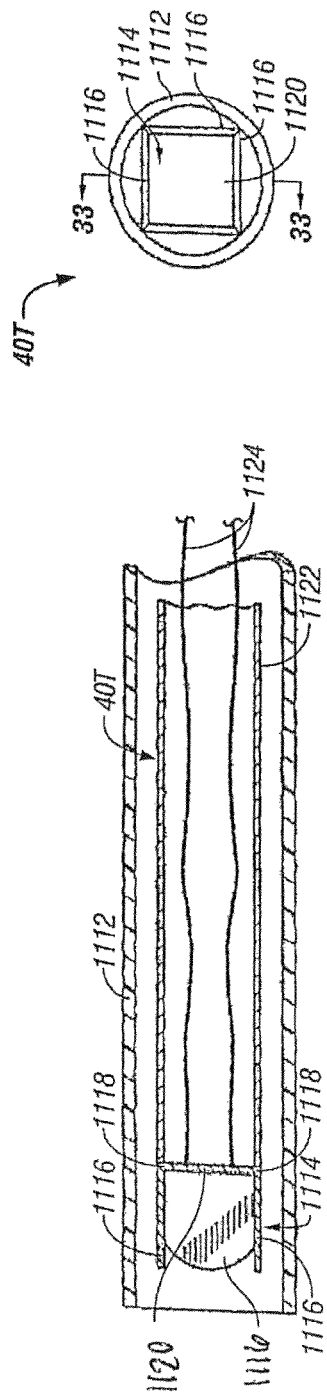
FIG. 34
FIG. 33

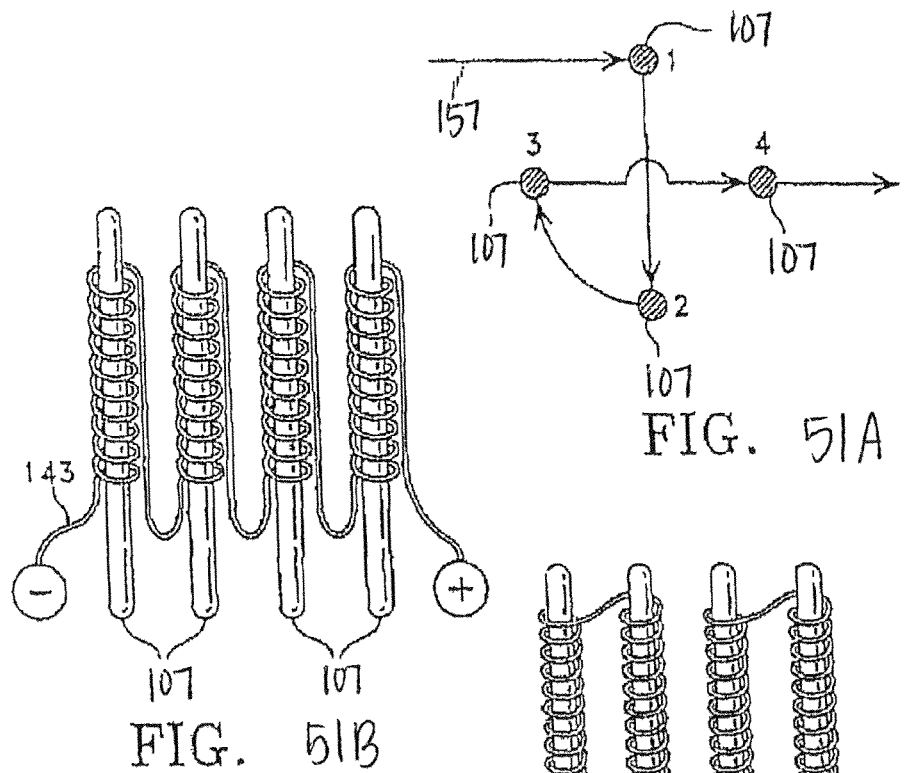
FIG. 51A
FIG. 51B
FIG. 51C
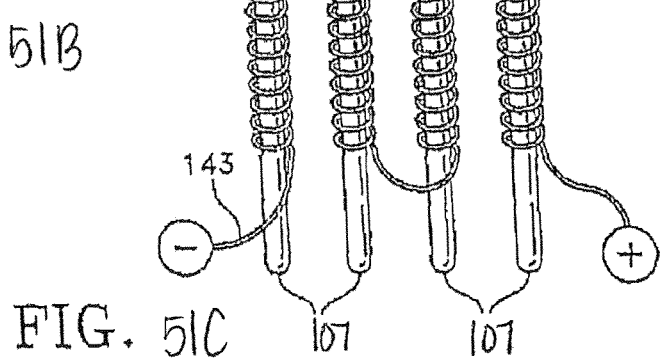
FIG. 51D
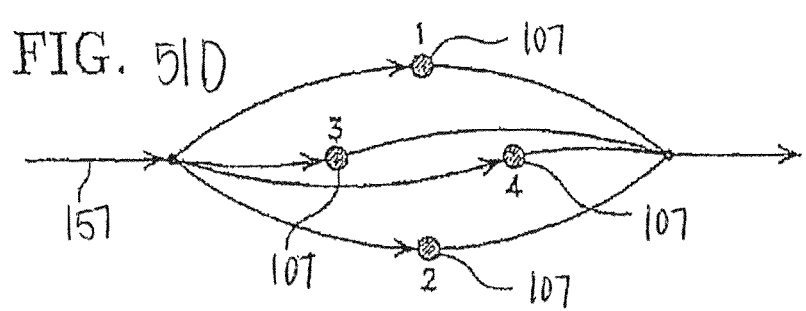

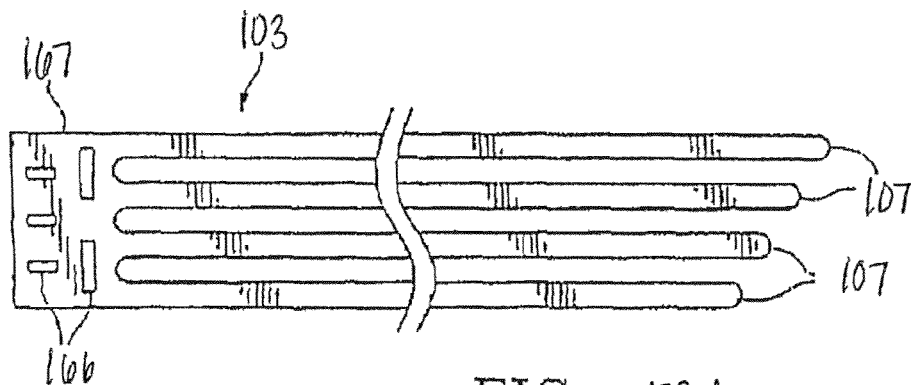
FIG. 53A
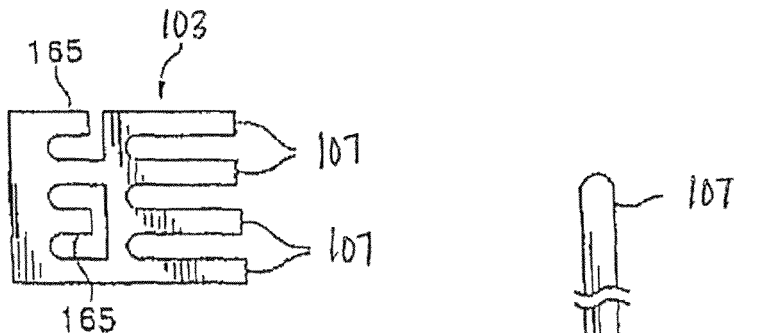
FIG. 53B
FIG. 53C
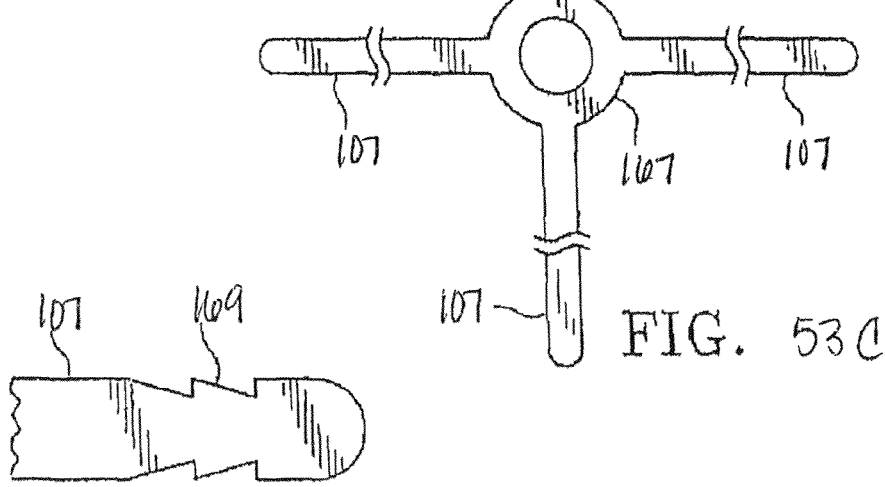
FIG. 53D

METHOD FOR TREATING A LUNG

CROSS REFERENCE TO RELATED APPLICATIONS

The present application is a continuation of U.S. patent application Ser. No. 12/964,678, filed Dec. 9, 2010, which is a continuation of U.S. patent application Ser. No. 12/727,156, filed Mar. 18, 2010, now U.S. Pat. No. 8,161,978, which is a continuation of U.S. patent application Ser. No. 11/117,905, filed Apr. 29, 2005, now U.S. Pat. No. 7,740,017, which is:

(a) a continuation application of U.S. patent application Ser. No. 09/999,851, filed Oct. 25, 2001, now U.S. Pat. No. 7,027,869, which is a continuation-in-part application of U.S. patent application Ser. No. 09/296,040, filed Apr. 21, 1999, now U.S. Pat. No. 6,411,852, each of which is herein incorporated by reference in its entirety;

(b) a continuation-in-part application of U.S. patent application Ser. No. 09/436,455, filed Nov. 8, 1999, now U.S. Pat. No. 7,425,212, which is incorporated by reference herein in its entirety; and (c) a continuation-in-part application of U.S. patent application Ser. No. 10/232,909, filed on Aug. 30, 2002, now U.S. Pat. No. 7,556,624, which is a continuation of U.S. patent application Ser. No. 09/349,715, filed Jul. 8, 1999, now U.S. Pat. No. 6,488,673, each of which is herein incorporated by reference in its entirety.

(d) U.S. patent application Ser. No. 09/999,851, now U.S. Pat. No. 7,027,869, is also a continuation-in-part application of U.S. patent application Ser. No. 09/535,856, filed on Mar. 27, 2000, now U.S. Pat. No. 6,634,363, which is also incorporated herein by reference in its entirety.

The present application is related to U.S. patent application Ser. No. 09/095,323 filed Jun. 10, 1998, now abandoned; U.S. patent application Ser. No. 09/260,401 filed on Mar. 1, 1999, now U.S. Pat. No. 6,283,988; U.S. patent application Ser. No. 09/003,750 filed Jan. 7, 1998, now U.S. Pat. No. 5,972,026; and U.S. patent application Ser. No. 08/833,550 filed Apr. 7, 1997, now U.S. Pat. No. 6,273,907 B1, the entireties of which are incorporated herein by reference.

BACKGROUND

Asthma is a serious chronic condition affecting an estimated 10 million Americans. Asthma is characterized by (i) bronchoconstriction, (ii) excessive mucus production, and (iii) inflammation and swelling of airways. These conditions cause widespread and variable airflow obstruction thereby making it difficult for the asthma sufferer to breathe. Asthma further includes acute episodes or attacks of additional airway narrowing via contraction of hyper-responsive airway smooth muscle. Other obstructive diseases such as COPD may also have a reversible component caused by one or more of the above mentioned three elements.

Asthma generally includes excessive mucus production in the bronchial tree. Usually, there is a general increase in bulk (hypertrophy) of the large bronchi and chronic inflammatory changes in the small airways. Excessive amounts of mucus are found in the airways and semisolid plugs of mucus may occlude some small bronchi. Also, the small airways are narrowed and show inflammatory changes. The reversible aspects of COPD include partial airway occlusion by excess secretions, and airway narrowing secondary to smooth muscle contraction, bronchial wall edema and inflammation of the airways.

In asthma, chronic inflammatory processes in the airway play a central role in increasing the resistance to airflow within the lungs. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Asthma is managed pharmacologically by: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management. Thus, current management techniques are neither completely successful nor free from side effects.

In view of the foregoing, a non-pharmacological asthma treatment which does not rely on avoiding stimuli is desirable.

SUMMARY OF THE INVENTION

The invention is a method for treating lung disease and in particular, a method for treating the lung during an acute episode of reversible obstructive pulmonary disease such as an asthma attack. One embodiment of the present invention includes a method for treating asthma comprising the step of transferring energy to an airway wall of an airway in a lung such that a diameter of the airway is increased. The energy may be transferred to the airway wall prior to, during or after an asthma attack. The energy may also be transferred in an amount sufficient to temporarily or permanently increase the effective diameter of the airway. The method may be performed while the airway is open, closed or partially closed.

In another embodiment of the invention, a method for treating asthma in a lung having a constricted airway comprises transferring energy to an airway wall of the constricted airway sufficient to open the airway. The energy transferred may be in an amount sufficient to permanently or temporarily open the constricted airway. The method may be performed to open a wholly constricted airway as well as a partly constricted airway.

In yet another variation of the invention, a method for treating lung disease comprises transferring energy to an airway wall to alter the airway wall in such a manner that a resistance to airflow of the airway is decreased. The method may be performed by transferring energy to increase the caliber of the airway. The airway wall may also be altered by decreasing a thickness of the airway wall. The energy may be transferred to the airway wall during an asthma attack.

In another variation of the invention, the method comprises manipulating a distal portion of an energy delivery apparatus to a first location along the airway prior to applying the energy. The energy delivering apparatus can include a rounded tip sufficiently flexible such that when the tip encounters a closed or partially closed airway, trauma to the airway is minimized. The energy is then applied to a discrete location while the distal portion of the energy delivery apparatus is stationary. The distal portion can then be moved to a new location and the process repeated until a number of discrete locations have been treated. In an alternative, the method comprises moving the distal portion of the energy delivery apparatus from the first location and applying energy while the distal portion is being moved in the airway.

In another variation of the present invention, a method comprises transferring energy to or from an airway wall to treat a lung disease such as asthma. The method may be carried out by inserting into the airway an apparatus having a cryogenic tip or other cooling means capable of transferring energy from the tissue, resulting in a desired condition such as a larger diameter airway.

In yet another variation of the invention, a combination of the above discussed techniques are carried out such that at one time, energy is applied while the distal portion of the energy delivery device is being moved and at another time, energy is applied when the distal portion of the apparatus is stationary.

BRIEF DESCRIPTION OF THE DRAWINGS

The invention will now be described in greater detail with reference to the various embodiments illustrated in the accompanying drawings wherein:

FIGS. 19A and 19B illustrate an embodiment of a heat treatment apparatus that employs electrodes positioned on the outer surface of a balloon for use with the methods of the present invention;

FIGS. 20, 21, and 22 show embodiments of the heat treatment apparatus that employ diametrically adjustable electrodes for use with the methods of the present invention;

FIG. 23 illustrates a heat treatment apparatus with multiple electrodes for use with the methods of the present invention;

FIG. 24 illustrates a heat treatment apparatus with multiple balloons for use with the methods of the present invention;

FIG. 25 is a schematic side view of one embodiment of a heat treatment apparatus that employs two collapsible and retractable electrodes for use with the methods of the present invention;

FIG. 28 is a side cross-sectional view of the device of FIG. 27 in an enlarged state within a bronchial tube;

FIG. 29 is a side cross-sectional view of an alternative embodiment of a heat treatment apparatus with four electrodes in an enlarged state within a bronchial tube for use with the methods of the present invention;

FIG. 32 is a side cross-sectional view of the apparatus of FIG. 31 with the electrode in an expanded state within a bronchial tube for use with the methods of the present invention;

FIG. 33 is a side cross-sectional view of an alternative embodiment of the invention with a plate shape electrode in a contracted state for use with the methods of the present invention;

FIG. 34 is an end view of the apparatus of FIG. 33 in the contracted state;

FIGS. 51A-51D illustrate a series and parallel wiring of legs of the basket;

FIGS. 53A-53D illustrate examples of a basket formed from a single sheet or piece of material.

DETAILED DESCRIPTION

This invention relates to methods for improving airflow through the airways of a lung having reversible obstructive pulmonary disease. In accordance with the invention an airway may be treated during an acute episode of reversible obstructive pulmonary disease such as an asthma attack. The invention comprises applying or transferring energy to an airway wall to increase the diameter of the airway or otherwise reduce resistance to airflow through the airway. The energy may be transferred in an amount sufficient to temporarily or permanently increase the diameter of the airway. Notably, the method may be performed while the airway is open, closed or partially closed. The inventive method thus can "rescue" an asthma sufferer during an acute asthma episode by increasing the diameter of a constricted airway.

Figure 1:
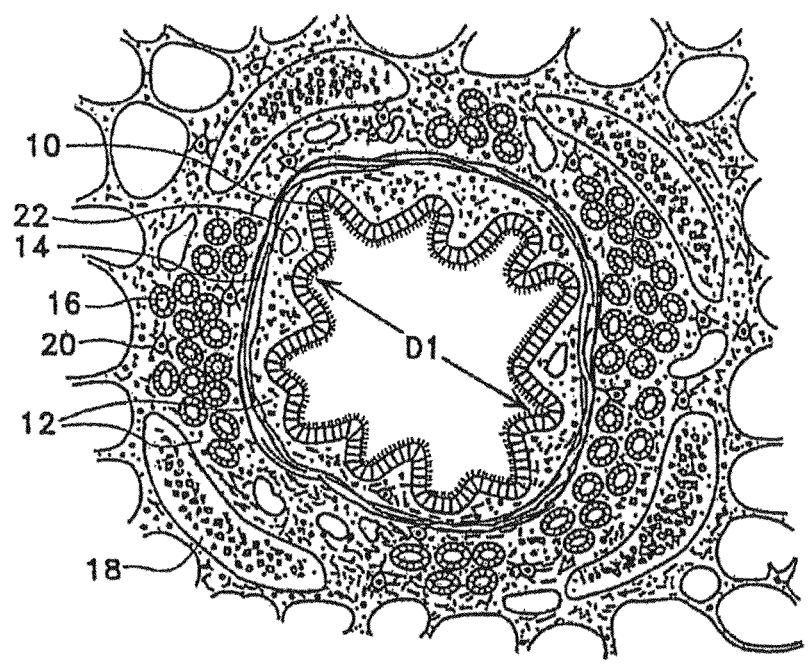
FIG. 1. Is a cross sectional view of an airway in a healthy lung.
Figure 2:
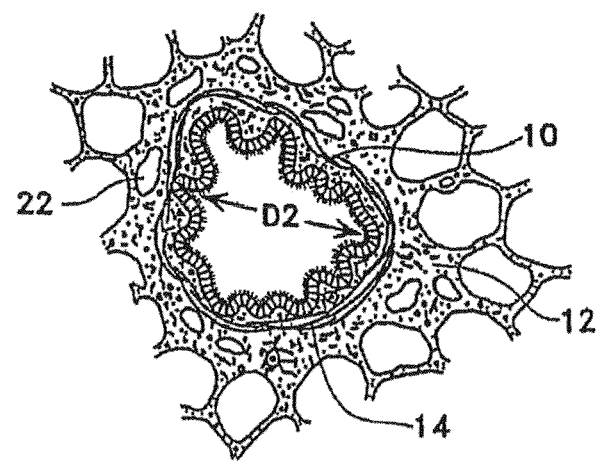
FIG. 2. Shows a section through a bronchiole having an airway diameter smaller than that shown in FIG. 1.
Figure 3:
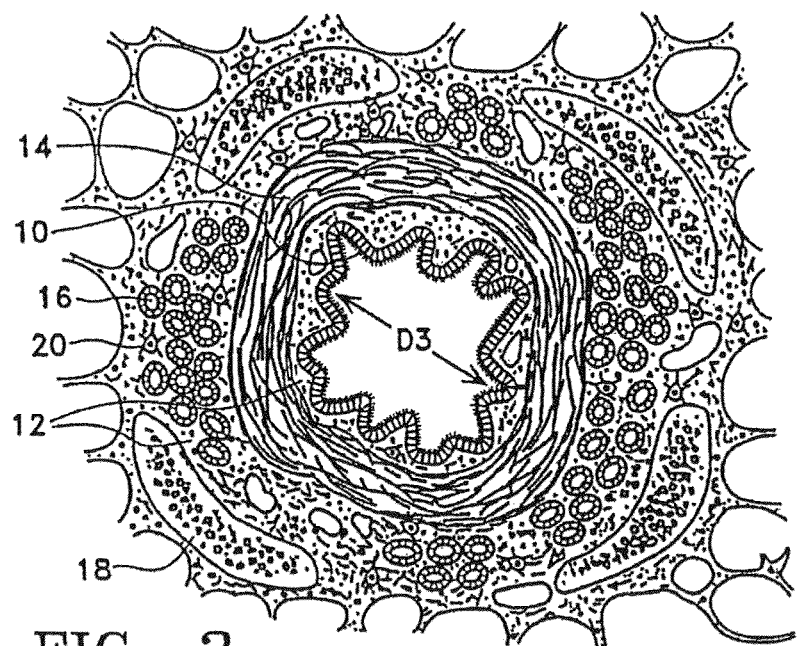
FIG. 3 illustrates the airway of FIG. 1 in which the smooth muscle has hypertrophied and increased in thickness causing reduction of the airway diameter.

Various airways are shown in FIGS. 1-3. FIGS. 1 and 2 show a cross section of two different airways in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 12 and smooth muscle tissue 14. The airway is thus quite different from other tissues such as blood vessel tissue which does not include such folds. The larger airways including the bronchus shown in FIG. 1 also have mucous glands 16 and cartilage 18 surrounding the smooth muscle tissue 14. Nerve fibers 20 and blood vessels 24 surround the airway.

FIG. 3 illustrates the bronchus of FIG. 1 in which the smooth muscle 14 has hypertrophied and increased in thickness causing the airway diameter to be reduced from the diameter D1 to a diameter D3. Accordingly, the airways to be treated with the device of the present invention may be 1 mm in diameter or greater. The airways to be treated are often second to eighth generation, and more preferably airways of the second to sixth generation.

Figure 4:
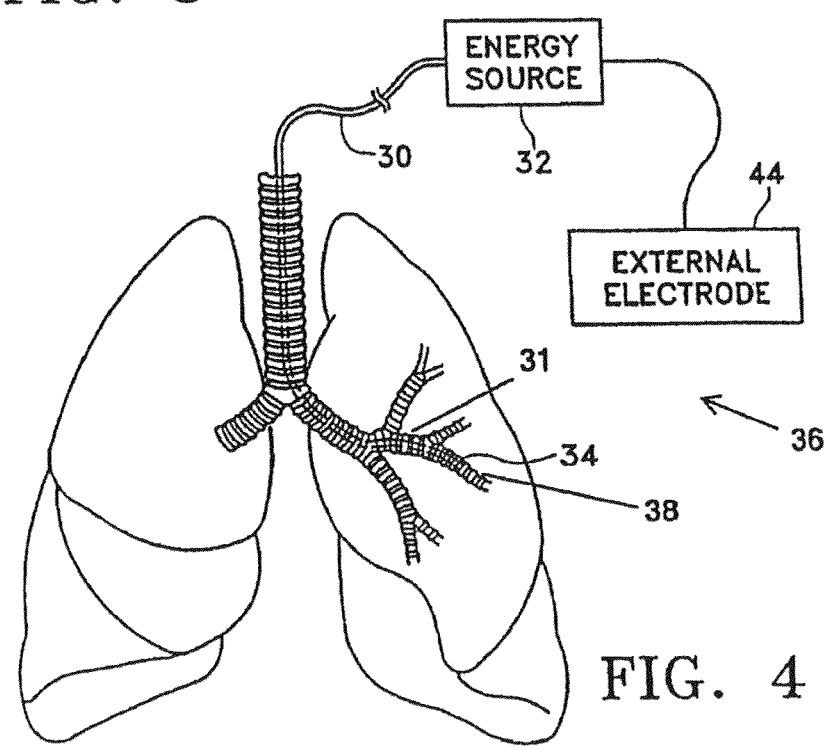
FIG. 4 is a schematic side view of the lungs being treated with a treatment device as described herein.

FIG. 4 is an illustration of the lungs being treated with a system 36 which can be used to carry out the present invention. The system 36 includes a controller 32 and an energy treatment device 30 which may be an elongated member as described further below. The device 30 also includes an expandable distal section which can be positioned at a treatment site 34 within a lung or another target medium. In operation, the device is manipulated to the treatment site 34. RF energy, for example, is delivered through the energy delivering device and penetrates the surface of the lung tissue such that tissue is affected below the epithelial layer as well as on the surface of the lung tissue. The application of energy may cause a variety of structural and physiological effects which may result from the application of energy to the airway wall. For example, application of energy to the airway smooth muscle of an asthmatic patient can debulk or otherwise reduce the volume of smooth muscle. This reduced volume of smooth muscle increases the airway diameter for improved air exchange. Even small increases in the airway size can provide relief as the resistance to airflow varies inversely with approximately the fourth power of diameter.

U.S. application Ser. No. 09/535,856, filed Mar. 27, 2000, and incorporated by reference in its entirety in the first paragraph of this application further describes that the ability of the airway to contract can also be altered by treatment of the smooth muscle in particular patterns. The smooth muscle is arranged around the airways in a generally helical pattern with pitch angles ranging from about −30 to about +30 degrees. Thus, the treatment of the smooth muscle in appropriate patterns interrupts or cuts through the helical pattern of the smooth muscle at a proper pitch and prevents the airway from constricting. This procedure of patterned treatment application eliminates contraction of the airways without completely eradicating smooth muscle and other airway tissue. A pattern for treatment may be chosen from a variety of patterns including longitudinal or axial stripes, circumferential bands, helical stripes, and the like as well as spot patterns having rectangular, elliptical, circular or other shapes. The size, number, and spacing of the treatment bands, stripes, or spots are chosen to provide a desired clinical effect of reduced airway responsiveness while limiting insult to the airway to a clinically acceptable level. The patterned treatment of the tissues surrounding the airways with energy provides various advantages. The careful selection of the portion of the airway to be treated allows desired results to be achieved while reducing the total healing load. Patterned treatment can also achieve desired results with decreased morbidity, preservation of epithelium, and preservation of a continuous or near continuous ciliated inner surface of the airway for mucociliary clearance. The pattern of treatment may also be chosen to achieve desired results while limiting total treatment area and/or the number of airways treated, thereby improving speed and ease of treatment.

Application of energy to an airway wall can also reduce inflammation in the inner lung tissue. Reducing inflammation and edema of the tissue surrounding the airway can increase the diameter of an airway. Inflammation and edema (accumulation of fluid) of the airway are chronic features of asthma. The inflammation and edema can be reduced by application of energy to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. The wound healing can also deposit collagen which improves parenchymal tethering.

Application of energy to an airway wall can also inhibit the release of inflammatory mediators in the airway wall which may serve as a stimulus for airway smooth muscle contraction. Therapy that reduces the production and release of inflammatory mediators can reduce smooth muscle contraction, inflammation of the airways, and edema. Examples of inflammatory mediators are cytokines, chemokines, and histamine. The tissues which produce and release inflammatory mediators include airway smooth muscle, epithelium, and mast cells. Thus, treatment of these structures with energy can reduce the ability of the airway structures to produce or release inflammatory mediators. The reduction in released inflammatory mediators will reduce chronic inflammation, thereby increasing the airway inner diameter, and may also reduce hyper-responsiveness of the airway smooth muscle.

Application of energy to an airway wall can also increase the airway diameter by damaging nerve tissue in the airways. This follows because a resting tone of smooth muscle is nerve regulated by release of catecholamines. Thus, by damaging or eliminating nerve tissue in the airways the resting tone of the smooth muscle is reduced, and the airway diameter is increased.

Application of energy to the airways may cause other physiological responses which result in increased diameters. It is to be understood, however, that the invention is not limited to a certain physiological response or process except where such a physiological response or process is a claim limitation in the appended claims.

As shown in FIG. 4, the present invention may be performed using a controller 32 and a device 30 through which it delivers energy to the target medium 34. A device 30 of the present invention should be of a size to access the bronchus or bronchioles of the human lung. The device may be sized to fit within bronchoscopes, preferably, with bronchoscopes having a working channel of 2 mm or less. The device may also include a steering member configured to guide the device to a desired target location. For example, this steering member may deflect a distal tip of the device in a desired direction to navigate to a desired bronchi or bronchiole.

Another aspect of the present invention is to treat more than one location. Several to many locations (e.g., reference numerals 31, 34, and 38) in the airways may be treated in order to reduce asthmatic symptoms. This can be accomplished by manipulating or positioning the expandable basket at a target site in the airways, expanding the expandable basket such that the energy transfer elements (e.g., the basket legs) contact the airway wall, and then delivering energy to the airway wall. The expandable basket is preferably collapsed and moved to another location and the process is repeated. This technique for applying energy at discrete locations can be repeated as many times as necessary to treat the asthmatic symptoms.

U.S. application Ser. No. 09/535,856, filed Mar. 27, 2000, and incorporated by reference in its entirety in the first paragraph of this application further describes that the invention may also include the additional step of reducing or stabilizing the temperature of lung tissue near to a treatment site. This may be accomplished for example, by injecting a cold fluid into lung parenchyma or into the airway being treated, where the airway is proximal, distal, or circumferentially adjacent to the treatment site. The fluid may be sterile normal saline, or any other bio-compatible fluid. The fluid may be injected into treatment regions within the lung while other regions of the lung normally ventilated by gas. Or, the fluid may be oxygenated to eliminate the need for alternate ventilation of the lung. Upon achieving the desired reduction or stabilization of temperature the fluid may be removed from the lungs. In the case where a gas is used to reduce temperature, the gas may be removed from the lung or allowed to be naturally exhaled. One benefit of reducing or stabilizing the temperature of the lung may be to prevent excessive destruction of the tissue, or to prevent destruction of certain types of tissue such as the epithelium, or to reduce the systemic healing load upon the patient's lung.

The present invention also includes applying energy continuously along an airway as an expanded basket is moved along the airway. Specifically, the basket may be deployed, energized, and then moved along the airway continuously to continually transfer energy to or from the airway wall as the basket is moved axially along the airway. The above described methods may also be used in combination with one another.

Figure 5:
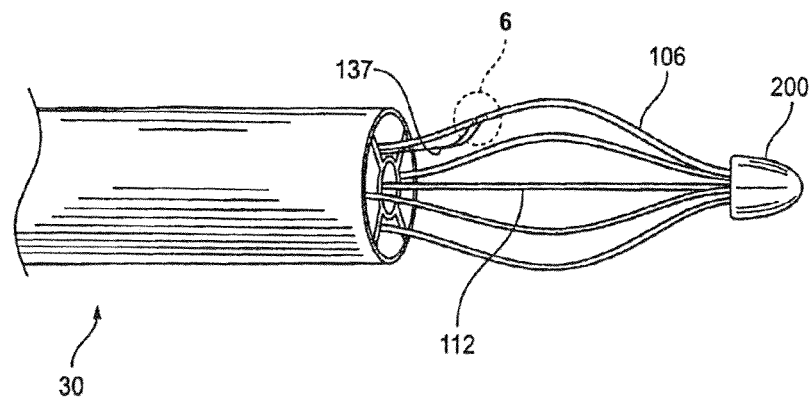
FIG. 5 is a partial view of an energy delivery device which can be used to carry out the method of the invention.

An exemplary partial view of an energy delivering device which may be used to perform the invention is shown in FIG. 5. The energy delivering apparatus 30 typically includes an elongate body having a proximal section and a distal section. The distal section features a radially expandable basket having a plurality of legs 106. The legs may be electrodes or have an active region defined by an insulated covering which contacts the medium to be treated. The basket is expanded with an actuator mechanism 112 which may be activated by a movable lever in a handle attached to the proximal end of the elongate body.

The invention may also include an atraumatic tip 200 to ensure that the invention does not injure airway tissue when it is placed into airways that are partially or completely closed. The tip may be formed of a flexible material and/or may be rounded to minimize trauma. Examples of energy delivering devices in accordance with the present invention are described in co-pending U.S. application Ser. No. 09/436,455 filed Nov. 8, 1999, which is hereby incorporated by reference in its entirety. Other examples of devices and methods which may be used in accordance with the present invention are found in the following U.S. patent application Ser. No. 09/095,323—Methods and Apparatus for Treating Smooth Muscles in the Walls of Body Conduits; Ser. No. 09/349,715—Method of Increasing Gas Exchange of a Lung; and Ser. No. 09/296,040—Devices for Modification of Airways By Transfer of Energy. The entirety of each of the aforementioned applications is hereby incorporated by reference. Another suitable energy device is described in International Patent Application No. PCT/US00/28745.

Examples of energy delivering devices disclosed in U.S. application Ser. Nos. 09/436,455 and 09/349,715, incorporated fully above, are now described immediately below in connection with FIGS. 7-48.

Figure 7:
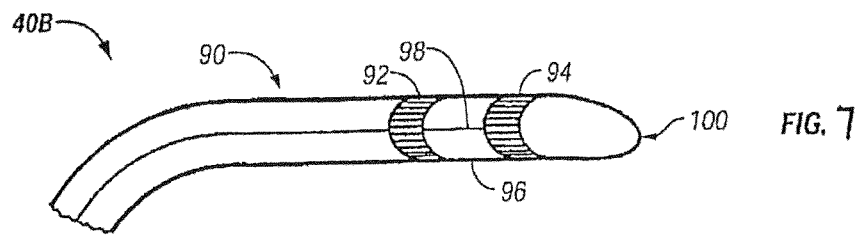
FIGS. 7, 8, 9A, 9B, 10A and 10B are perspective views of heat treatment apparatus for use with the methods of the present invention.

FIG. 7 illustrates another treatment apparatus 40B for use with one embodiment of the present invention. The treatment apparatus 40B includes an elongated, cylindrical member 90 having a heating element that has a plurality of electrodes designated 92 and 94 located on the outer surface of the member. The electrodes are electrically connected to a source of RF energy via connector 98. Preferably each electrode is configured as a band as shown that has a width of about 0.2 mm to about 3 mm, and preferably each electrode band is separate from the next by a distance of about 0.5 mm to 10 mm. The heating element may include one or more electrode bands. The treatment apparatus 40B has a distal end 100 that is rounded to reduce the amount of resistance encountered when the apparatus is advanced into the airway.

The apparatus 40B has an outer diameter that is approximately equal to (or can be expandable to equal) the desired final inner diameter of the lumen of an air passage to be treated. Typically, the outer diameter ranges from about 1.3 mm to about 7 mm. When the heating element comprises a plurality of electrode bands, the distance between each band is preferably less than about three times the outer diameter of the apparatus. The effect will be that the patency bands formed on the wall of the lumen by the electrodes 92, 94 will be separated from each other by no more than a distance equal to about three times the length of the outer diameter of the lumen. The patency bands so configured will provide good support for the airway to prevent the lumen from collapsing.

The treatment apparatus 40B applies a sufficient amount of energy to the walls of collapsible air passages to destroy airway smooth muscle tone and damage cells of the airway tissue to induce fibrosis and create a more rigid wall that can support a non-collapsed lumen. In this embodiment, energy emanates from the electrode bands 92, 94 so that following treatment with this particular apparatus, the walls of the air passage will develop patency bands corresponding to locations along the walls. The contours of the patency bans should substantially match those of the electrode bands. As is apparent, the number and width of each electrode band are not critical. In the case where there is only one electrode band, it may be necessary to move the apparatus and heat more than one area of the lumen wall in order to damage sufficient amounts of the airway wall to induce enough fibrosis to increase the strength of the airway wall such that it is no longer collapsed, i.e., the lumen remains substantially open during normal breathing.

When the treatment apparatus 40B is positioned at the treatment site, an RF generator is activated to provide suitable RF energy, preferably at a selected frequency in the range of 10 MHZ to 1000 MHZ. The emitted energy is converted within the tissue into heat in the range of about 40° C. to about 95° C.

RF energy is no longer applied after there has been damage to the tissue to induce a healing response. Preferably, the RF energy is applied for a length of time in the range of about 1 second to about 120 seconds. Suitable RF power sources are commercially available and well known to those skilled in the art. In one embodiment the RF generator employed has a single channel, delivering approximately 1 to 25 watts of RF energy and possessing continuous flow capability. The rate of transformation can be controlled by varying the energy delivered to the heating element.

Besides using RF energy for energizing the heating element, it is to be understood that other forms of energy such as alternating current, microwaves, ultrasound, and light (either coherent (e.g., laser) or incoherent (e.g., light emitting diode or tungsten filament) can be used), and that the thermal energy generated from a resistive coil, a hot fluid element (e.g., circulating liquids, gases, combinations of liquids and gases, etc.), a curie point element, or similar elements can be used as well. The hot fluid element may comprise, for example, an elongated member similar to the one illustrated in FIG. 7 that includes a conduit system whereby heated fluid is transported through the center of the member and then channeled outward toward the inner surface of the member. In one embodiment the heated fluid is diverted to contact the inner surface of the elongated member so that energy radiates from selected areas on the outer surface of the member corresponding to areas 92 and 94 in FIG. 7. Regardless of the source, energy delivered to the lumen wall of the obstructed airway passage should be such that all of the airway tissue is not completely ablated.

The heating element, as shown in FIG. 7, operates as a unipolar, internal electrode in the patient's body. An outer electrode (not shown) having a much larger surface area than that of the electrode bands is placed on the outer surface of the patient's body. For example, an external metal mesh or solid plate is placed on the skin with conductive gel. Both electrodes are connected to an RF generator which produces an electric field at a high frequency within the patient's body. Because the collective surface area of the electrode bands is much smaller than that of the outer electrode, the density of the high frequency electric field is much higher around the electrode bands. The electric field reaches its highest density between the two electrodes in the region near the heating element. The increased density of the field around the electrode bands produces localized heating of the tissue of the lumen wall.

Figure 8:
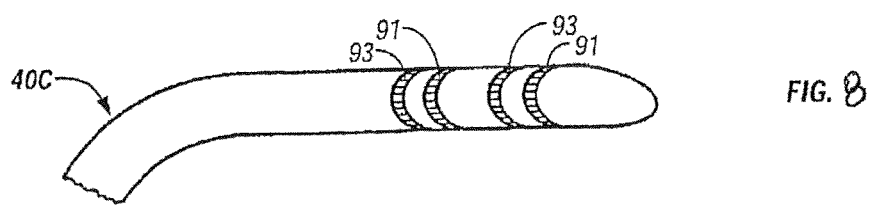

A heating element comprising a bipolar electrode can also be used. Referring to FIG. 7, in a bipolar arrangement electrode band 92 would be a first conductive element and electrode band 94 would be a second conductive element. The electrode bands emit RF energy with the first conductive element acting as the active electrode and the second conductive element acting as the return electrode, or vice versa. One electrode would be connected to the positive electrode of the generator and the other would be connected to the negative electrode. An insulator 96 is located between the conductive elements. FIG. 8 illustrates another treatment apparatus 40C for use with another embodiment of the present invention. The treatment apparatus 40C includes a heating element having multiple, i.e., double, bipolar electrode bands. Bands 91 are connected to the positive electrode of the RF generator and bands 93 are connected to the negative electrode. The material between the conductive elements are electrically insulated.

While the heating elements have been shown as electrode bands, other configurations can be used such as, for example, spiral, ring and grid patterns. These elements will create corresponding patterns on the lumen wall.

Figure 9A:
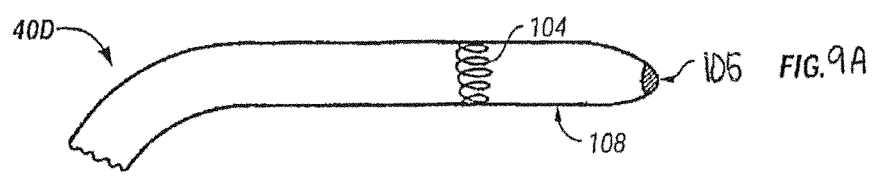

FIG. 9A illustrates another embodiment of the treatment apparatus 40D for use with another embodiment of the present invention. The treatment apparatus 40D includes an elongated, cylindrical member having a heating element that comprises electrodes 105 and 104 located on the other surface of the member. Preferably, the heating element comprises a bipolar electrode wherein one of the electrodes is the active electrode and the other electrode is the return electrode, or vice-versa. One electrode is connected to the RF positive electrode of the generator and the other is connected to the negative electrode. Segment 108 of the member situated between the electrodes is made of electrically insulating material.

Figure 9B:
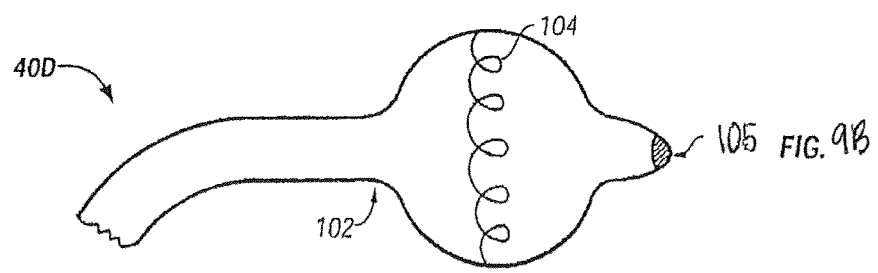
Figure 10A:
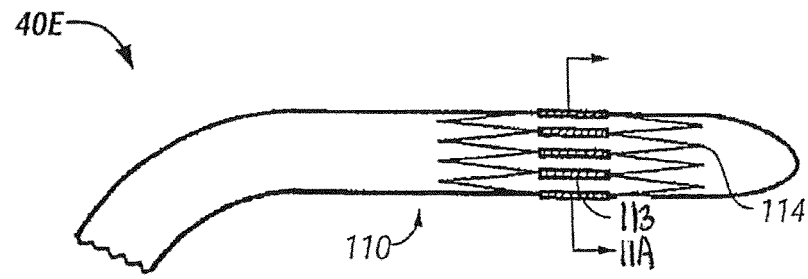
Figure 10B:
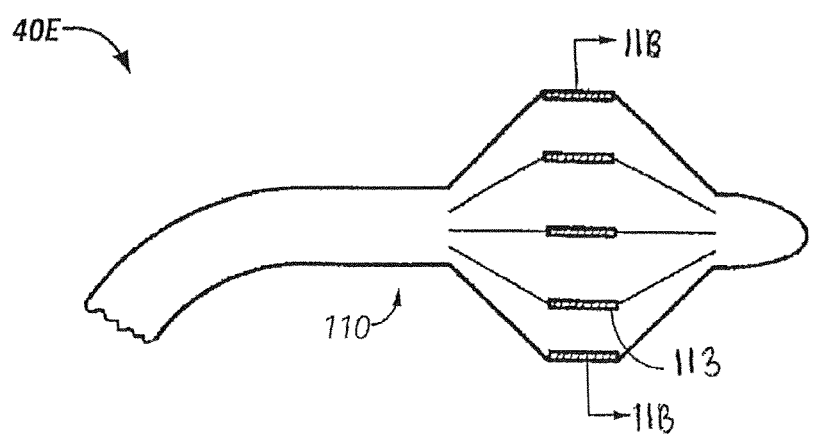

The segment of elongated member in and around electrode 104 is fabricated of material that is expandable and substantially impervious to air or other suitable gases for causing the elongated member to balloon. In this fashion, this section of the elongated member is radially expandable and deformable in response to compressed gas or any other suitable force or material that is applied into the interior region of the elongated member. Moreover, the elongated member will substantially return to its original, non-expanded form when the internal force is deactivated or the material is withdrawn. FIG. 9B illustrates the elongated member in the expanded position. The degree of expansion or distance that the member expands will depend on, among other things, the pressure applied and the elasticity of the member wall. In this embodiment, material between position 102 on the elongated member to the base of electrode 105 is fabricated from expandable material such as latex or polyethylene. The material selected preferably does not melt at the temperature ranges used in the treatment. Radial expansion causes electrode 104 to come into thermal or electrical contact with tissue of the air passage to be treated. Electrode 104 is preferably a spring coil. The treatment apparatus 40D may comprise more than one such coil electrode, which may be positioned along the length of the elongated member so that a plurality of locations along a bronchial tube can be treated simultaneously.

Figure 11A:
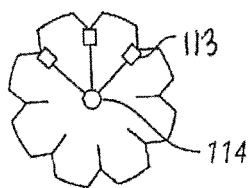
FIGS. 11A and 11B are cross-sectional views of heat treatment apparatus for use with the methods of the present invention.
Figure 11B:
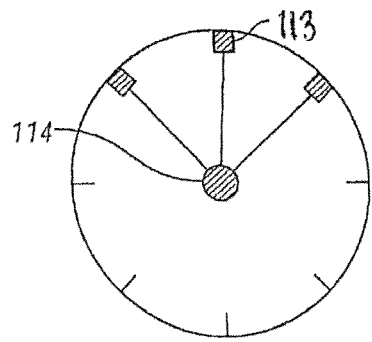

FIGS. 10A, 10B, 11A, and 11B illustrate a further embodiment of the treatment apparatus 40E for use with an embodiment of the present invention. The treatment apparatus 40E includes an elongated, cylindrical member 110 having one or more electrodes 113 situated on the outer surface of the elongated member. Preferably, a plurality of these electrodes form a number of rows of electrodes that are positioned along the length of the elongated member. As shown in cross sectional view FIG. 11A, the segment of surface of the elongated member at and around the electrodes is arranged in pleats 114. By being folded in this manner, the surface can expand radially when an outward force is applied from the interior of the cylindrical member as shown in FIGS. 11A and 11B. In this embodiment, the electrodes comprise non-ferrous (e.g., aluminum) strips and an electromagnet 114 which is positioned in the interior of the elongated member. When the electromagnet is energized with alternating current the magnetic field will cause the non-ferrous electrodes to repel from the electromagnet. In addition, the temperature of the electrode will rise due to Joule heating. The treatment apparatus may comprise a plurality of rows of the electrodes.

Figure 12A:
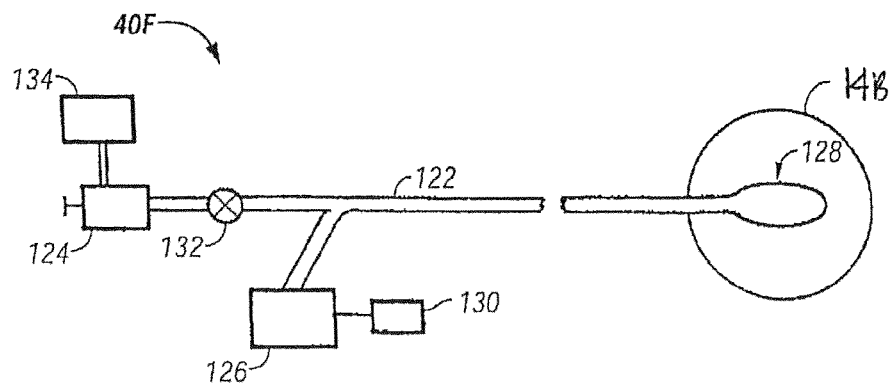
FIG. 12A is a schematic view of an embodiment of the treatment apparatus for use with the methods of the present invention.
Figure 12B:
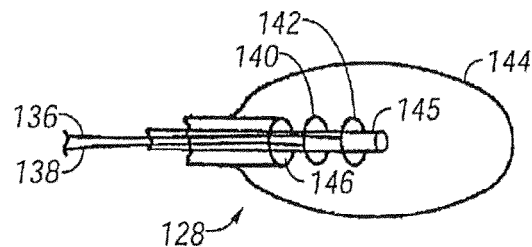
FIG. 12B is an enlarged view of the circled portion of FIG. 12A.

FIG. 12A illustrates another embodiment of a treatment apparatus 40F for use with another embodiment of the present invention. The treatment apparatus 40F includes a balloon 128 placed at the distal end of a catheter shaft 122. The catheter shaft is connected to syringe 124 located at the proximal end and is connected to an RF generator 126 in between the syringe and balloon. As shown in FIG. 12B which is an enlarged, cut away view of the device, the balloon 128, which is illustrated in the non-inflated state, is constructed of an elastomeric material 144. A preferred elastomeric material is silicone. Extending from lumen 146 of the shaft and into the interior of the balloon are electrodes 140 and 142 which are spaced apart and supported by rod 145. In this embodiment, each electrode is configured as a loop or ring around the rod. Catheter shafts suitable for use in the present invention are substantially any of the catheter shafts in current clinical use for surgical procedures. Balloons suitable for the present invention may be of similar material and design as those currently being used in percutaneous transluminal angioplasty. For a review of the state of the art, see U.S. Pat. Nos. 4,807,620; 5,057,106; 5,190,517; 5,281,218; 5,314,466; 5,370,677; 5,370,678; 5,405,346; 5,431,649; 5,437,664; 5,447,529; and 5,454,809. The inventive heat treatment apparatus will be described using balloons that are fabricated from an elastomeric material such as, for instance, silicone, natural latex, and polyethylene. The material selected preferably does not melt at the temperature ranges used in the treatment and is preferably impervious to the fluid used to inflate the balloon. With balloons that are made of elastomeric materials, the degree of expansion is proportional to the amount of force introduced into the interior of the balloon. Moreover, the balloon preferably will substantially return to its original, non-expanded form when the internal force is deactivated. When the balloon is fully expanded, its diameter will preferably be about 1 mm to 30 mm depending on the site to be treated. The balloon is typically attached to the catheter tip and the balloon material is folded or collapsed so that when it is fully inflated the balloon diameter has a fixed dimension. It is understood however that other balloon structures can be employed. For example, balloons made of nonelastic materials such as, for example, polyester (e.g., MYLAR) and polyethylene, can also be used. As is apparent, the balloon serves as a vessel or reservoir for medium that is heated. In the case where the electrodes are bipolar electrodes, the fluid (e.g., saline) between the poles acts as a resistive heating medium or resistive element. In addition, the balloon upon being inflated serves as structural support for the bronchial tubes.

Referring to FIGS. 12A and 12B, electrodes 140 and 142 are connected via cables 136 and 138, through the wall of the balloon 128, and through the catheter shaft 122 to a radio frequency (RF) generator 126 with controls 130. The catheter shaft 122 is also connected to the syringe 124 or other similar device for forcing a non-compressible fluid, such as saline, from source 134 through valve 132 to inflate the balloon with the fluid as the operating surgeon deems appropriate.

The frequency range of RF radiation useful in the present invention is typically about 10 KHZ to about 100 MHZ and preferably in the range of about 10 KHZ to about 800 KHZ. However, frequencies outside this range may be used at the discretion of the operating surgeon. Alternatively, microwave radiation typically in the frequency range of about 1,000 MHZ to about 2,000 MHZ, preferably in the range of about 1,100 MHZ to about 1,500 MHZ, may be used in place of RF radiation. However, as above, frequencies outside this range may be used at the discretion of the operating surgeon. The RF generator 126 may be replaced with a microwave generator, and the cables 136 and 138 replaced with a waveguide. Other modifications familiar to those skilled in the art may also be required. In addition, alternating current can be employed.

In use, when the operating surgeon has placed the treatment apparatus with the collapsed balloon within the lumen of a bronchial tube to be treated, the balloon is inflated through the catheter shaft 122 with fluid from the syringe 124 located conveniently for the surgeon. In the case where the lumen of the bronchial tube has collapsed or is partially collapsed, the balloon is preferably inflated until the lumen has expanded to its normal diameter with the balloon in substantial contact with the inner surface of the lumen. Alternatively, in the case where the lumen has not collapsed, the balloon is preferably inflated until it is in substantial contact with the inner surface of the lumen. Indeed, inflation of the balloon is not necessary in treating a non-collapsed bronchial lumen which has a diameter that is about equal to, or less than that of the outer surface of the uninflated balloon. As is apparent, even if the balloon does not have to be inflated, the balloon interior has fluid, e.g., electrically conductive saline, present which becomes heated by the application of RF energy.

Preferably, the exact amount of inflation is determined by the operating surgeon who monitors the balloon expansion by means of endoscopy, or other suitable imaging methods of the art. Generally, the heat required is induced in the tissue of the bronchial tube wall by the RF or microwave radiation emitting from the balloon tip.

FIGS. 13A, 13B, 14A, 14B, 15A, 15B, 16A, and 16B illustrate other embodiments of the electrode configurations which can be employed with the treatment apparatus 40F shown in FIG. 12A. In these figures, the balloons are shown in the inflated state containing fluid 151. The arrows depict the path of the electric field between the two electrodes or probes that serve as RF poles in the manners described above.

Figure 13A:
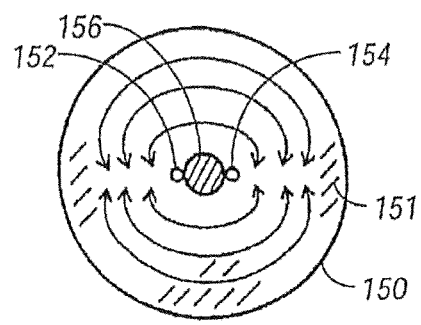
FIGS. 13A, 13B, 14A, 14B, 15A, 15B, 16A, and 16B illustrate additional embodiments of the heat treatment apparatus which employ RF energy for use with the methods of the present invention.
Figure 13B:
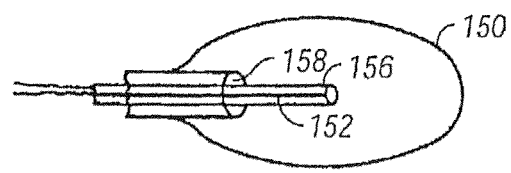

In FIG. 13A, which is a cross-sectional view of balloon 150, electrodes 152 and 154 are configured as elongated wires that are attached at opposite sides of nonconductive rod 156. FIG. 13B is a side view of the balloon with the electrodes inside the interior of the balloon which is sealed except for conduit 158 through which fluid 151 (e.g., saline) is introduced and removed.

Figure 14A:
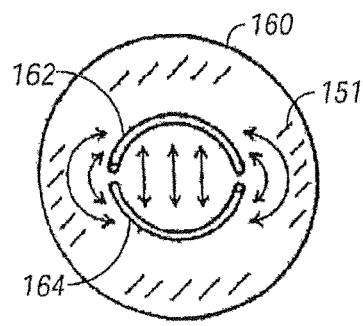
Figure 14B:
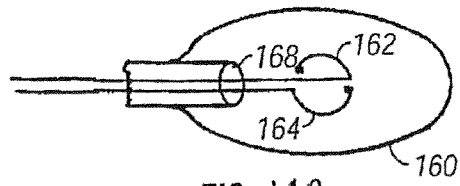

In FIG. 14A, which is a cross-sectional view of the balloon 160, electrodes 162 and 164 are wires each configured as a semi-circle and positioned at opposite sides of each other to form a circle. The electrodes have opposite polarities and are electrically insulated from each other. FIG. 14B is a side view of the balloon with the electrodes inside the interior of the balloon which is sealed except for conduit 168 through which fluid 151 is introduced and removed.

Figure 15A:
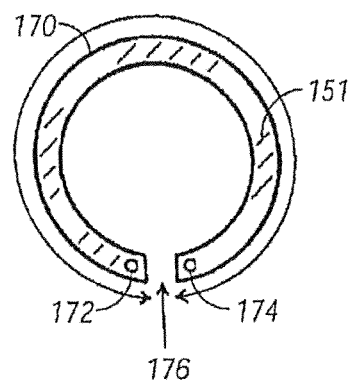
Figure 15B:
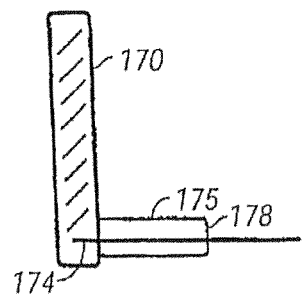

In FIG. 15A, which is cross-sectional view of the balloon 170, electrodes 172 and 174 are wires with tips that protrude into the interior region of the balloon which has a hollow disk or horse shoe configuration with partition 176 separating the two halves of the disk. Fluid 151 is introduced and removed from the balloon through conduit 178 in support member 175. The electrodes remain stationary in the solid regions of support member 175 as shown in side view FIG. 15B.

Figure 16A:
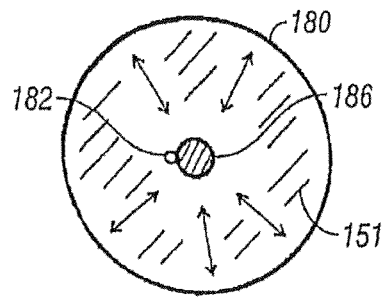
Figure 16B:
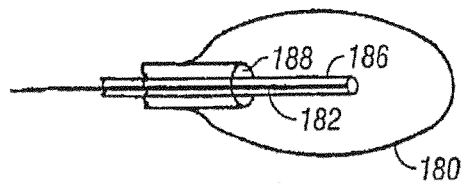

FIGS. 16A and 16B illustrate another embodiment in which the balloon 180 is fabricated of an electrically conductive material and therefore also serves as an electrode. In this fashion, one of the electrodes is an integral part of the balloon itself. The second electrode 182 is attached to non-conducting rod 186. FIG. 16B is a perspective view of the balloon with electrode 182 in the interior of the balloon which is sealed except for conduit 188 through which fluid 151 is introduced and removed. Suitable electrically conductive materials for fabricating the balloon in this case include, for example, a polyester film (e.g. MYLAR) that is coated with gold, silver, or platinum.

Figure 17:
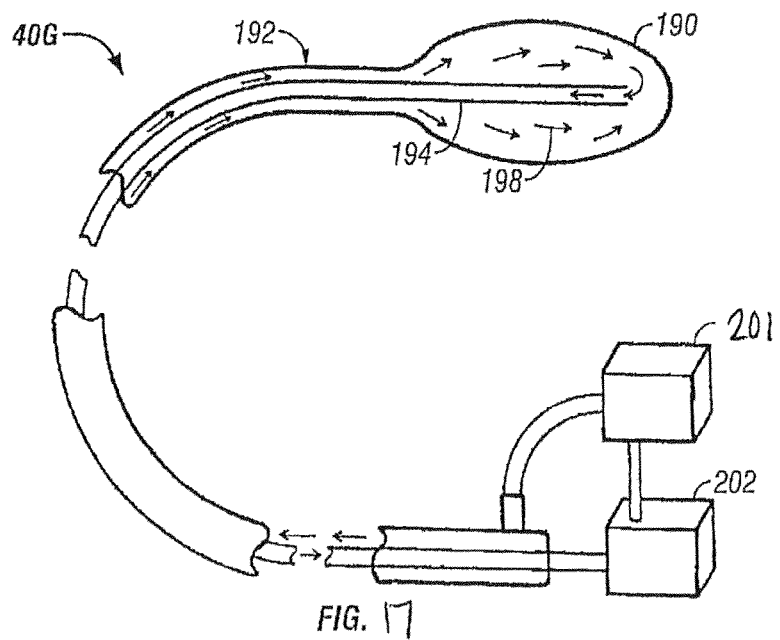
FIG. 17 illustrates an embodiment of the heat treatment apparatus which employs circulating heated fluid for use with the methods of the present invention.

FIG. 17 illustrates another embodiment of the treatment apparatus 40G for use with one embodiment of the present invention. With the treatment apparatus 40G, the heat generated to heat the fluid in the balloon is supplied by a circulating, hot fluid. Referring to FIG. 17, a balloon 190 (substantially the same as balloon 128 of the embodiment shown in FIG. 12A) is attached to a catheter 192 containing a smaller, coaxial catheter 194 (coaxial catheter 194 is substantially the same as catheter 192, differing only in size.) A heated fluid 198, which may be a liquid, such as water or physiologically compatibly saline solution, is pumped by a metering, circulating pump 202, through a heating unit 201, then through the outer catheter 192 to the balloon. The fluid heats the surface of the balloon and exits through the inner coaxial catheter 194 to return to the pump. A positive pressure is maintained within the system to keep the balloon at the proper inflation. This embodiment is employed in substantially the same manner as the other embodiments described above regarding its use to heat the airway tissue to induce fibrosis and strengthen the airway and destroy smooth muscle tone. The choice of the temperature of the circulating liquid is at the discretion of the operating surgeon, but will usually be in the range of about 60° C. to about 95° C.

Figure 18:
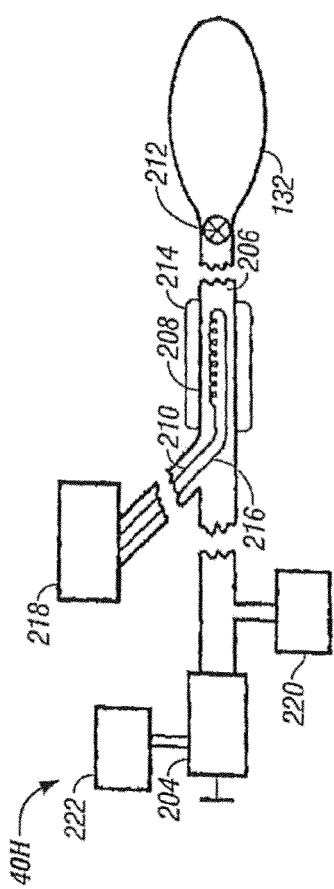
FIG. 18 illustrates an embodiment of the heat treatment apparatus that has both resistive heating and inductive heating for use with the methods of the present invention.

The treatment apparatus 40H shown in FIG. 18 represents another embodiment of the treatment apparatus for performing another embodiment of the present invention, wherein the heat generated to heat the fluid in the balloon is supplied by a hot fluid that is injected into the balloon. The catheter 208 includes electrodes 210 and 216 positioned in lumen 206 of the catheter. The electrodes are connected to AC generator 218 although an RF generator can also be used. The channel or lumen 206 also serves as a reservoir for liquid which is introduced from source 222 through syringe 204. Once the fluid is heated to the desired temperature, it can be injected into the interior of the balloon. As is apparent, the fluid serves both to inflate the balloon as well as to supply the heat treatment of the bronchial tube. A positive pressure is maintained within the system to keep the balloon at the proper inflation. Instead of using resistive heating, the fluid can be heated with heat exchanger 208.

Preferably, the RF energy is applied for a length of time in the range of about 1 second to about 600 seconds and preferably about 5 to about 120 seconds. Suitable RF power sources are commercially available and well known to those skilled in the art. In one embodiment the RF generator employed has a single channel that is capable of delivering approximately 1 to 100 watts and preferably 1 to 25 watts of RF energy and possesses continuous flow capability. Regardless of the source of energy used during treatment, the lumen or the bronchial tube is maintained at a temperature of at least about 60° C. and typically between 70° C. to 95° C. and preferably between 70° C. to 85° C.

Figure 12C:
FIG. 12C illustrates another embodiment of a treatment apparatus for use with the methods of the present invention.

The treatment apparatus of the present invention may include more than one balloon and attendant bipolar electrodes which are positioned along the length of the elongated member so that a plurality of locations along a bronchial tube can be treated simultaneously. FIG. 12C illustrates an alternative embodiment of the treatment apparatus of FIG. 12A described above, which includes two balloons 148A, 148B that are spaced apart. Each balloon 148A, 148B includes a suitable set of bipolar electrodes as described previously. The balloons can be connected to separate sources of fluid or they can share a common source.

Figure 19A:
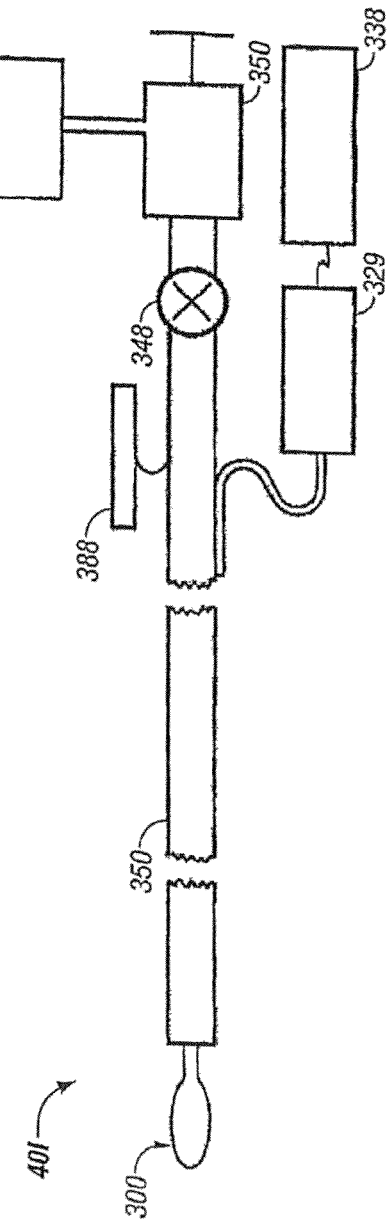

FIGS. 19A and 19B show a further embodiment of the treatment apparatus 40I for use with another embodiment of the present invention. The treatment apparatus 40I includes a balloon 300, similar to the balloons described earlier, that is positioned at or near the distal end of elongated rod 310 which is positioned within the lumen or aperture 351 of catheter sheath 350. It is understood that the term "rod" also encompasses tubes which have hollow channels. As shown, the balloon with inner surface 301 is in the inflated state having been inflated with an appropriate fluid such as air or saline that is injected from conduit 330 and into the interior of the balloon through aperture 331 in the rod. The apparatus includes electrodes 302 and 304, similar to those described earlier, which are spaced apart along the outer perimeter of the inflated balloon. It is understood that the number of electrodes and their configurations on the outer surface of the balloon can be varied. These electrodes come into contact with the wall of the airway when the balloon is inflated. The electrodes employed in the present invention can have different configurations. For example, the electrodes can be conventional coil wires with round cross sections, or they can have a non-round configuration, such as, for example, a thin, foil or band with a rectangular cross section. For the device shown in FIG. 19B, electrodes 302 and 304 are preferably flat bands each extending around the circumference of the balloon. To permit expansion of the balloon, each band is positioned around the outer surface of the balloon with the two ends overlapping each other. As shown the FIG. 19B, electrode 302 is a band having ends 303 and 313 with a portion of the band adjacent to end 303 overlapping a portion of the band adjacent to end 313. Similarly, electrode 304 is a band having overlapping ends 305 and 315.

The balloon of the treatment apparatus 401 is preferably constructed of nonelastic material that is initially folded and/or collapsed. In this non-inflated state, the diameter of the balloon is small enough that the balloon can be positioned inside an aperture or working channel of a bronchoscope. In use, the bronchoscope first is positioned at the treatment site before the balloon to exposed and then inflated. Heat treatment is then commenced to damage airway tissue to induce fibrosis and/or destroy smooth muscle tone.

FIGS. 19A and 19B show that electrodes 302 and 304 are connected via cables 322 and 342, respectively, to a radio frequency (RF) generator 329 with controls 338, such as described earlier. Rod 310 is also connected to syringe 350 which is employed to inject a fluid from source 346 through valve 348 into the balloon.

FIG. 20 illustrates another embodiment of the treatment apparatus 40J for use with another method of the present invention which includes a pair of electrode coils 410 and 420 that are positioned in tandem. The number of electrode coils is not critical. The apparatus also includes an elongated rod 430 which has a distal end 431 that is connected to a tip or knob 440 and has a proximal end which is at least partially slidably positioned inside aperture 451 of catheter sheath 450 that includes end coupler 435. Coil 410 has two ends, the first end 411 being attached to knob 440 and the second end 412 is attached to rotatable or floating coupler 470. Similarly, coil 420 has two ends, the first end 421 is attached to rotatable coupler 470 and the second end 422 is attached to end coupler 435.

As shown in FIG. 20, the coils are in the relaxed state which is meant that no torque is being applied to either coil. In this state, each coil has a "barrel" configuration so that the diameter of the outer contour formed by each coil is largest at its center and smallest at its two ends. A number of preferred methods can be employed to change the diameters of the contour. One method is to compress or expand the coils along the axis. For example, by pushing rod 430 outward so that knob 440 extends away from catheter sheath 450, the coil diameters will decrease. Another method of changing the diameter is to apply torque to the coils. Torque can be applied by rotating the rod in a clockwise or counterclockwise direction while keeping end coupler 435 stationary, e.g., attached to the inner surface of catheter sheath. Torque can also be applied by keeping rod 430 stationary while rotating end coupler 435. Alternatively, torque can be applied by rotating the rod in one direction while rotation end coupler 435 in the opposite direction. During the rotation process, rotatable coupler 470 will also rotate to thereby transfer torque from one coil to the other.

In practice, applying torque to adjust the radial diameters of the coils is preferred over compressing or pulling the coils lengthwise since applying torque creates less of a gradient in the diameter of each coil. According, preferably, the treatment apparatus is constructed so that end coupler 435 remains stationary. Torque is preferably applied by manually rotating rod 430. When more than one coil is employed, a rotatable coupler is required to connect adjacent coils. Multiple coil configurations are preferred over one with a single coil that has the same length (in the relaxed state) as the sum of the lengths of the smaller coils since the diameters of the smaller coils will tend to be more uniform and in contact with the wall of the bronchial tube being treated. Each coil in the embodiment shown in FIG. 20 is connected to an appropriate source of energy. For example, coils 410 and 420 can be connected by lines 415 and 425 to a radio frequency generator 430 as described above. In operation, the heat treatment apparatus 40J is positioned at the treatment site before the diameters of the coils are adjusted by applying torque. Energy is then applied to the coils.

FIGS. 21 and 22 show embodiments of the heat treatment apparatus 40K, 40L for use with further methods of the present invention, which are similar to that of FIG. 20. The apparatus of FIG. 21 includes a pair of electrode coils 510 and 520 that are positioned in tandem. The apparatus also includes an elongated rod 530 which has a distal end 531 that is connected to a tip or knob 540 and has a proximal end which is at least partially slidably positioned inside aperture 551 of catheter sheath 550 that includes end coupler 535. Coil 510 has two ends, the first end 511 being attached to knob 540 and the second end 512 is attached to rotatable coupler 570. Similarly, coil 520 has two ends, the first end 521 is attached to rotatable coupler 570 and the second end 522 is attached to end coupler 535. As is apparent, each electrode has a cone-shaped contour and comprises a coil that is wound about and along the axis of the rod 530 and which in the relaxed state has a large diameter at one end and a small diameter at the other end.

The treatment apparatus 40L of FIG. 22 includes a pair of electrode coils 610 and 620 that are positioned in tandem. The apparatus also includes an elongated rod 630 which has a distal end 631 that is connected to a tip or knob 640 and has a proximal end which is at least partially slidably positioned inside aperture 651 of catheter sheath 650 that includes end coupler 635. Coil 610 has two ends, the first end 611 being attached to knob 640 and the second end 612 is attached to rotatable coupler 670. Similarly, coil 620 has two ends, the first end 621 is attached to rotatable coupler 670 and the second end 622 is attached to end coupler 635. As is apparent, each electrode has a single loop configuration that comprises a coil that is wound once about the rod 630. In this configuration, the two electrodes when in the relaxed state preferably form loops having the same diameter.

The devices 40K, 40L of FIGS. 21 and 22 operate in essentially the same manner as the device 40J of FIG. 20. Specifically, the same methods can be employed to adjust the radial diameter of the coils by compressing or pulling the coils or by applying torque to the coils. In addition, each coil is connected to an appropriate source of energy. For example, coils 610 and 620 can be connected by lines 615 and 625 to a radio frequency generator 330 as shown in FIG. 19A.

The electrodes may be constructed of a suitable current conducting metal or alloys such as, for example, copper, steel, and platinum. The electrodes can also be constructed of a shape memory alloy which is capable of assuming a predetermined, i.e., programmed, shape upon reaching a predetermined, i.e., activation, temperature. Such metals are well known in the art as described, for example, in U.S. Pat. Nos. 4,621,882 and 4,772,112. For the present invention, the shape memory metal used should have the characteristic of assuming a deflection away (i.e., expands) from the elongated rod when activated, i.e., heated in excess of the normal body temperature and preferably between 60° C. and 95° C. A preferred shape memory alloy is available as NITINOL from Raychem Corp., Menlo Park, Calif. For the heat treatment apparatuses that employ coils as shown in FIGS. 19-22, preferably the electrodes are constructed of NITINOL in a predetermined shape and in the alloy's super elastic phase which can withstand very large deflections without plastic deformation.

Alternatively, the heat treatment apparatuses employing a unipolar electrode can also be employed. For instance, in the case of the embodiment shown in FIGS. 19A and 19B, the heating device can have one or more inner electrodes 302 and/or 304 on the balloon surface and an outer or external electrode 388 that has a much larger surface area than that of the internal electrode(s) and that is placed on the outer surface of the patient's body. For example, the external electrode can be an external metal mesh or solid plate that is placed on the skin with conductive gel. Both the internal and external electrodes are connected to an RF generator which produces an electric field at a high frequency within the balloon. Because the collective surface area of the internal electrode(s) is much smaller than that of the outer electrode, the density of the high frequency electric field is much higher around the internal electrode(s). The electric field reaches its highest density in the region near the internal electrode(s). The increased density of the field around the internal electrode(s) produces localized heating of the tissue to destroy smooth muscle tone and damage tissue to cause fibrosis, which stiffens the airway so as to increase gas exchange performed by the lung.

As is apparent, the heat treatment apparatus can have more than one electrode that is positioned at or near the distal end of the elongated rod. For example, FIG. 23 depicts schematically the distal end 700 of a treatment apparatus 40M which comprises electrodes 701, 702, and 703. In this configuration, if the device operates in the bipolar mode, two of the three electrodes (e.g., 701 and 702) are connected to one pole of the RF generator and the other electrode (702) is connected to the other pole. Heat will be generated in the tissue adjacent the region between electrodes 701 and 702 and the region between electrodes 702 and 703. These electrodes 701, 702, and 703 can be attached to the exterior surface of a balloon, alternatively they represent adjustable coils in embodiments that do not require a balloon.

When the treatment apparatus 40M includes multiple electrodes, not all the electrodes need to be activated at the same time, that is, different combinations of electrodes can be employed sequentially. For example, in the case of the above described bipolar embodiment with three electrodes, electrodes 701 and 702 can be first activated to heat a section of the bronchial tube wall. During the heat treatment, electrode 703 can also be activated so that a second section of the bronchial tube wall is heat treated simultaneously. Alternatively, electrode 701 is disconnected to the RF generator before electrode 703 is activated so that the second section is treated subsequent to treatment of the first section.

In addition, when a treatment apparatus 40M includes multiple electrodes, the device can operate in the monopolar, bipolar mode, or both modes at the same time. For instance, electrodes 701 and 702 can be designed to operate in the bipolar mode while electrode 703 is designed to operate in the monopolar mode. As a further variation, the electrodes can be constructed of different materials and/or constructed to have different configurations. For example, electrode 701 can be made of a shape memory alloy and/or it can be a coil while each of the other electrodes 702 and 703 can be made of a non-shape memory material and/or it can be a band with a rectangular cross section.

The treatment apparatus can comprise more than one balloon that is attached to the elongated rod. For example, FIG. 24 depicts schematically the distal end of a treatment apparatus 40N for use with embodiments of the present invention, which comprises balloons 810 and 820. Electrodes 811 and 812 are attached to the exterior surface of balloon 810 and electrodes 821 and 822 are attached to the exterior surface balloon 820. The treatment apparatus 40N includes an elongated rod 860 which is positioned with the lumen of catheter sheath 850. The treatment apparatus 40N is preferably constructed in the same manner as the device shown in FIG. 19B except for the additional balloon. Operation of the device 40N is also similar although the surgeon has the choice of activating both sets of electrode simultaneously or one set at a time.

FIG. 25 illustrates another embodiment of a treatment apparatus 40P for use with the methods of the present invention. The treatment apparatus 40P is introduced through a catheter, bronchoscope, or other tubular introducer member 1012. The heat treatment apparatus includes a shaft 1014 and one or more electrodes 1016. Electrically connected to the electrodes 1016 is an RF generator 1018 or other energy source. The RF generator is controlled by a controller 1020. Although the invention will be described as employing an RF generator, other energy sources, such as alternating current and microwave may also be used.

In accordance with the embodiment of FIG. 25, the electrodes include a first conical electrode 1016A connected to an inner shaft 1022 and a second conical electrode 1016B connected to an outer shaft 1024. The conical electrodes 1016A, 1016B are positioned with their axes aligned and may be fixed or movable with respect to each other. Each of the conical electrodes 1016A, 1016B includes at least two overlapping sections 1026. The sections 1026 are flexible and overlap one another to allow the electrodes 1016A, 1016B to be compressed within the lumen of the catheter 1012 for insertion into the bronchial tube of a patient. Once the catheter 1012 is positioned with a distal end at a desired treatment location within the bronchial tubes, the shaft 1014 is used to push the electrodes 1016A, 1016B out of the distal end of the catheter. Once deployed from the catheter 1012, the electrodes 1016A, 1016B expand radially outwardly until the distal ends of the electrodes contact the walls of the bronchial tube.

The electrodes 1016A, 1016B are electrically connected to the RF generator 1018 by electrical cables 1028, 1030. When the treatment apparatus 40P employs two electrodes 1016A, 1016B the two electrodes are preferably oppositely charged with one of the electrodes connected to a negative output of the RF generator and the other electrode connected to a positive output of the RF generator. Alternatively, both the electrodes 1016A, 1016B or a single electrode 1016 may be connected to the same output of the RF generator and an external electrode 1034 may be used. The external electrode 1034 is connected to an output of the RF generator 1018 having an opposite polarity of the output connected to the internal electrode 1016.

Figure 26:
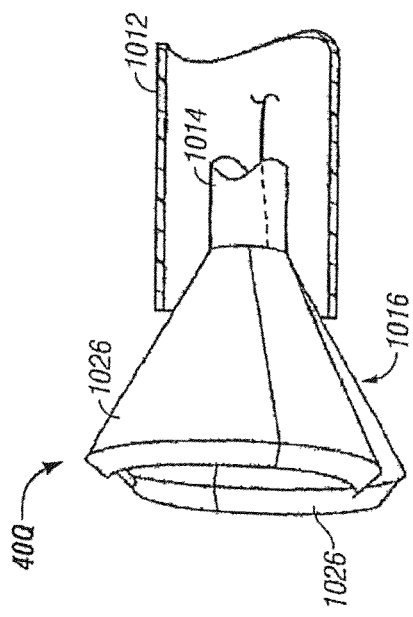
FIG. 26 is an enlarged partial cross-sectional view of a distal end of another embodiment of a heat treatment apparatus having one collapsible electrode for use with the methods of the present invention.

FIG. 26 illustrates an alternative embodiment of a heat treatment apparatus 1040 having a single electrode 1016 positioned on a shaft 1014. The electrode 1016 is shown as it is deployed from the distal end of a catheter 1012 for heat treatment of the lumen of bronchial tubes.

The electrodes 1016 of the embodiment of FIGS. 25 and 26 are formed of a suitable conductive material such as metal, plastic with a metal coating, or the like. The two or more sections 1026 of each of the cone shaped electrodes is fixed to the shaft 1014 and biased outwardly so that the sections expand or unfold to an enlarged diameter upon release from the distal end of the catheter 1012. The electrodes 1016 preferably have an enlarged diameter which is equal to or slightly greater than an interior diameter of the bronchial tube to be treated. As shown most clearly in FIG. 26, the sides of the sections 1026 overlap one another even in the expanded state.

In operation of the embodiments of FIGS. 25 and 26, the distal end of the catheter 1012 is first positioned at the treatment site by known catheter tracking methods. The catheter 1012 is then retracted over the heat treatment apparatus to exposed and expand the electrodes 1016. Each electrode 1016 of the energy emitting apparatus 40P expands radially outward upon retraction of the catheter 1012 until the electrodes come into contact with the wall of the bronchial tube. In the embodiment of FIG. 26, the distance between the two energy emitting electrodes 1016A, 1016B may be fixed or may be changeable by sliding the inner shaft 1022 within the outer shaft 1024. When treatment is completed the heat treatment apparatus 40P is retracted back inside the catheter 1012 by sliding the catheter over the electrodes. As the heat treatment apparatus 40P is retracted the sides of the sections 1026 of the electrode 1016 slide over each other upon coming into contact with a distal edge of the catheter 1012.

Figure 27:
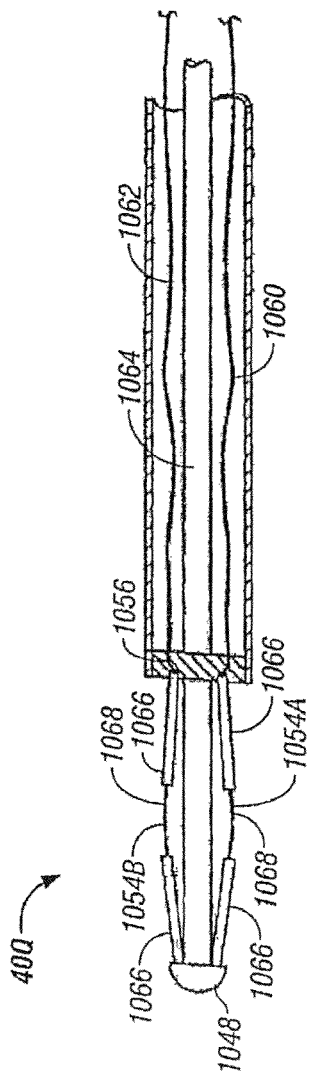
FIG. 27 is a side cross-sectional view of an alternative embodiment of a heat treatment apparatus having two wire shaped electrodes for use with the methods of the present invention.

FIGS. 27 and 28 illustrate an alternative embodiment of a treatment apparatus 40Q for use with the methods of the present invention. The treatment apparatus 40Q may be delivered to a treatment site in a collapsed configuration illustrated in FIG. 27. The treatment apparatus 40Q includes two leaf spring or wire shaped electrodes 1054A and 1054B. The electrodes 1054A, 1054B are connected to an insulating end cap 1056 of a hollow shaft 1058. The electrodes 1054A, 1054B are electrically connected to the RF generator or other energy source by electric cables 1060, 1062. The heat treatment apparatus 1050 is provided with a central shaft 1064 which is slidable within the hollow shaft 1058. The central shaft 1064 has a shaft tip 1048 which is connected to a distal end of each of the electrodes 1054A, 1054B.

Each of the electrodes 1054A, 1054B is preferably insulated with an insulating sleeve 1066 except for an exposed contact section 1068. The treatment apparatus 40Q is delivered to the lumen of a bronchial tube to be treated either alone or through a catheter, bronchoscope, or other channel. The electrodes 1054A, 1054B are expanded radially outwardly by moving the central shaft 1064 proximally with respect to the hollow shaft 1058 of the treatment apparatus 40Q. Upon expansion, the exposed contact sections 1068 of the electrodes 1054A, 1054B come into contact with the walls of the airway or bronchial tube B, shown in FIG. 28. The electrodes 1054A, 1054B may be configured to bend at a predetermined location forming a sharp bend as shown in FIG. 28. Alternatively, the electrodes 1054A, 1054B may form a more gradual curve in the expanded configuration. The electrodes 1054A, 1054B are preferably connected to opposite poles of the energy source. Alternatively, both of the electrodes 1054A, 1054B may be connected to the same lead of the energy source and the external electrode 1034 may be used. Upon completion of the treatment process the electrodes 1054 are retracted back into the catheter for removal or moving to a subsequent treatment site.

Figure 30:
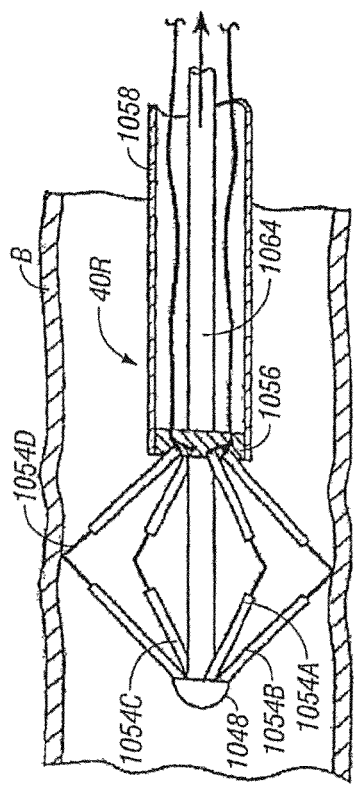
FIG. 30 is an end view of the device of FIG. 29.

FIGS. 29 and 30 illustrate another embodiment of the treatment apparatus 40R for use with embodiments of the present invention. The treatment apparatus 40R includes four electrodes 1054A, 1054B, 1054C, 1054D. The four electrode embodiment of FIGS. 29 and 30 operates in the same manner as the embodiments of FIGS. 27 and 28 with a slidable central shaft 1064 employed to move the electrodes from a compressed configuration to the expanded configuration illustrated in FIGS. 29 and 30. Each electrode 1054A-1054D is connected at a proximal end to the insulating end cap 1056 of the hollow shaft 1058 and at a distal end to the central shaft 1064. Relative motion of the hollow shaft 1058 with respect to the central shaft 1064 moves the electrodes 1054 from the collapsed to the expanded position.

Figure 31:
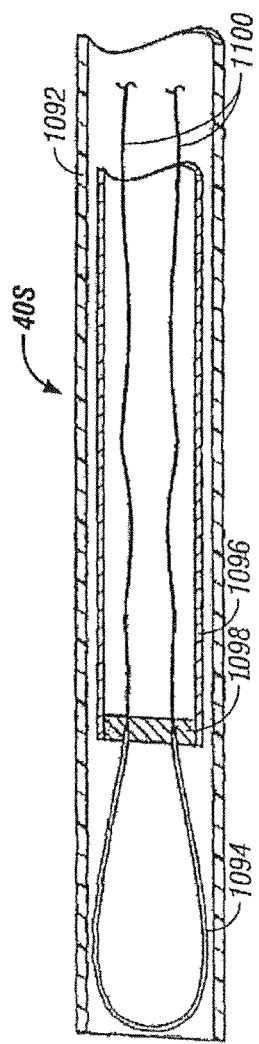
FIG. 31 is a side cross-sectional view of an alternative embodiment of a heat treatment apparatus with a loop shaped electrode in a contracted state for use with the methods of the present invention.

FIGS. 31 and 32 illustrate a further embodiment of a heat treatment apparatus 40S employing one or more wire or leaf spring shaped loop electrodes 1094. As in the previous embodiments, the loop electrode 1094 expands from a contracted positioned within a catheter 1092 as illustrated in FIG. 31 to an expanded position illustrated in FIG. 32. In the expanded position, the loop shaped electrode 1094 comes into contact with the walls of the airway or bronchial tube B. Although the embodiment of FIGS. 31 and 32 has been illustrated with a single loop shaped electrode 1094, it should be understood that multiple loop shaped electrodes may also be use. The loop shaped electrode 1092 is connected to the shaft 1096 of the heat treatment apparatus 40S by an end cap 1098 and is electrically connected to the energy source by the electric cables 1100.

FIGS. 33-36 illustrate an alternative embodiment of a treatment apparatus 40T for use with the embodiments of the present invention, The treatment apparatus 40T includes a flexible plate shaped electrode 1114. The flexible plate shaped electrode 1114 is substantially flower shaped in plan having a plurality of petals 1116 with curved distal ends extending from a central section 1120. The petals 1116 flex along a hinge line 1118 to the compressed insertion configuration illustrated in FIG. 33 in which the petals 1116 extend substantially perpendicularly from the central section 1120 of the flexible plate shaped electrode 1114.

Figure 35:
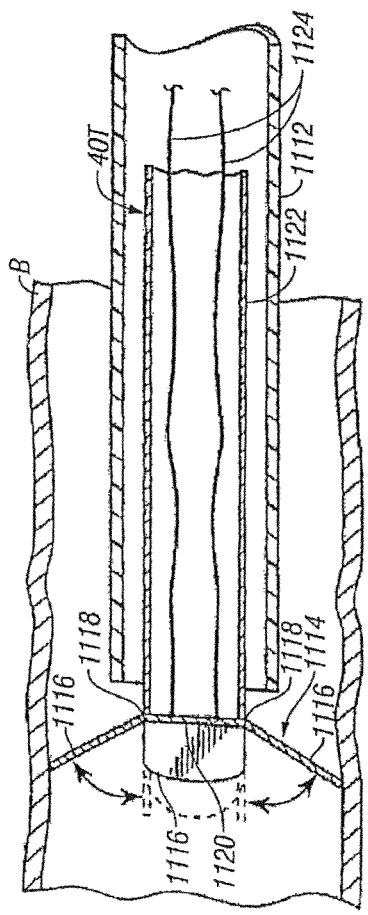
FIG. 35 is a side cross-sectional view of the apparatus of FIG. 33 with the plate shaped electrodes in an expanded configuration.
Figure 36:
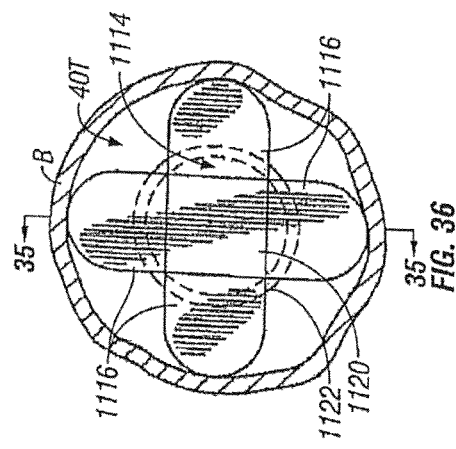
FIG. 36 is an end view of the expanded apparatus of FIG. 35 for use with the methods of the present invention.

As illustrated in FIGS. 35 and 36, when the treatment apparatus 40T is moved distally with respect to the catheter 1112 to deploy the electrode 1114 the petals 1116 move outwardly until the petal tips come into contact with the walls of the bronchial tube B. The flexible plate shaped electrode 1114 is preferably formed of a conductive material and fixed to the end of a shaft 1122. Electric cables 1124 connect the plate shaped electrode 1114 to the energy source.

The electrodes in each of the forgoing embodiments may be fabricated of any material which when compressed will return to an expanded configuration upon release of the compression forces. For example, one method of controlling the expansion of the electrodes is the use of shape memory alloy electrodes. With a shape memory alloy, the constraint of the electrodes within a catheter may not be necessary. The shape memory alloy electrodes may be formed to expand to an expanded energy delivery configuration upon heating to body temperature within the body. The expansion of the electrodes is limited by the size of the bronchial tube in which the electrode is positioned.

As described above, the heat treatment apparatus may be employed in a bipolar mode in which two different expandable electrodes are connected to two different outputs of the RF generator 1018 having opposite polarities. For example, the electrodes 1016A, 1016B may be connected by the electrical cables 1028, 1030 to different terminals of the RF generator 1018. Alternatively, when more than two electrodes 1016 are employed, multiple electrodes may be connected to one terminal of the RF generator. In each of the embodiments of the heat treatment apparatus, the oppositely charged electrodes are separated by an insulating material. For example, in the embodiment of FIG. 36, the inner shaft 1022 and outer shaft 1024 are formed of an insulating material. Further, in the embodiments of FIGS. 27-29 the end cap 1056 and central shaft distal tip are formed of insulating materials.

In the case where the apparatus includes only one electrode 1016 as shown in FIG. 26, the electrode will be connected to the positive or negative terminal of the RF generator 1018 and the opposite terminal of the RF generator will be connected to the external electrode 1032.

The frequency range of RF radiation useful in the present invention is typically about 10 KHz to about 100 MHZ, preferably in the range of about 200 KHz to about 800 KHz. However, frequencies outside this range may be used at the discretion of the operating surgeon. Typically, the amount of power employed will be from about 0.01 to 100 watts and preferably in the range of about 1 to 25 watts for about 1 to 60 seconds. Alternatively, alternating current or microwave radiation typically in the frequency range of about 1,000 MHZ to about 2,000 MHZ and preferably from about 1,100 MHZ to about 1,500 MHZ may be used in place of RF radiation. In the latter case, the RF generator 1018 is replaced with a microwave generator, and the electric cables 1028, 1030 are replaced with waveguides.

When the heat treatment apparatus with the bipolar electrodes is positioned inside the lumen of a bronchial tube, activation of the RF generator 1018 causes tissue in the lumen wall to increase in temperature. The heating may be caused by resistance heating of the electrodes themselves and/or power losses through the tissue of the bronchial wall. The particular heat pattern in the tissue will depend on the path of the electric field created by the positioning and configuration of the electrodes.

In the monopolar mode, the external electrode 1034, shown in FIG. 25, having a much larger surface area than the inner electrodes is placed on the outer surface of the patient's body. For example, the external electrode 1034 can be an external metal mesh or a solid plate that is placed on the skin with conductive gel. Both the internal and external electrodes are connected to the RF generator 1018 which produces an electric field at a high frequency. Because the collective surface area of the internal electrodes is much smaller than that of the outer electrode 1034, the density of the high frequency electric field is much higher around the internal electrodes. The electric field reaches its highest density in the region near the internal electrodes. The increased density of the field around the internal electrodes produces localized heating of the tissue around the bronchial tube without causing significant heating of the body tissue between the bronchial tube and the external electrode.

In use, after the operating surgeon has placed the heat treatment apparatus within the lumen of a bronchial tube to be treated, if necessary, the catheter is retracted to expose the electrodes. In the case where the lumen of the bronchial tube has collapsed or is partially collapsed, the size of the energy emitting device is designed so that expansion of the electrodes causes the lumen to expand to its normal or non-collapsed diameter due to contact of the electrodes with the inner surface of the lumen. Alternatively, in the case where the lumen has not collapsed, the device is designed so that upon expansion the electrodes are in substantial contact with the inner surface of the lumen. Indeed, only minimum expansion may be necessary in treating a non-collapsed bronchial lumen.

The degree of expansion of the electrodes of the heat treatment apparatus can be monitored by means of endoscopy, fluoroscopy, or by other suitable imaging methods of the art. Generally, the heat required is induced in the tissue of the bronchial tube wall by the RF or microwave radiation emitting from the electrodes. The RF or microwave energy is applied while observing the tissue for changes via simultaneous endoscopy, or other suitable imaging methods of the art.

The electrodes employed in the heat treatment apparatus are constructed of a suitable current conducting metal or alloys such as, for example, copper, steel, platinum, and the like or of a plastic material with a conductive metal insert. The electrodes can also be constructed of a shape memory alloy which is capable of assuming a predetermined, i.e., programmed, shape upon reaching a predetermined, i.e., activation temperature. Such metals are well known in the art as described, for example, in U.S. Pat. Nos. 4,621,882 and 4,772,112. For the present invention, the shape memory metal used should have the characteristic of assuming a deflection away (i.e., expands) from the elongated rod when activated, i.e., heated in excess of the normal body temperature and preferably between 60° C. and 95° C. A preferred shape memory alloy is available as NITINOL from Raychem Corp., Menlo Park, Calif. In one embodiment, the electrodes are constructed of NITINOL in a predetermined shape and in the alloy's super elastic phase which can withstand very large deflections without plastic deformation.

Substantial tissue transformation may be achieved very rapidly, depending upon the specific treatment conditions. Because the transformation can proceed at a rather rapid rate, the RF energy should be applied at low power levels. Preferably, the RF energy is applied for a length of time in the range of about 0.1 second to about 600 seconds, and preferably about 1 to about 60 seconds. Suitable RF power sources are commercially available and well known to those skilled in the art. In one embodiment the RF generator 18 employed has a single channel, delivering approximately 1 to 100 watts, preferably 1 to 25 watts and possessing continuous flow capability. The rate of tissue damage to induce fibrosis can be controlled by varying the energy delivered to the heat treatment apparatus. Regardless of the source of energy used during treatment, the lumen or the bronchial tube is maintained at a temperature of at least about 45° C., preferably between 60° C. and 95° C.

When the heat treatment apparatus includes multiple energy emitting devices, not all the electrodes need to be activated at the same time. That is, different combinations of electrodes can be employed sequentially. For example, in the case of the embodiment shown in FIG. 25, with two electrodes 1016A, 1016B, the electrodes can be activated simultaneously or sequentially.

Figure 46:
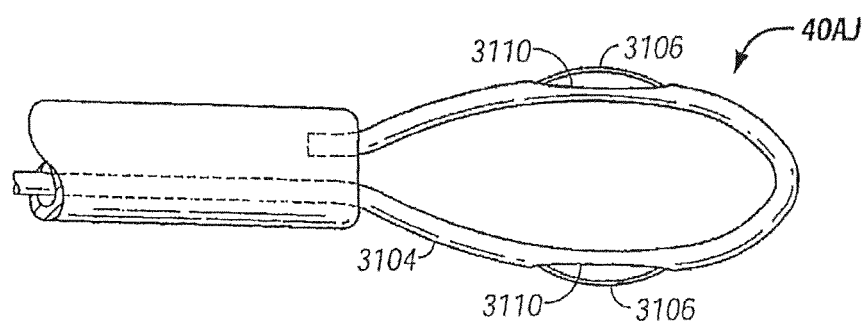
FIG. 46 is a side view of an embodiment of a treatment apparatus having electrodes exposed by cut away sections of a tube for use with the methods of the present invention.
Figure 47:
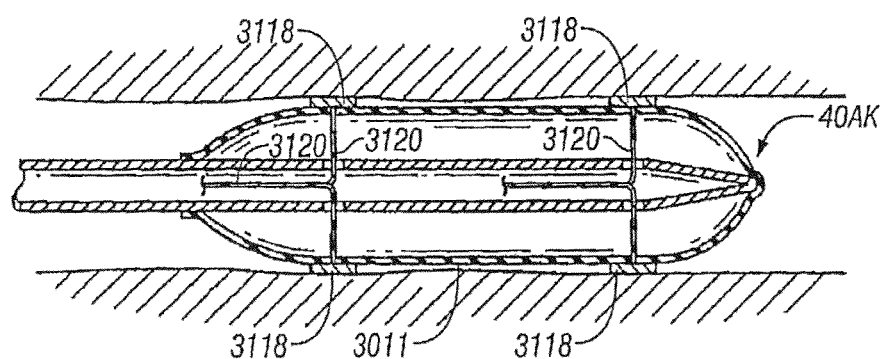
FIG. 47 is a side cross-sectional view of an embodiment of a treatment apparatus with electrodes positioned on an expandable balloon for use with the methods of the present invention.
Figure 48:
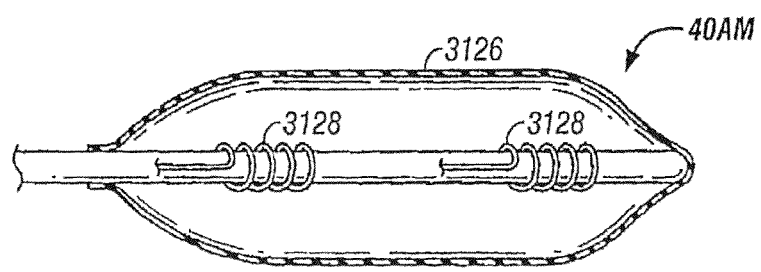
FIG. 48 is a schematic side view of an embodiment of a treatment apparatus with a balloon for heating of tissue for use with the methods of the present invention.

FIGS. 37-48 illustrate further embodiments of treatment apparatus that may be used with the methods of the present invention. The treatment apparatus of FIGS. 37-47 include tissue contacting electrodes configured to be placed within the airway. These apparatus can be used for delivering radio frequency in either a monopolar or a bipolar manner or for delivering other energy to the tissue, such as conducted heat energy from resistively heated electrodes, similar to the previously described treatment apparatus. For monopolar energy delivery, one or more electrodes of the treatment apparatus are connected to a single pole of the energy source 3032 and an optional external electrode 3044 is connected to an opposite pole of the energy source. For bipolar energy delivery, multiple electrodes are connected to opposite poles of the energy source 3032 and the external electrode 3044 is omitted. The number and arrangement of the electrodes may vary depending on the pattern of energy delivery desired. The treatment apparatus of FIG. 48 is used to deliver radiant or heat energy to the airway. The treatment apparatus of FIG. 48 can also deliver indirect radio frequency or microwave energy to the tissue.

Figure 37A:
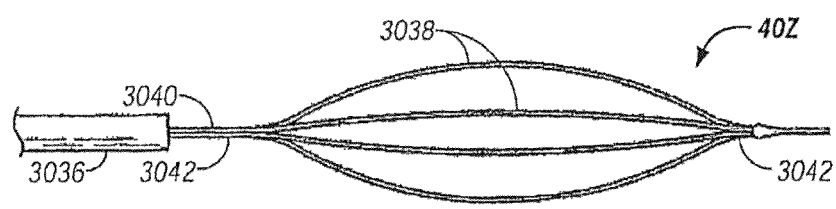
FIGS. 37A and 37B are side views of two variations of an embodiment of a treatment apparatus having a plurality of wire shaped electrodes for use with the methods of the present invention.

The treatment apparatus 40Z of FIG. 37A includes a catheter 3036 for delivering a shaft 3040 having a plurality of electrodes 3038 to a treatment site. The electrodes 3038 are formed from a plurality of wires which are soldered or otherwise connected together at two connection areas 3042. The electrodes 3038 between the connection areas 3042 are formed into a basket shape so that arch shaped portions of the wires will contact the walls of an airway. The wires may be coated with an insulating material except at the tissue contact points. Alternatively, the wires of the basket may be exposed while the connection areas 3042 and shaft 3040 are insulated. Preferably, the electrodes 3038 are formed of a resilient material which will allow the distal end of the treatment apparatus to be retracted into the catheter 3036 for delivery of the catheter to the treatment site and will allow the electrodes to return to their original basket shape upon deployment. The treatment apparatus 40Z is preferably configured such that the electrodes 3038 have sufficient resilience to come into contact with the airway walls for treatment.

Figure 37B:
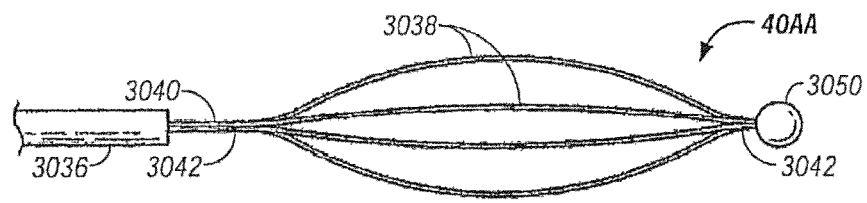
Figure 37C:
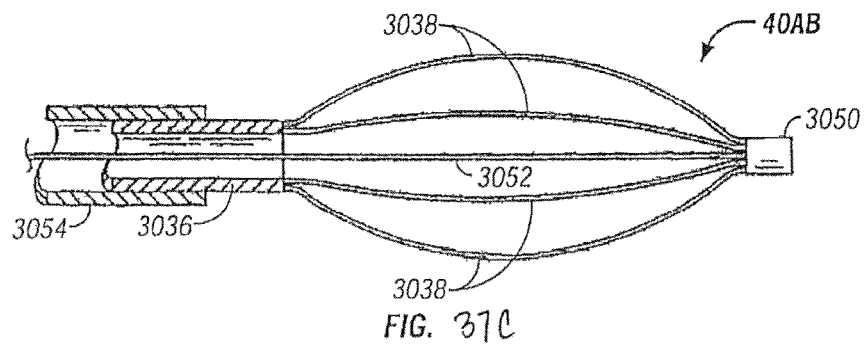
FIG. 37C is a cross-sectional side view of another variation of a treatment apparatus having a plurality of wire shaped electrodes for use with the methods of the present invention.

FIG. 37B illustrates a treatment apparatus 40AA in which the distal end of the device is provided with a ball shaped member 3050 for easily inserting the device to a treatment site without causing trauma to surrounding tissue. FIG. 37C illustrates a treatment apparatus 40AB having electrodes 3038 connected to the distal end of the catheter 3036 and forming a basket shape. The basket shape may be expanded radially during use to insure contact between the electrodes 3038 and the airway walls by pulling on a center pull wire 3052 which is connected to a distal end 3050 of the device and extends through a lumen of the catheter 3036. The treatment apparatus 40AB may be delivered to a treatment site through a delivery catheter or sheath 3054 and may be drawn along the airway to treat the airway in a pattern of longitudinal or helical stripes.

Figure 38:
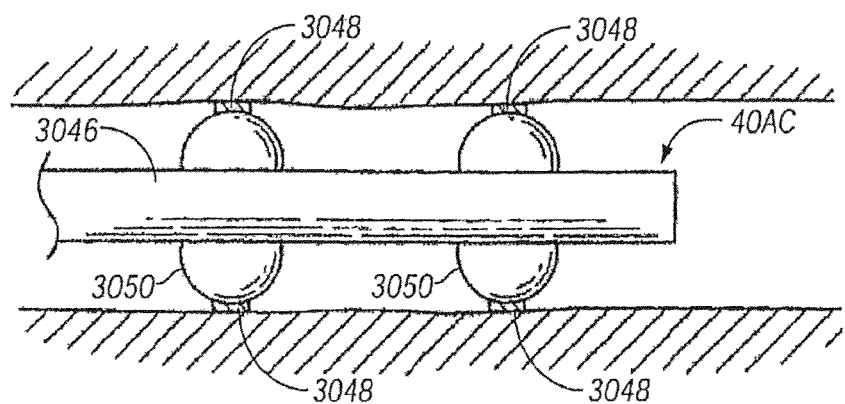
FIG. 38 is a side view of another embodiment of a treatment apparatus with electrodes positioned on expandable balloons for use with the methods of the present invention.

FIG. 38 illustrates a treatment apparatus 40AC in which a catheter shaft 3046 is provided with a plurality of electrodes 3048 positioned on inflatable balloons 3050. The balloons 3050 are inflated through the catheter shaft 3046 to cause the electrodes 3048 come into contact with the airway walls 3100. The electrodes 3048 are preferably connected to the energy source 3032 by conductive wires (not shown) which extend from the electrodes through or along the balloons 3050 and through the catheter shaft 3046 to the energy source. The electrodes may be used in a bipolar mode without an external electrode. Alternatively, the treatment apparatus 40AC may be operated in a monopolar mode with an external electrode 3044. The electrodes 3048 may be continuous circular electrodes or may be spaced around the balloons 3050.

Figure 39:
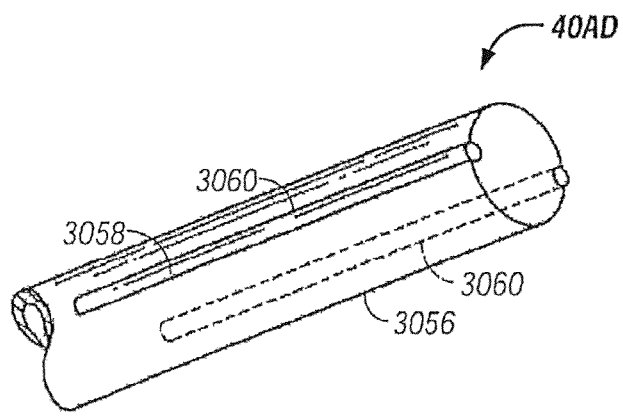
FIG. 39 is a perspective view of an embodiment of a treatment apparatus with electrodes positioned in grooves for use with the methods of the present invention.

An alternative apparatus device 40AD of FIG. 39 includes a catheter 3056 having one or more grooves 3060 in an exterior surface. Positioned within the grooves 3060 are electrodes 3058 for delivery of energy to the airway walls. Although the grooves 3060 have been illustrated in a longitudinal pattern, the grooves may be easily configured in any desired pattern. Preferably, the treatment apparatus 40AD of FIG. 39 includes a biasing member (not shown) for biasing the catheter 3056 against the airway wall such that the electrodes 3058 contact the tissue. The biasing member may be a spring element, an off axis pull wire, an inflatable balloon element, or other biasing member. Alternatively, the biasing function may be performed by providing a preformed curve in the catheter 3056 which causes the catheter to curve into contact with the airway wall when extended from a delivery catheter.

Figure 40:
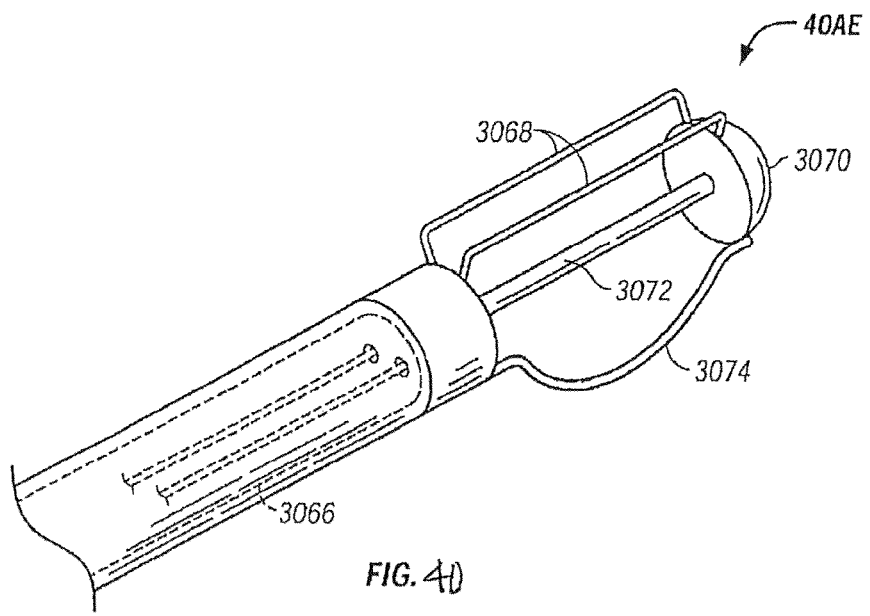
FIG. 40 is a perspective view of an embodiment of a treatment apparatus with electrodes in a biasing element for use with the methods of the present invention.

FIG. 40 illustrates a treatment apparatus 40AE having one or more electrodes 3068 connected to a distal end of a catheter 3066. The electrodes 3068 are supported between the distal end of the catheter 3066 and a device tip 3070. A connecting shaft 3072 supports the tip 3070. Also connected between the distal end of the catheter 3066 and the tip 3070 is a spring element 3074 for biasing the electrodes 3068 against a wall of the airway. The spring element 3074 may have one end which slides in a track or groove in the catheter 3066 such that the spring can flex to a variety of different positions depending on an internal diameter of the airway to be treated.

Figure 41:
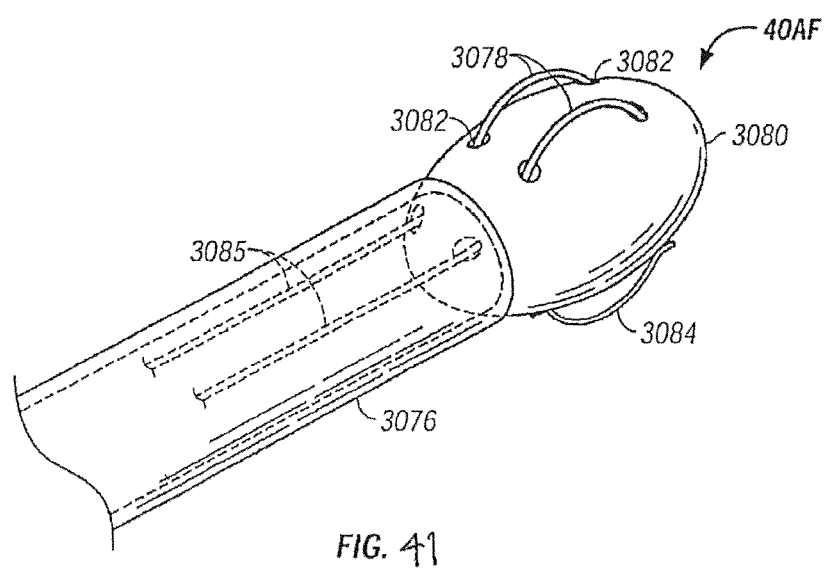
FIG. 41 is a perspective view of an embodiment of a treatment apparatus with electrodes and a biasing element for use with the methods of the present invention.

FIG. 41 illustrates an alternative treatment apparatus 40AF in which the one or more electrodes 3078 are positioned on a body 3080 secured to an end of a catheter 3076. In the FIG. 41 embodiment, the body 3080 is illustrated as egg shaped, however, other body shapes may also be used. The electrodes 3078 extend through holes 3082 in the body 3080 and along the body surface. A biasing member such as the spring element 3084 is preferably provided on the body 3080 for biasing the body with the electrodes against the airway walls. Leads 3085 are connected to the electrodes and extend through the catheter 3076 to the energy source 3032.

Figure 42:
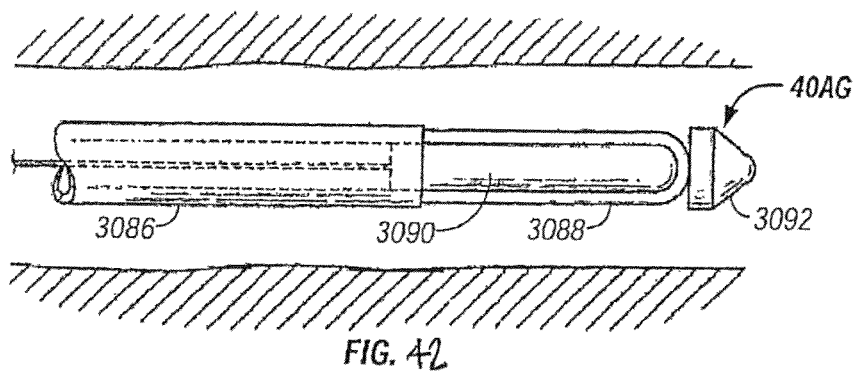
FIG. 42 is a side view of an embodiment of a treatment apparatus in an unexpanded position for use with the methods of the present invention.
Figure 43:
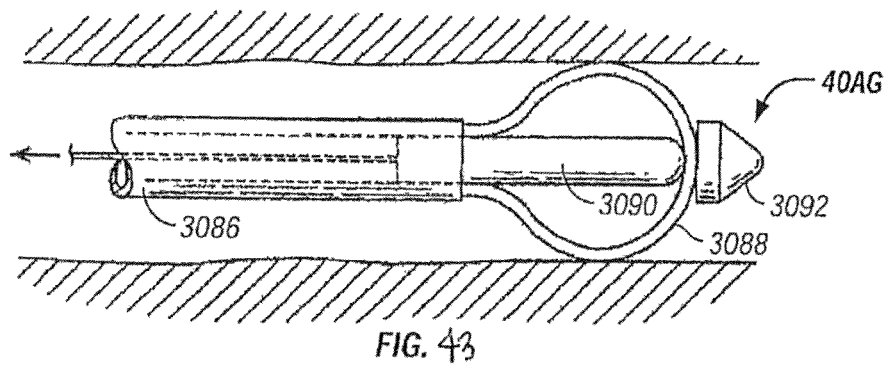
FIG. 43 is a side view of the treatment apparatus of FIG. 42 in an expanded position.

FIGS. 42 and 43 illustrate a further treatment apparatus 40AG having one or more loop shaped electrodes 3088 connected to a catheter shaft 3086. In the unexpanded position shown in FIG. 42, the loop of the electrode 3088 lies along the sides of a central core 3090. A distal end of the loop electrode 3088 is secured to the core 3090 and to an optional tip member 3092. The core 3090 is slidable in a lumen of the catheter 3086. Once the treatment apparatus 40AG has been positioned with the distal end in the airway to be treated, the electrode is expanded by pulling the core 3090 proximally with respect to the catheter 3086, as shown in FIG. 43. Alternatively, the electrode 3088 or the core 3090 may be spring biased to return to the configuration of FIG. 43 when a constraining force is removed. This constraining force may be applied by a delivery catheter or bronchoscope through which the treatment apparatus 40AG is inserted or by a releasable catch.

Figure 44:
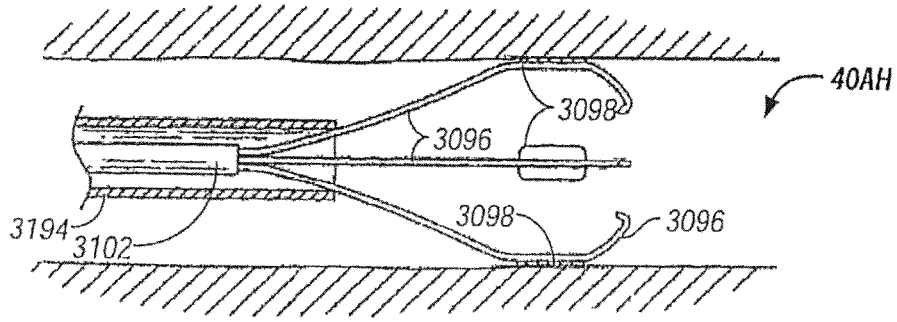
FIG. 44 is a side view of an embodiment of a treatment apparatus in an expanded position for use with the methods of the present invention.

The treatment apparatus 40AH of FIG. 44 includes a plurality electrodes 3098 positioned on leaf springs 3096 which are outwardly biased. The leaf springs 3096 are connected to a shaft 3102 which is positioned within a delivery catheter 3094. The leaf springs 3096 and electrodes 3098 are delivered through the delivery catheter 3094 to a treatment site within the airways. When the leaf springs 3096 exit the distal end of the delivery catheter 3094, the leaf springs bend outward until the electrodes 3098 come into contact with the airway walls for application of energy to the airway walls.

Figure 45:
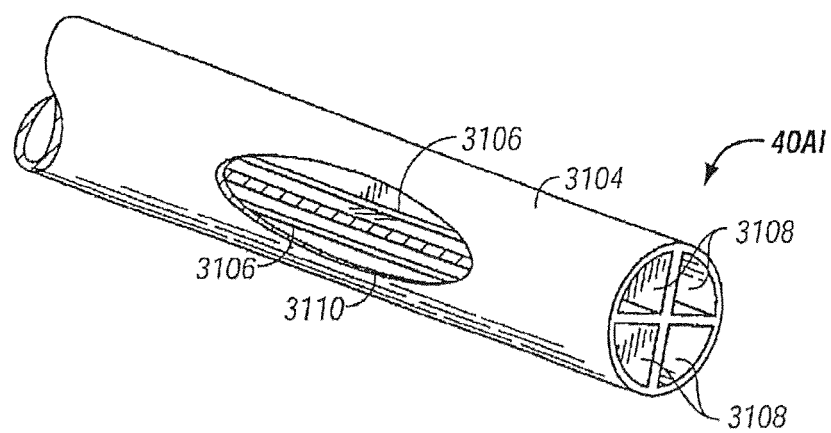
FIG. 45 is a side view of an embodiment of a treatment apparatus having a plurality of lumens containing electrodes for use with the methods of the present invention.

FIGS. 45 and 46 illustrate embodiments of treatment apparatus 40AI, 40AJ in which electrodes 3106 in the form of wires are positioned in one or more lumens 3108 of a catheter 3104. Openings 3110 are formed in the side walls of the catheters 3104 to expose the electrodes 3106. As shown in FIG. 45, the treatment apparatus 40AI has multiple lumens 3108 with electrodes provided in each of the lumens. The side wall of the treatment apparatus 40AI is cut away to expose one or more of the electrodes 3106 through a side wall opening 3110. In FIG. 45, the opening 3110 exposes two electrodes positioned in adjacent lumens. The treatment apparatus 40AI may be provided with a biasing member as discussed above to bring the electrodes 3106 of the treatment apparatus into contact with the airway wall.

The treatment apparatus 40AJ of FIG. 46 includes a catheter 3104 which has been foitned into a loop shape to allow the electrode 3106 to be exposed on opposite sides of the device which contact opposite sides of the airway. The resilience of the loop shape causes the electrodes to come into contact with the airway walls.

The treatment apparatus 40AK of FIG. 47 is in the form of a balloon catheter. The treatment apparatus 40AK includes electrodes 3118 positioned on an exterior surface of an inflatable balloon 3116. The electrodes 3118 are electrically connected to the energy source 3032 by the leads 3120 extending through the balloon and through the lumen of the balloon catheter 3114. The balloon 3116 is filled with a fluid such as saline or air to bring the electrodes into contact with the airway wall 3100.

FIG. 48 illustrates an alternative embodiment of a balloon catheter treatment apparatus 40AM in which a fluid within the balloon 3126 is heated by internal electrodes 3128. The electrodes 3128 are illustrated in the shape of coils surrounding the shaft of the catheter, however other electrode shapes may also be used. The electrodes 3128 may be used as resistance heaters by application of an electric current to the electrodes. Alternatively, radio frequency or microwave energy may be applied to the electrodes 3128 to heat a fluid within the balloon 3126. The heat then passes from an exterior of the balloon 3126 to the airway wall. The radio frequency or microwave energy may also be applied indirectly to the airway wall through the fluid and the balloon. In addition, hot fluid may be transmitted to the balloon 3126 from an external heating device for conductive heating of the airway tissue.

Figure 49A:
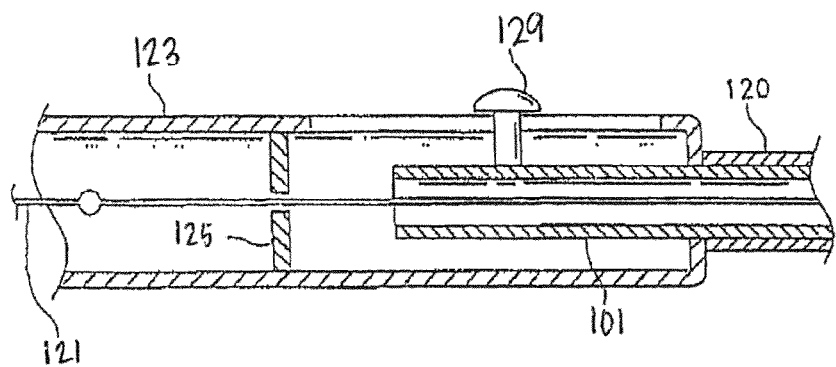
FIGS. 49A-49F illustrate a variation of the invention and a deployment member for deploying the device.
Figure 49B:
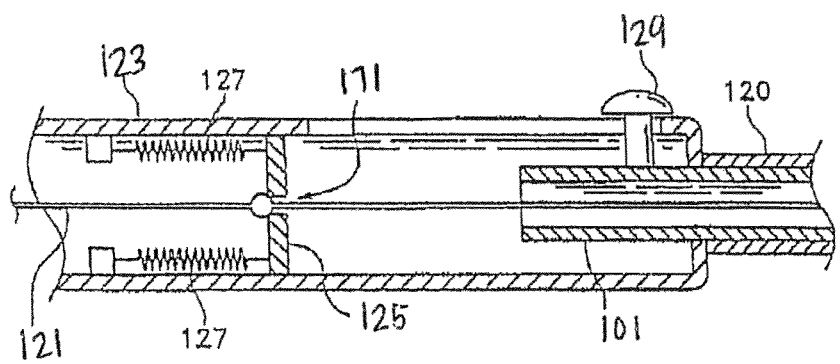
Figure 49C:
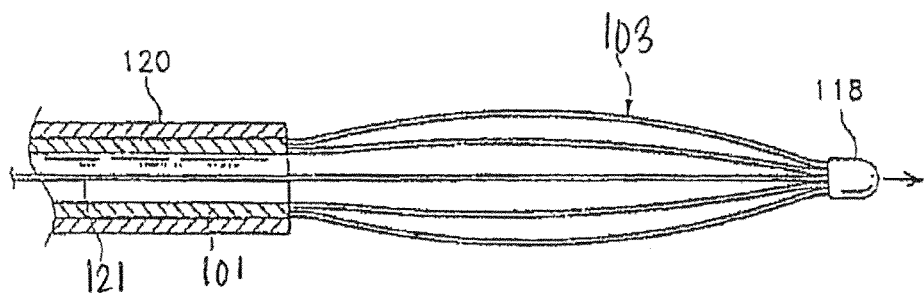
Figure 49D:
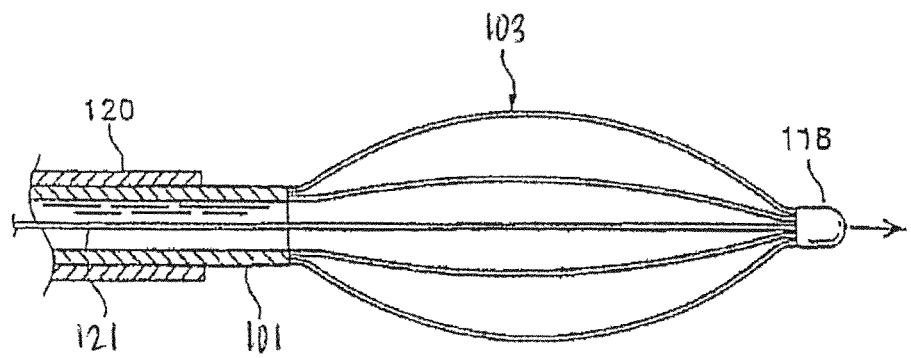

FIGS. 49A-49F illustrate variations of the inventive device that use an expanding force to expand the basket. FIG. 49A illustrates a deployment member of the device. FIG. 49B illustrates the device of FIG. 49A when the elongated member is moved in a distal direction to a deployment point. FIGS. 49C-49D illustrate the elongated member 101, sheath 120, expandable member 103, distal tip 118, and wire 121 extending through the device. FIG. 49C illustrates the basket 103 in a first unexpanded state when the elongated member 101 and wire 121 are proximal of the deployment point 171. FIG. 49D illustrates the expansion of the basket 103 to a second expanded state as the elongated member 101 moves distally and the wire 121 is restrained at the deployment point 171.

Turning now to FIG. 49A, the deployment member may comprise a handle 123 which is adjacent to a proximal portion of an elongated member 101. The handle may be designed to be operated by a single hand, either right or left. The handle may also have a control switch for operation of the device. Such a switch could control the power supply attached to the device as well. Also, the handle may be configured to determine the position of the device within a human body as the device is advanced to a target site. For example, marks on the handle or even a readout could provide information to the user as to the relative deployment state of the expandable member. Also, a sensor may be placed on the handle 123, this sensor may be used to determine the position of the expandable member. Such a sensor could also be used to measure the size of the airway, such a measurement could be used as a control variable to determine the amount of energy that the device power supply must deliver. The handle 123 may control the expandable member using force compensation (e.g., a spring, etc.) or deflection limiting stops to control the expansion of the expandable member. Such force compensation or deflection stops provide a limit to the expansion member to avoid over-expansion of a particular airway.

Turning now to the handle 123 of FIG. 49A, an elongated member 101 may be slidably mounted to the handle. The variation of the invention depicted in these Figures may also, but does not necessarily, include a sheath 120 exterior to the elongated body 101. A wire 121 extends from the handle through the elongated member 101 and may be attached to a distal tip 118 of the device. The wire 121, elongated member 101, and distal tip (not shown) are slidably moveable in both a distal and proximal directions. The handle may also include a stop 125 which prevents the wire 121 from moving distally beyond a deployment point 171. The stop 125 may be connected to a spring (not shown) to limit the expansion of the expandable member upon reaching a pre-determined force. The handle 123 may include a control member 129 that is moveably attached to the handle 123 for moving the elongated member 101 in a distal/proximal direction. Although the handle 123 in the figures is depicted to have a control member 129 as illustrated, other variations of control members are also contemplated to be within the scope of this invention. For example, though not illustrated, a handle 123 may include other configurations, such as lever, thumbwheel, screw-mechanism, ratchet mechanism, etc., which are attached to the handle 123 to provide control actuation for the expandable member.

FIG. 49B illustrates a variation of the inventive device when the elongated member 101 and wire 121 are moved in a distal direction. In this illustrations, a stop 125 prevents the wire 121 from moving distally of a deployment position 171. This illustration further illustrates a variation of the invention where the stop 125 is attached to springs 127 which provide force compensation for the expandable member on the device. Although not shown, a control member 129 may have a stop which limits its travel along a handle 123. Such a stop is an example of a deflection limiting mechanism which controls the movement of the control member 129, thus controlling the extent of the expansion of the expandable member.

FIG. 49C illustrates the invention when the expandable member or basket 103 is in a first unexpanded state. As noted above, the wire 121 is attached to a distal tip 118 of the device and both are prevented from distal movement when the wire 121 is in the deployment position 171. Therefore, as depicted in FIG. 49D, movement of the elongated member 101 in a distal direction against a distal tip 118, that is restrained by a wire 121, causes a basket 103 to compress between the advancing elongated member 101 and the stationary distal end 118. Thus, the basket 103 is forced outward and radially expands into a second expanded state. As noted above, the wire 121 may also be used to transfer energy to or from the energy transfer elements found on the basket 103. Also, it is contemplated that the wire 121 may be a wire, a ribbon, a tube, or of any other equivalent structure. Also contemplated, but not shown, is a detent means for maintaining the elongated member in a distal position to expand the basket 103 against the distal tip 118 without the need for continual applied force by a user of the device. Also contemplated is a ratchet member, or friction member to maintain the basket 103 in the expanded state.

Figure 49E:
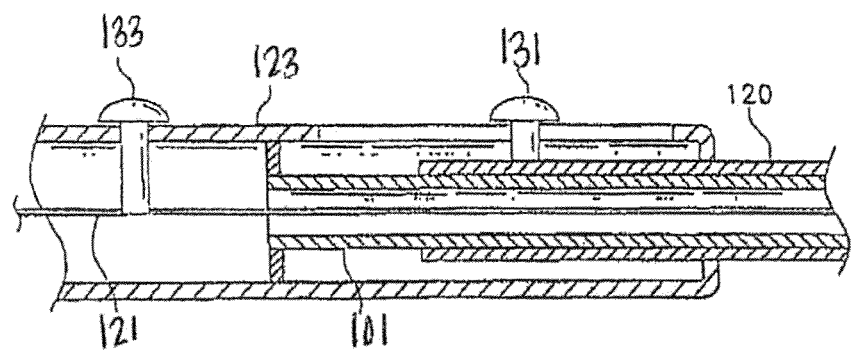
Figure 49F:
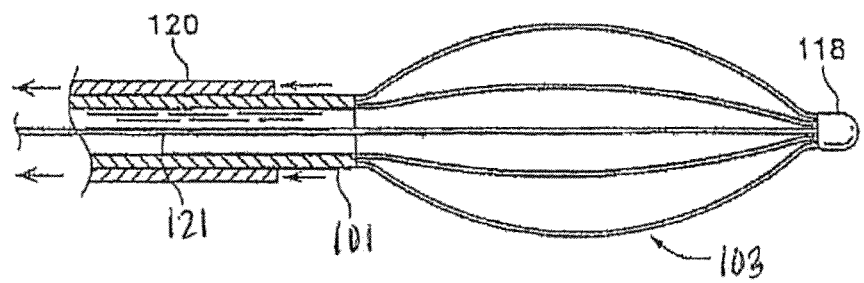

FIG. 49E illustrates another variation of a deployment member. In this variation, a sheath 120 may be slidably attached to a handle 123. In this variation, the elongate member 101 is rigidly attached to the handle 123. The sheath 120 may be attached to a first control member 131. A wire 121 extends through the elongate member 101 and is attached to the distal tip of the device (not shown). The wire 121 may be attached to a second control member 133. As indicated in FIG. 49F, proximal movement of the first control member 131 causes the sheath 120 to proximally retract over the elongate member 101 and uncover the expandable portion (not shown). Proximal movement of the second control member 133 causes the wire 121, distal joint, and expandable member to move against the non-moving elongate member 101 which causes the expandable member to expand into a second state.

Figure 49G:
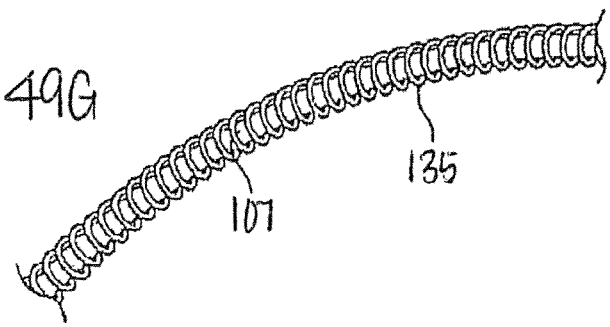
FIGS. 49G-49I illustrate examples of energy transfer elements of the device.
Figure 49H:
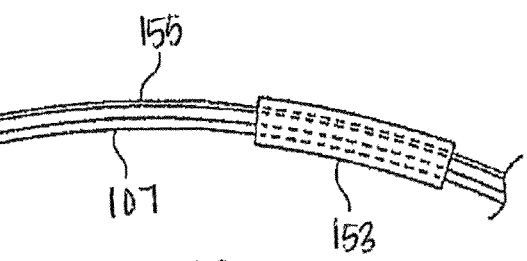
Figure 49I:

Turning now to the energy transfer elements located on the expandable portion, FIGS. 49G-49I illustrate examples of energy transfer elements that may be located on the expandable portion of the device. In the variation of the invention where the expandable portion comprises a basket having basket legs 107, the basket legs 107 may function as heat exchange elements. In other words, the device may be configured so that the leg is an electrode or the conductive heating element. In these variations, the leg 107 may be partially covered with an insulation only leaving an active region exposed for delivery of energy to the airways. Examples of such insulation include a heat shrink sleeve, a dielectric polymeric coating, or other material which may function as an insulator.

FIG. 49G illustrates an example of a basket leg 107 with an energy transferring element 135 coiled around the leg 107. In this example, the energy transferring element uses conductive heating and comprises a resistance heating element 135 coiled around the leg 107. FIG. 49H illustrates a variation of the invention having an RF electrode attached to the basket leg 107. The RF electrode may be attached to the basket leg 107 via the use of a fastener 153. For example, the electrode may be attached via the use of a heat shrink fastener 153, (e.g., polymeric material such as PET or polyethylene tubing).

FIG. 49I illustrates another variation of the invention where the energy transfer element is a printed circuit 173 that is situated around the leg 107 and secured to the leg. Also contemplated, but not shown for use as energy transfer elements are a polymeric heating material, an electrically conductive paint, a resistance element sputtered onto the leg in a pattern or formed on a substrate by photofabrication. Also, the basket leg itself may be chosen of appropriate size and resistivity to alloy dual use as a basket and energy transfer element. Many nickel-chromium alloys have both high specific resistance and significant spring-like properties. In any variation of the invention the use of adhesives or other coatings may also be used to secure the energy transfer element to the basket leg 107. Also, the energy transfer elements are not limited to what is illustrated in the drawings. It is also contemplated that other types of energy transfer elements may be used such as radiant, laser, microwave, and heat energy.

Figure 50A:
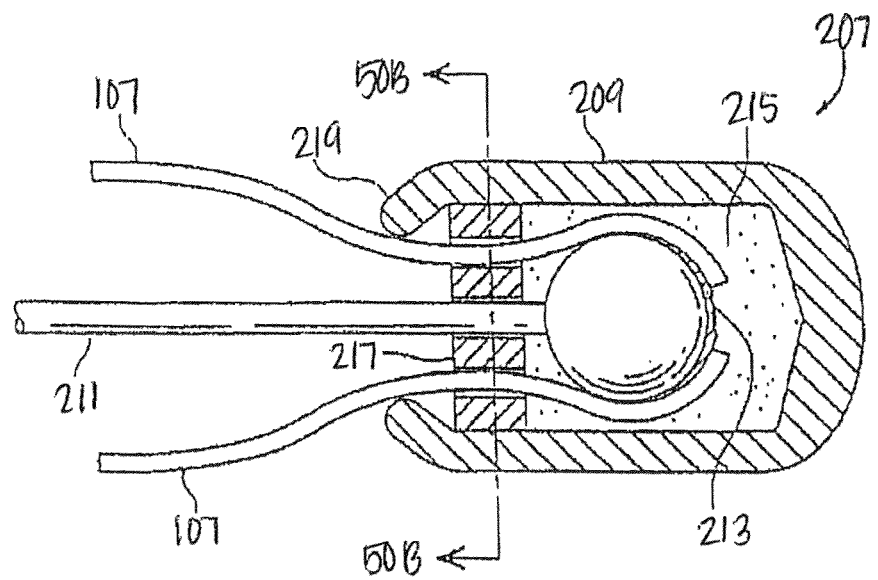
FIGS. 50A-50D illustrate distal joints of the invention.
Figure 50B:
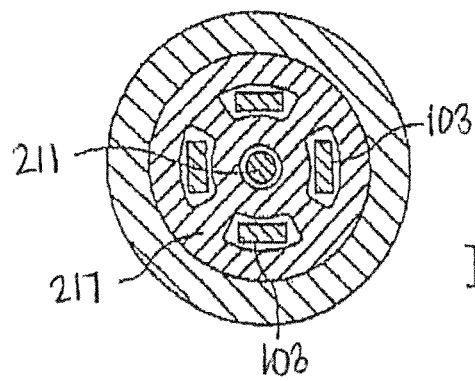

FIG. 50A illustrates a variation of a distal tip 207 having a redundant joint. The distal tip 207 has a polymeric cap 209 covering the distal ends of the basket legs 107 and wire 211. The legs 107 are soldered 213 to the distal end of the wire 211. Also used to maintain the joint is an adhesive 215 substantially filling the polymeric cap 209. A multi-lumen piece 217 separates the legs 107 and wire 211. A side view of the multi-lumen piece 217 is shown in FIG. 50B. A multi-lumen tubing may be used for the multi-lumen piece 217. The ends 219 of the polymeric cap 209 may be heat formed or otherwise tapered down around the legs 107.

Figure 50C:
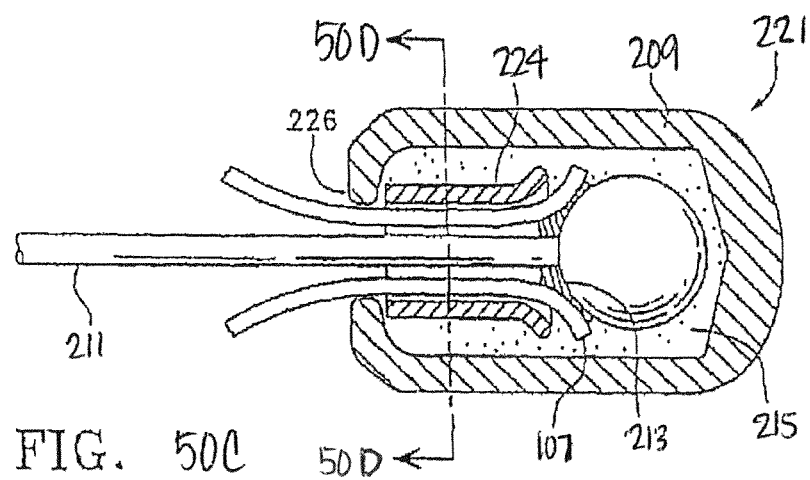
Figure 50D:
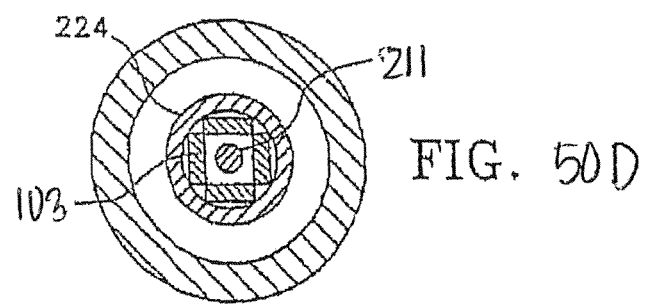

FIG. 50C illustrates another variation of a distal tip 221 having a redundant joint. The distal tip 221 has a polymeric cap 209 covering the distal ends of the basket legs 107 and wire 211. The legs 107 are soldered 213 to the distal end of the wire 211. Also used to maintain the joint is an adhesive 215 substantially filling the polymeric cap 209. A hypo-tube 224 covers the legs 107 and wire 211. A side view of the hypo-tube 224 is shown in FIG. 50D. The distal end of the hypo-tube 224 may be flared to seat a ball located on a distal end of the wire 211 and the legs 107. A proximal end of the hypo-tube 224 may be flared to provide greater interlock with ends 219 of the polymeric cap 209. As shown in FIG. 50C, the ends of the legs 107 taper outwards from the hypo-tube 224 and form an area with a diameter larger than the end of the cap 226 which may be tapered down around the legs 107 and wire 211. The ends 219 of the polymeric cap 209 may be heat formed or otherwise tapered down.

Figure 50E:
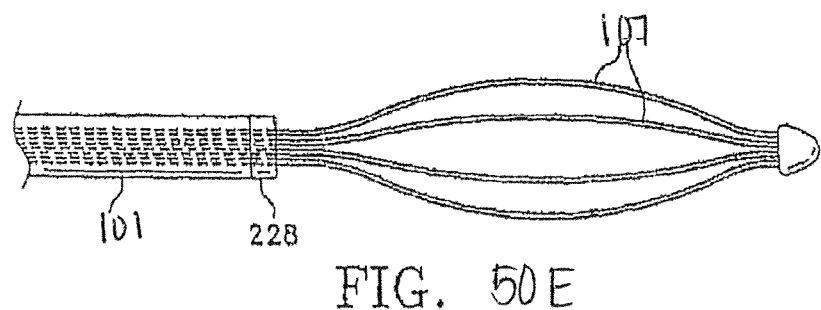
FIG. 50E illustrates a proximal joint of the invention.

FIG. 50E shows another variation of the invention having a hoop or ring 228 at a proximal joint of the device. The hoop 228 may be soldered or welded to the legs 107 and keeps the legs 107 attached even if a joint fails between the legs and the elongate member 101. Also, the hoop 228 may electrically connect the legs, preventing disconnection of single leg 107 having a temperature sensing element attached.

The invention also includes a temperature detecting element (not shown). Examples of temperature detecting elements include thermocouples, infrared sensors, thermistors, resistance temperature detectors (RTDs), or any other apparatus capable of detecting temperatures or changes in temperature. The temperature detecting element is preferably placed in proximity to the expandable member. In one variation, a temperature sensor may be mounted along a pull wire. For the variations depicted in FIGS. 49G-49I, a temperature sensor may be mounted between the energy transfer elements 135, 155, 173 and the leg 107. In one variation of the invention a temperature sensor is placed on a single basket leg 107 to provide a signal to control energy transfer. It is also contemplated that a temperature sensor may be placed on more than one basket leg 107, and/or on a central wire to provide control for multiple areas of energy transfer. The temperature sensor may be placed on the inside of the basket leg 107 to protect the temperature sensor while still providing a position advantageous to determining the device temperature at the energy transfer element.

Figure 49J:
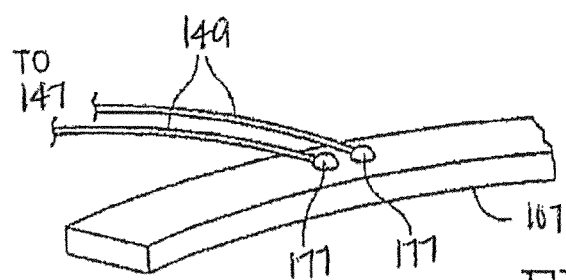
FIG. 49J shows a partial view of a thermocouple attached to a basket leg.

FIG. 49J illustrates a variation of the invention having thermocouple leads 149 attached to a leg 107 of the device. The leads may be soldered, welded, or otherwise attached to the leg 107. This variation of the invention shows both leads 149 of the thermocouple 147 attached in electrical communication to a leg 107 at separate joints 177. In this case, the temperature sensor is at the surface of the leg. This variation provides in case either joint becomes detached, the circuit will be open and the thermocouple 147 stops reading temperature. The device may also include both of the thermocouple leads as having the same joint.

FIGS. 51A-51D illustrate variations of the device in which impedance may be varied by wiring the basket legs 107 in series or in parallel. FIG. 51A illustrates a series wiring diagram in which a current path 157 flows from a first leg to a second leg 107, a third leg 107, and a fourth leg 107, sequentially. FIG. 51B illustrates the series wiring diagram and shows a single wire 143 connecting the legs 107 in series. The wire 143 may, for example, extend to a distal end of the leg and wrap over itself to the proximal end of the leg 107. A covering (not shown) may be placed over the wire 143 wrapped leg 107 at the proximal end of the device. FIG. 51C illustrates another variation of a series wiring diagram. In this example, a wire 143 extends from the proximal end of a leg 107 to its distal end and then extends to the distal end of an adjacent leg 107 and extends back to the proximal end of the adjacent leg 107.

FIG. 51D illustrates a parallel wiring diagram in which a current path 157 flows to each leg 107. Series wiring has an added advantage in that all current will pass through each energy transfer element. By design, this configuration equalizes the heat dissipated at each leg through construction of legs with equal resistance. In addition, in the event of failure of any electrical connection, no energy is delivered. This provides an additional safety feature over parallel wiring. As mentioned elsewhere, the electrical current may be AC or DC. AC may be delivered in the RF range as a safety measure additional to electrical isolation. DC may be used to allow a portable device powered by a battery pack or provide an energy source within the device itself.

Figure 52A:
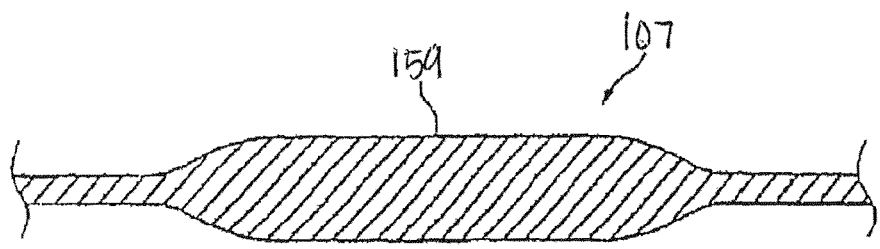
FIGS. 52A-52C illustrate examples of variable thicknesses of legs of the basket.
Figure 52B:
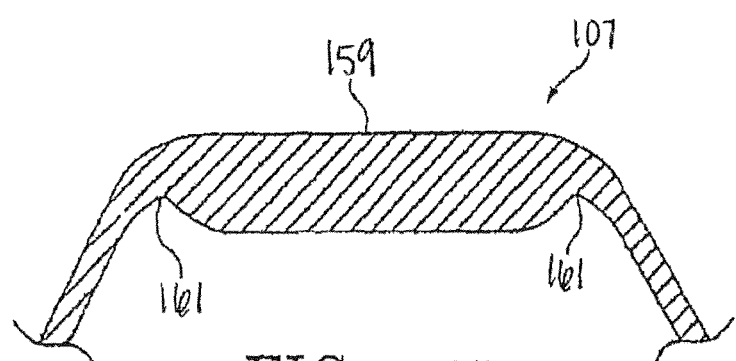
Figure 52C:
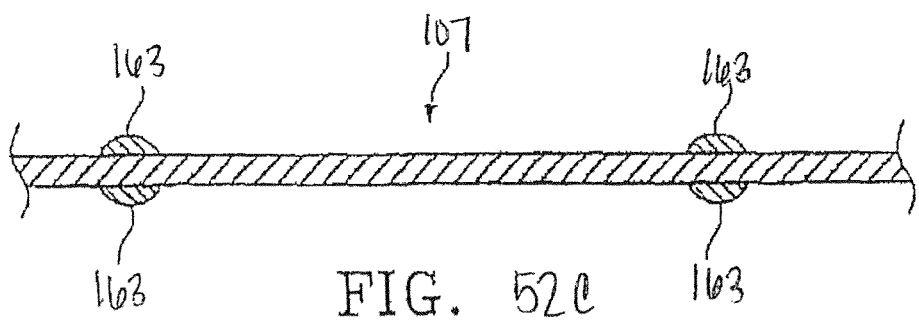

FIGS. 52A-52C illustrate variations of the legs 107 of the basket 103. As discussed above, the legs may, for example, comprise a stainless steel, or a shape memory/superelastic alloy such as a nitinol material. The basket legs 107 may have a rectangular cross section in those variations where the legs 107 are formed from ribbons, or the legs 107 may have a circular cross section in variations where the legs 107 are formed from wires. Also, a leg 107 may be configured to have a non-axisymmetric cross-section. For example, the leg may have an oval or flat cross section as well. The legs 107 of a basket 103 need not all have similar cross sections. For instance, the cross section of each of the legs 107 in a basket 103 may be individually chosen to optimize such factors as the resilience of the basket 103, or to optimize energy transfer characteristics. An example of a cross section of a basket leg 107 is seen in FIG. 52A which illustrates a top view of a basket leg 107 that has a contoured shape 159. In this illustration, the energy exchange element is not shown in the figure for clarity. One of the purposes of such a contoured shape 159 is illustrated in FIG. 52B. When the basket (not shown) expands to its second state, leg 107 is configured to bend at or substantially near to points 161. A benefit of such a configuration is to allow a substantially parallel active surface as defined by the contour shape 159. FIG. 52C illustrates another variation of a leg 107. In this variation, the leg 107 has a region of increased diameter 163 in the case of round wire, or increased width or thickness in the case of rectangular or other non-axisymmetric wire. Such a region 107 could also be a flat wire with bumps or protrusions creating areas of increased width of the flat wire. This region 163 may, for example, provide a stop that assists in locating insulation, heat shrink, or other external covering around the leg 107. Also contemplated is a leg 107 that consists of a composite construction. In this variation, the leg 107 may comprise of differing materials in predetermined regions to control the bending of the leg 107 as the basket 103 expands, or the leg may be constructed of different materials to selectively control regions of deliver of energy on the leg.

FIGS. 53A-53D illustrate another variation of the inventive device in which the expandable member comprises basket from a single piece or sheet of material. Such a configuration could comprise an etched, machined, laser cut, or otherwise manufactured piece of metal. FIG. 53A illustrates a partial view of a basket 103 formed from a single piece of material. The thickness of the material is, for example 0.005 inches but may vary as desired. The illustration of FIG. 53A shows the basket 103 prior to being wrapped about the Z direction as indicated. As shown, the legs 107 may be of varying length or they may be the same length 107 or a combination thereof. The basket 103 may have a distal portion 167 or basket head 167 which may be configured to facilitate construction of the device. For example, the basket head 167 may be notched 166 to obtain a desired shape as the basket is wrapped about the Z direction. FIG. 53B illustrates a variation of the basket head 165 being notched such that sections 165 of the material may be bent from the plane of the material to form tabs 165. Tabs 165 may be used to form mechanical joints with another part, such as a distal tip cap. FIG. 53C illustrates another variation of a basket 103 made from a single piece of material. In this example, the legs 107 of the basket 103 are bent in a direction orthogonal to the plane of the basket head 167. In this example, the distance between the ends of the legs 107 may be, for example, about 2.75 inches. FIG. 53D illustrates a variation of the proximal ends of the legs 107 of the basket 103. In this example, the proximal ends of the legs 107 may have features 169 which promote the structural integrity of the proximal joint (not shown) of the device. In this variation, the ends of the legs 107 have a saw-tooth design which improve the integrity of the proximal joint connecting the legs 107 to the elongated member. The variation of FIG. 53D also illustrates a proximal end of the leg 107 as having a radius, however, the end of the leg 107 may have other configurations as required. Also, the legs 107 may have a width of, for example, 0.012 inches and a separation of, for example, 0.016 inches. However, these dimensions may vary as needed.

The energy delivery device may further comprise a temperature detecting element. Examples of temperature detecting elements include thermocouples, infrared sensors, thermistors, resistance temperature detectors (RTDs), or any other apparatus capable of detecting temperatures or changes in temperature. The temperature detecting element is preferably placed in proximity to the expandable member.

Figure 6:
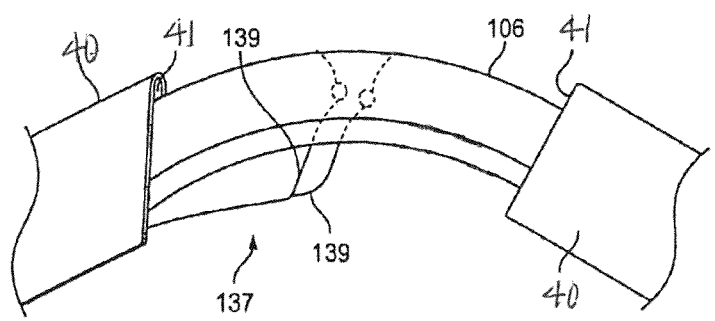
FIG. 6 is a partial view of a thermocouple attached to an energy delivering device in accordance with the invention.

FIG. 5 is a partial view of a variation of the energy delivery device having thermocouple 137 positioned about midway along basket leg 106. FIG. 6 is an enlarged partial view of the thermocouple 137 of FIG. 5 showing the leads 139 separately coupled on an inwardly-facing surface of the leg 106. Consequently, the basket leg itself is used as part of the thermocouple junction upon which the temperature measurement is based. The thermocouple junction is intrinsic to the basket leg. This configuration is preferred because it provides an accurate temperature measurement of tissue contacting the leg 106 in the vicinity of the thermocouple leads. In contrast, typical thermocouple configurations consist of a thermocouple junction offset or extrinsic to the basket leg. Thermocouple junctions offset or extrinsic to the basket leg do not measure temperature as accurately in certain applications as thermocouple junctions which are intrinsic to the basket leg.

An intrinsic thermocouple junction configuration is safer than an extrinsic thermocouple junction because, in the event one of the thermocouple leads separates from a basket leg, the intrinsic thermocouple junction becomes "open" and no thermocouple signal is produced. In contrast, when an extrinsic thermocouple junction separates from a basket leg a signal continues to be produced. The signal of a detached extrinsic thermocouple junction can be misleading because although a temperature reading continues to be produced, the temperature reading does not reflect the temperature at the point where the basket leg contacts the subject tissue. Accordingly, an intrinsic thermocouple junction having two leads separately attached to a basket leg is preferred.

FIG. 6 also shows basket leg 106 having an outer insulating material or coating 40. The boundaries 41 of the insulating material 40 define an uninsulated, active section of electrode leg 106 which delivers energy to the airway walls. Preferably, the insulating coating 40 is heat shrink tubing or a polymeric coating. However, other insulating materials may be used.

Various controllers may be used to carry out the invention. An example of an RF controller which may be used to carry out the invention is described in co-pending International Patent Application No. PCT/US01/32321, entitled "CONTROL SYSTEM AND PROCESS FOR APPLICATION OF ENERGY TO AIRWAY WALLS AND OTHER MEDIUMS" filed Oct. 17, 2001, incorporated herein by reference in its entirety. As stated in that PCT application, an example of a RF generator which may be modified in accordance with the present invention is the FORCE™ 2 Generator manufactured by Valleylab, Boulder, Colo., U.S.A. Another suitable technique to generate and control RF energy is to modulate RF output of a RF power amplifier by feeding it a suitable control signal.

The controller and power supply is configured to deliver enough energy to produce a desired effect in the lung. The power supply should also be configured to deliver the energy for a sufficient duration such that the effect persists. This may be accomplished by a time setting which may be entered into the power supply memory by a user.

The power supply or generator may also employ a number of algorithms to adjust energy delivery, to compensate for device failures (such as thermocouple detachment), to compensate for improper use (such as poor contact of the electrodes), and to compensate for tissue inhomogeneities which can affect energy delivery such as, for example, subsurface vessels, adjacent airways, or variations in connective tissue.

The power supply can also include circuitry for monitoring parameters of energy transfer: (for example, voltage, current, power, impedance, as well as temperature from the temperature sensing element), and use this information to control the amount of energy delivered. In the case of delivering RF energy, typical frequencies of the RF energy or RF power waveform are from 300 to 1750 kHz with 300 to 500 kHz or 450 to 475 being preferred. The RF power-level generally ranges from about 0-30 W but depends upon a number of factors such as the size and number of the electrodes. The controller may also be configured to independently and selectively apply energy to one or more of the basket leg electrodes.

A power supply may also include control modes for delivering energy safely and effectively. Energy may be delivered in open loop (power held constant) mode for a specific time duration. For example, a power setting of 8 to 30 Watts for up to 10 seconds is suitable and a power setting of 12 to 30 Watts for up to 5 seconds is preferred. For more permanent restructuring of the airways, a power setting of 8 to 15 Watts for 5 to 10 seconds is suitable. For mere temporary relief or enlargement of the airway, a power setting of 10 to 25 Watts for up to 3 seconds is suitable. With higher power settings, correspondingly lower time durations are preferred to limit collateral thermal damage.

Energy may also be delivered in temperature control mode, with output power varied to maintain a certain temperature for a specific time duration. For example, energy may be delivered for up to 20 seconds at a temperature of 55 to 80° C., and more preferably, energy is delivered up to 10 seconds at a temperature in the range of 60 to 70° C. For more permanent restructuring of the airways, energy is delivered for 5 to 10 seconds at a temperature in the range of 60 to 70° C. For mere temporary relief or enlargement of the airway, energy is delivered for up to 5 seconds at a temperature of 55 to 80° C. Additionally, the power supply may operate in impedance control mode.

The operator may start at low values of power, temperature and time, and treat until the desired effect (for example, airway diameter increasing or tissue blanching) is acutely observed, raising the power, temperature or time as needed.

As described in International Patent Application No. PCT/US01/32321, entitled "CONTROL SYSTEM AND PROCESS FOR APPLICATION OF ENERGY TO AIRWAY WALLS AND OTHER MEDIUMS" filed Oct. 17, 2001, incorporated by reference in its entirety above, in the case of RF energy delivery via RF electrodes, the power supply may also operate in impedance control mode. Various other modes of operation and control algorithms disclosed in the incorporated PCT application are now described immediately below. They include "Temperature Control Mode," "Energy Pulses and Energy Modulation,", "Feedback Algorithm," "Power Shut Down Safety Algorithms," and "Examples."

Temperature Control Mode

In a temperature control mode, the power supply may operate up to a 75° C. setting. That is, the temperature measured by the thermocouple can reach up to 75° C. before the power supply is shut off. The duration must be long enough to produce the desired effect, but as short as possible to allow treatment of all of the desired target airways within a lung. For example, up to 15 seconds is suitable, and more preferably 8 to 12 seconds with about 10 seconds per activation (while the device is stationary) being preferred. Shorter duration with higher temperature will also produce an acceptable acute effect.

It should be noted that different device constructions utilize different parameter settings to achieve the desired effect. For example, while direct RF electrodes typically utilize temperatures up to 75° C. in temperature control mode, resistively heated electrodes may utilize temperatures up to 90° C.

Energy Pulses and Energy Modulation

Short bursts or pulses of RF energy may also be delivered to the target tissue. Short pulses of RF energy heat the proximal tissue while the deeper tissue, which is primarily heated by conduction through the proximal tissue, cools between the bursts of energy. Short pulses of energy therefore tend to isolate treatment to the proximal tissue.

The application of short pulses of RF energy may be accomplished by modulating the RF power waveform with a modulation waveform. Modulating the RF power waveform may be performed while employing any of the other control algorithms discussed herein so long as they are not exclusive of one another. For example, the RF energy may be modulated while in a temperature control mode.

Examples of modulation waveforms include but are not limited to a pulse train of square waves, sinusoidal, or any other waveform types. In the case of square wave modulation, the modulated RF energy can be characterized in terms of a pulse width (the time of an individual pulse of RF energy) and a duty cycle (the percent of time the RF output is applied). A suitable duty cycle can be up to 100% which is essentially applying RF energy without modulation. Duty cycles up to 80% or up to 50% may also be suitable for limiting collateral damage or to localize the affect of the applied energy.

Feedback Algorithm

As indicated above, the present invention includes controllers having various algorithms The algorithms may be either analog and digital based. A preferred embodiment is a three parameter controller, or Proportional-Integral-Derivative (PID) controller which employs the following algorithm: $Pi_+i = Pj + G(\alpha ej + \beta ei - i + \gamma ej\_)$ where $Pi_+i$ is a new power set point, $Pj$ is a previous power set point, $\alpha$, $\beta$ and $\gamma$ are preset values, G is a variable gain factor and e, en, ej– correspond to error at the present time step, error one step previous and error two steps previous where the error is the difference between the preset temperature and a measured temperature.

We have found that by using a variable gain factor (G) to adaptively control RF energy delivery, the system of the present invention can treat a wide range of tissue types including lung tissue bronchus, bronchioles and other airway passages. The variable gain factor scales the coefficients (alpha, beta, and gamma; each a function of the three PID parameters) based on, for example, the temperature response to energy input during the initial temperature ramp up.

Exemplary PID parameters are presented herein, expressed in alpha-beta-gamma space, for an energy delivering device and controller of the present invention. These settings and timings are based on testing in various animal lung tissues using an energy delivering apparatus as described above. First, the gain factor preferably varies and is reset 0.1 to 2 and more preferably at 0.5 seconds after energy delivery has begun. Preferably, the gain factor is reset as follows: G is reset to 0.9 to 1.0 and preferably 0.9 if a temperature rise in ° C. per Joule is less than or equal to 2.5; G is reset to 0.4 to 0.5 and preferably 0.5 if a temperature rise in ° C. per Joule is between 2.5 to 5.0; G is reset to 0.2 to 0.3 and preferably 0.2 if a temperature rise in ° C. per Joule is equal to 5.0 to 7.5; and G is reset to 0.1 to 0.2 and preferably 0.1 if a temperature rise in ° C. per Joule is greater than 7.5. We have also found that a suitable value for α is from 1 to 2; for β is from −1 to −2; and for γ is from −0.5 to 0.5. More preferably α, β, γ are 1.6, −1.6, and 0.0 respectively.

It is also possible to change the relative weights of alpha, beta, and gamma depending upon monitored temperature response working in either PID or Alpha-Beta-Gamma coordinate space beyond just scaling the alpha-beta-gamma coefficients with a variable gain factor. This can be done by individually adjusting any or all of alpha, beta, or gamma.

In another variation of the present invention, the PID algorithm is $Pj_{+1}=P_i+(G\hat{i}+G\ ei_{-1}+G_3 ej\_)$ and G]; G and $G_3$ are each variable gain factors. The invention includes configuring the controller such that $G_1$ $G_2$ and $G_3$ are reset to 0.90 to 2.00, −0.90 to −2.00 and 0.50 to −0.50 respectively if a temperature rise in ° C. per Joule is less than or equal to 2.5; to 0.40 to 1.00, −0.40 to −1.00 and 0.25 to −0.25 respectively if a temperature rise in ° C. per Joule is between 2.5 to 5.0; to 0.20 to 0.60, −0.20 to −0.60 and 0.15 to −0.15 respectively if a temperature rise in ° C. per Joule is equal to 5.0 to 7.5; and to 0.10 to 0.40, −0.10 to −0.40 and 0.10 to −0.10 respectively if a temperature rise in ° C. per Joule is greater than 7.5. Each of the variable gain factors may be equal to a product of at least one preset value and at least one variable value.

It is also possible to employ an algorithm that continuously adapts to signals rather than at discrete sample steps, intervals or periods. The algorithm takes into account several variables upon which observed temperature response depends including, for example: initial temperature, time history of energy delivery, and the amount of energy required to maintain set point temperature. An exemplary analog PID algorithm is: $u=Kp\ e+Ki\int edt+Ko(de/dt)$ where u is a signal to be adjusted such as, for example, a current, a voltage difference, or an output power which results in energy delivery from the electrode to the airway wall. Kp, Ki and $K_D$ are preset or variable values which are multiplied with the proper error term where e(t) is the difference between a preset variable and a measured process variable such as temperature at time (t). The above equation is suitable for continuous and/or analog type controllers.

Power Shut Down Safety Algorithms

In addition to the control modes specified above, the power supply may include control algorithms to limit excessive thermal damage to the airway tissue. Damage may be limited by terminating or shutting down the energy being delivered to the target medium. The algorithms can be based on the expectation that the sensed temperature of the tissue will respond upon the application of energy. The temperature response, for example, may be a change in temperature in a specified time or the rate of change of temperature. The expected temperature response can be predicted as a function of the initially sensed temperature, the temperature data for a specified power level as a function of time, or any other variables found to affect tissue properties. The expected temperature response may thus be used as a parameter in a power supply safety algorithm. For example, if the measured temperature response is not within a predefined range of the expected temperature response, the power supply will automatically shut down.

Other control algorithms may also be employed. For example, an algorithm may be employed to shut down energy delivery if the sensed temperature does not rise by a certain number of degrees in a pre-specified amount of time after energy delivery begins. Preferably, if the sensed temperature does not increase more than about 10° C. in about 3 seconds, the power supply is shut off. More preferably, if the sensed temperature does not increase more than about 10° C. in about 1 second, the power supply is shut off.

Another way to stop energy delivery includes shutting down a power supply if the temperature ramp is not within a predefined range at any time during energy delivery. For example, if the measured rate of temperature change does not reach a predefined value, the power supply will stop delivery of the RF energy. The predefined values are predetermined and based on empirical data. Generally, the predefined values are based on the duration of time RF energy is delivered and the power-level applied. A suitable predefined rate of temperature change to stop energy delivery is from 8° C./second to 15° C./second in the first 5 seconds (preferably in the first 2 seconds) of commencing energy delivery.

Other algorithms include shutting down a power supply if a maximum temperature setting is exceeded or shutting down a power supply if the sensed temperature suddenly changes, such a change includes either a drop or rise, this change may indicate failure of the temperature sensing element. For example, the generator or power supply may be programmed to shut off if the sensed temperature drops more than about 10° C. in about 0.1 to 1 seconds and more preferably in about 0.2 seconds.

In another configuration, the power is terminated when the measured temperature exceeds a pre-selected temperature or exceeds the set point temperature by a pre-selected amount. For example, when the set point is exceeded by 5 to 20° C., more preferably 15° C. the power will terminate.

In another configuration, power is terminated when the measured temperature (averaged over a time window) exceeds a pre-selected temperature. For example, power may be terminated when the measured temperature (averaged over 1 to 5 seconds and preferably averaged over 2 seconds) exceeds the preset temperature by a predetermined amount. The predetermined amount is generally from 1 to 10° C. and preferably about 5° C. Suitable preset temperatures are from 60 to 80° C. and most preferably about 65° C. Accordingly, in one exemplary configuration, the power is stopped when the measured temperature (averaged over 2 seconds) exceeds 70° C.

In another configuration, the power is terminated when the amount of energy delivered exceeds a maximum amount. A suitable maximum amount is 120 Joules for an energy delivery apparatus delivering energy to the airways of lungs.

In another configuration, the power is shut down depending on an impedance measurement. The impedance is monitored across a treated area of tissue within the lung. Impedance may also be monitored at more than one site within the lungs. The measuring of impedance may be but is not necessarily performed by the same electrodes used to deliver the energy treatment to the tissue. The impedance may be measured as is known in the art and as taught in U.S. application Ser. No. 09/436,455 which is incorporated by reference in its entirety. Accordingly, in one variation of the present invention, the power is adjusted or shut off when a measured impedance drops below a preset impedance value. When using the energy delivering device of the present invention to treat airways, a suitable range for the preset impedance value is from 40 to 60 ohms and preferably about 50 ohms.

In another variation, the energy delivery apparatus is configured to deliver an amount of power up to a maximum power. The maximum power can be from 10 to 40 watts and preferably from 15 to 20 watts.

In yet another configuration, the power supply is configured to shut down if the power delivered exceeds a maximum power and the measured temperature drops by a critical temperature difference within a sampling period of time. A suitable maximum power is from 15 to 20 Watts and preferably about 17 watts. The sampling period of time generally ranges from 0.1 to 1.0 seconds and preferably is about 0.5 seconds. A suitable range for the critical temperature difference is about 2° C.

It is to be understood that any of the above algorithms and shut-down configurations may be combined in a single controller. However, algorithms having mutually exclusive functions may not be combined.

While the power supply or generator preferably includes or employs a microprocessor, the invention is not so limited. Other means known in the art may be employed. For example, the generator may be hardwired to run one or more of the above discussed algorithms. The controller is preferably programmable and configured to receive and manipulate other signals than the examples provided above. For example, other useful sensors may provide input signals to the processor to be used in determining the power output for the next step. The treatment of an airway may also involve placing a visualization system such as an endoscope or bronchoscope into the airways. The treatment device is then inserted through or next to the bronchoscope or endoscope while visualizing the airways. Alternatively, the visualization system may be built directly into the treatment device using fiber optic imaging and lenses or a CCD and lens arranged at the distal portion of the treatment device. The treatment device may also be positioned using radiographic visualization such as fluoroscopy or other external visualization means.

EXAMPLES

A system to treat airways in accordance with the present invention was built and tested in vivo on two canines. The system included an energy delivering apparatus having a distal basket. The basket included electrode legs and a temperature sensor mounted to one of the legs. The system also included a generator programmed to measure the temperature change per energy unit during the first half-second of treatment. A PID gain factor was adjusted depending on the measured tissue response. That is, the gain factor was adjusted based on the temperature change per joule output during the first half second. In general, this corresponds to a higher gain for less responsive tissue and lower gain for more responsive tissue.

After treating the test subjects with a general anesthetic, RF energy was delivered to target regions using an energy delivery device and generator as described above. In particular, energy activations were performed on all available intraparenchymal airways three millimeters or larger in diameter in both lungs. Three hundred sixty-three activations using a 65° C. temperature setting were performed in the two animals (i.e., 180 activations per animal). Additionally, in twenty of the activations in each animal, the energy delivery device was deliberately deployed improperly to provide a "Stress" condition.

In each activation, the measured temperature reached and stabilized at 65° C. or, in the case of the twenty activations under "stress" conditions, the power properly shut off. Thus, the present invention can successfully treat lung tissue with a variable gain setting and various safety algorithms to safely maintain a preset temperature at the electrode or lung tissue surface. This temperature control is particularly advantageous when treating the airways of lungs to reduce asthma symptoms.

Notably, the methods of the invention may be performed while the lung is experiencing natural symptoms of reversible obstructive pulmonary disease. One such example is where an individual, experiencing an asthma attack, or acute exacerbation of asthma or COPD, undergoes treatment to improve the individual's ability to breath. In such a case, the treatment provides immediate relief for (i.e., "rescues") the patient.

All of the features disclosed in the specification (including any accompanying claims, abstract and drawings), and/or all of the steps of any method or process disclosed, may be combined in any combination, except combinations where at least some of such features and/or steps are mutually exclusive.

Each feature disclosed, in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method for decreasing resistance to airflow within a bronchial tree of a subject, the method comprising:
 moving an intraluminal device along a lumen of an airway of the bronchial tree, the intraluminal device comprising an expandable member and an energy emitter; and
 damaging nerves along the airway by applying energy to the nerves from the energy emitter without destroying an inner surface of an airway wall disposed radially between the intraluminal device and the nerves, wherein damaging nerves along the airway comprises damaging nerve tissue adjacent to the airway wall.

2. The method of claim 1, wherein damaging nerves along the airway comprises damaging nerve tissue at a position that is within at least one of the left and right lung of the subject.

3. The method of claim 1, wherein the airway comprises a bronchus.

4. A method for decreasing resistance to airflow within a bronchial tree of a subject, the method comprising:
 moving an intraluminal device along a lumen of an airway of the bronchial tree, the intraluminal device comprising an expandable member and an energy emitter; and
 damaging nerves along the airway by applying energy to the nerves from the energy emitter without destroying an inner surface of an airway wall disposed radially between the intraluminal device and the nerves, wherein damaging nerves along the airway includes damaging nerve tissue extending along a tubular section of the airway wall so as to prevent nervous system signals transmitted along the airway wall from traveling past the damaged portion.

5. The method of claim 4, wherein damaging nerves along the airway comprises damaging at least one nerve at a position that is within a left lung or a right lung.

6. The method of claim 4, wherein damaging nerves along the airway comprises damaging nerve tissue adjacent to the airway wall.

7. A method for decreasing resistance to airflow within a bronchial tree of a subject, the method comprising:
 moving an intraluminal device along a lumen of an airway of the bronchial tree, the intraluminal device comprising an expandable member and an energy emitter; and
 damaging nerves along the airway by applying energy to the nerves from the energy emitter without irreversibly damaging an inner surface of an airway wall disposed radially between the intraluminal device and the nerves, wherein the airway comprises a bronchus.

8. The method of claim 7, wherein damaging nerves along the airway comprises damaging at least one nerve at a position that is within a left lung or a right lung.

9. The method of claim 7, wherein damaging nerves along the airway includes damaging nerve tissue extending along a tubular section of the airway wall so as to prevent nervous system signals transmitted along the airway wall from traveling past the damaged portion.

* * * * *